(12) United States Patent
Dressen et al.

(10) Patent No.: US 7,977,368 B2
(45) Date of Patent: Jul. 12, 2011

(54) PYRAZOLOPYRROLIDINES AS INHIBITORS OF GAMMA SECRETASE

(75) Inventors: Darren Dressen, Fremont, CA (US); Simeon Bowers, Oakland, CA (US); Albert W. Garofalo, South San Francisco, CA (US); Roy K. Hom, San Francisco, CA (US); Matthew N. Mattson, Santa Clara, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 389 days.

(21) Appl. No.: 12/124,358

(22) Filed: May 21, 2008

(65) Prior Publication Data

US 2009/0099235 A1 Apr. 16, 2009

Related U.S. Application Data

(60) Provisional application No. 60/931,840, filed on May 25, 2007.

(51) Int. Cl.
*A61K 31/40* (2006.01)
*A61K 31/4162* (2006.01)
*C07D 231/54* (2006.01)

(52) U.S. Cl. ........ 514/406; 514/360; 514/408; 514/422; 548/122; 548/400; 548/416; 548/418; 548/518

(58) Field of Classification Search .................. 514/338, 514/406, 360, 408, 422; 548/360.5, 122, 548/400, 416, 418; 546/275.7
See application file for complete search history.

(56) References Cited

U.S. PATENT DOCUMENTS

| 6,887,898 | B1 * | 5/2005 | Kim .............................. 514/545 |
| 7,732,609 | B2 * | 6/2010 | Ye et al. ......................... 546/119 |
| 2002/0193399 | A1 | 12/2002 | Lin et al. |
| 2005/0085506 | A1 | 4/2005 | Pissarnitski et al. |
| 2006/0100233 | A1 * | 5/2006 | Villa et al. ..................... 514/303 |
| 2006/0264380 | A1 | 11/2006 | Hellstrom et al. |

FOREIGN PATENT DOCUMENTS

| WO | 2005/030776 |    | 4/2005 |
| WO | 2007/022502 |    | 2/2007 |
| WO | 2007/064914 | A1 | 6/2007 |
| WO | 2007/143523 |    | 12/2007 |

OTHER PUBLICATIONS

Elser et al., Transition-state analogue inhibitors of γ-secretase bind directly to presenilin-1, Nature Cell Biol., 2(7), 428-434 (2000).
Li, Y.M. et al., "Photoactivated γ-secretase inhibitors directed to the active site covalently label presenilin 1," Nature, 405(6787), 689-694 (2000).
Seiffert, D. et al., "Presenilin-1 and -2 ARe Molecular Targets for γ-Secretase Inhibitors," J. Biol. Chem., 275(44), 34086-34091 (2000).
Konishi, J. et al., "γ-Secretase Inhibitor Prevents Notch3 Activation and Reduces Proliferation in Human Lung Cancers," Cancer Res., 67(17), 8051-8057 (2007).
Miele, L. et al., "NOTCH Signaling as a Novel Cancer Therapeutic Target," Curr. Cancer Drug Targets, 6(4), 313-323 (2006).
Buncel, E., "Chlorosulfates," Chem. Rev., 70(3), 323-337 (1970).
McDermott, S.D. et al., "Synthesis and Reactions of Sulfamides. A Review," Org. Prep. Proced. Int., 16(1), 49-77 (1984).
Chang, M.Y. et al., "Formal Synthesis of Epibatidine," Heterocycles, 65(7), 1705-1711 (2005).
Knochel, P. et al., "Highly Functionalized Organomagnesium Reagents Prepared through Halogen-Metal Exchange," Angew. Chem. Int. Ed., 42(36) 4302 (2003).
Liu et al., Synthesis of Enantiomerically Pure N-tert-Butanesulfinyl Imines (tert-Butanesulfinimines) by the Direct Condensation of tert-Butanesulfinamide with Aldehydes and Ketones, J. Org. Chem., 64, 1278-1284 (1999).
Davis et al., "Asymmetric Synthesis of cis-5-tert-Butylproline with Metal Carbenoid NH Insertion," J. Org. Chem., 68, 5147-5152 (2003).
Hosseini et al., "Dipeptide Analogues Containing 4-Ethoxy-3-pyrrolin-2-ones," Organic Letters, 8(10):2103-2106 (2006).
Fustero et al., "A Concise, Asymmetric Synthesis of Tetramic Acid Derivatives," Organic Letters, 4(21):3651-3654 (2002).
Yoda et al., "An Efficient Asymmetric Functionalization to Highly Substituted Pyrrolidines," Tetrahedron: Asymmerty, 6 (11):2669-2672 (1995).
Cogan et al., "Catalytic Asymmetric Oxidation of tert-Butyl Disulfide. Synthesis of tert-Butanesulfinamides, tert-Butyl Sulfoxides, and tert-Butanesulfinimines," Journal of the American Chemical Society, 120(32) 8011-8019 (1998).

(Continued)

*Primary Examiner* — Sreeni Padmanabhan
*Assistant Examiner* — Sahar Javanmard
(74) *Attorney, Agent, or Firm* — McDonnell Boehnen Hulbert & Berghoff LLP

(57) ABSTRACT

The invention provides compounds of Formula I

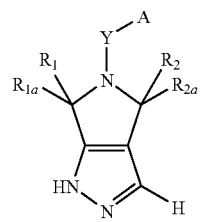

Formula I wherein A, Y, $R_1$, $R_{1a}$, $R_2$, and $R_{2a}$ are as described in the specification. Compounds of Formula I are useful in treating and/or preventing cognitive disorders, such as Alzheimer's disease. The invention also encompasses pharmaceutical compositions comprising compounds of Formula I, methods of preparing compounds of Formula I, and methods of treating cognitive disorders, such as Alzheimer's disease.

9 Claims, No Drawings

OTHER PUBLICATIONS

Davis et al., "Improved Synthesis of Enantiopure Sulfinimines (Thiooxime S-Oxides) from p-Toluenesulfinamide and Aldehydes and Ketones," J. Org. Chem., 64, 1403-1406 (1999).

David et al., "δ-Amino β-Keto Esters, a Designed Polyfunctionalized Chiral Building Block for Alkaloid Synthesis. Asymmetric Synthesis of (R)-(+)-2-Phenylpiperidine and (−)-SS20846A," Organic Letters, 2(8):1041-1043 (2000).

Davis et al., "Asymmetric Synthesis of Substituted Prolines from δ-Amino β-Ketoesters. Methyl (2S,5R)-(+)-5-Phenylprrolidine-2-carboxylate," Organic Letters, 4(9):1599-1602 (2002).

Guo et al., "Design, synthesis, an evaluation of tetrahydroisoquinoline and pyrrolidine sulfonamide carbamates as gamma-secretase inhibitors," Bioorganic and Medicinal Chemistry Letters, 17, 3010-3013 (2007).

\* cited by examiner

PYRAZOLOPYRROLIDINES AS INHIBITORS OF GAMMA SECRETASE

This application claims priority from U.S. Provisional application No. 60/931,840, filed May 25, 2007, which is incorporated by reference in its entirety.

BACKGROUND OF THE INVENTION

1. Field of the Invention

The invention relates to pyrazolopyrrolidine compounds, which inhibit gamma secretase and β-amyloid peptide release and/or its synthesis. Therefore, the compounds of the present invention are useful in the prevention and/or treatment of cognitive disorders in patients susceptible to cognitive disorders, and more specifically in preventing, treating, and/or halting the progress of neurodegenerative disorders such as Alzheimer's disease, dementia, mild cognitive impairment, dementia, Down's syndrome, and other similar diseases. The compounds of the invention are also useful for initiating or increasing angiogenesis.

2. State of the Art

Alzheimer's Disease (AD) is a degenerative brain disorder characterized clinically by progressive loss of memory, cognition, reasoning, judgment and emotional stability that gradually leads to profound mental deterioration and ultimately death.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 38-43 amino acids designated the β-amyloid peptide (βAP) or sometimes Aβ, AβP or β/A4. Glenner, G. G. et al (*Biochem. Biophys. Res. Commun.*, 120:885-890 (1984) first purified the β-Amyloid peptide and provided a partial amino acid sequence. The isolation procedure and the sequence data for the first 28 amino acids are described in U.S. Pat. No. 4,666,829.

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene-encoding APP has demonstrated that β-amyloid peptide arises as a peptide fragment that is cleaved from APP by protease enzyme(s). Sequential processing of the precursor protein by the enzymes referred to generically as beta- and gamma-secretases, give rise to the β-amyloid peptide fragment. Both enzymes have now been molecularly cloned, and characterized to differing levels.

Several lines of evidence indicate that progressive cerebral deposition of β-amyloid peptide plays a seminal role in the pathogenesis of AD and can precede cognitive symptoms by years or decades. See, for example, Selkoe, D J. *Neuron*, 6:487-498 (1991). The most important line of evidence is the discovery that missense DNA mutations at amino acid 717 of the 770-amino acid isoform of APP can be found in affected members but not unaffected members of several families with a genetically determined (familial) form of AD (Goate, A. et al., *Nature*, 349:704-706 (1991); Chartier-Harlin, M. C. et al., *Nature*, 353:844-846 (1991); and Murrell, J. et al., *Science*, 254:97-99 (1991).) Another such mutation, known as the Swedish variant, is comprised of a double mutation changing lysine$^{595}$-methionine$^{596}$ to asparagine$^{595}$-leucine$^{596}$ (with reference to the 695 isoform was found in a Swedish family) was reported in 1992 (Mullan, M. et al., *Nature Genet.*, 1:345-347 (1992). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP metabolism, and subsequent deposition of its β-amyloid peptide fragment, can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs, which are capable of inhibiting β-amyloid peptide release and/or its synthesis in vivo.

One approach toward inhibiting amyloid peptide synthesis in vivo is by inhibiting gamma secretase, the enzyme responsible for the carboxy-terminal cleavage resulting in production of β-amyloid peptide fragments of 40 or 42 residues in length. The immediate substrates for gamma secretase are β-cleaved, as well as α-cleaved carboxy-terminal fragments (CTF) of APP. The gamma-secretase cleavage site on β- and α-CTF fragments occurs in the predicted transmembrane domain of APP. Inhibitors of gamma-secretase have been demonstrated to effect amyloid pathology in transgenic mouse models (Dovey, H. F, et al. "Functional gamma-secretase inhibitors reduce beta-amyloid peptide levels in brain." *J Neurochem* 76 (1): 173-81 (2001))

Gamma secretase is recognized to be a multi-subunit complex comprised of the presenilins (PS1 or PS2), Nicastrin, Aph-1, and Pen 2 (De Strooper, B. "Aph-1, Pen-2, and Nicastrin with Presenilin generate an active gamma-Secretase complex." Neuron 38(1): 9-12 (2003); Edbauer, D., et al. "Reconstitution of gamma-secretase activity." *Nat Cell Biol* 5 (5): 486-8; (2003); Kimberly, W. T et al. "Gamma-secretase is a membrane protein complex comprised of presenilin, nicastrin, Aph-1, and Pen-2." *Proc Natl Acad Sci USA* 100 (11) 6382-7 (2003)). Much evidence indicates that PS comprises the catalytic moiety of the complex, while the other identified subunits are necessary for proper maturation and sub-cellular localization of the active enzyme complex (reviewed in De Strooper, B. "Aph-1, Pen-2, and Nicastrin with Presenilin generate an active gamma-Secretase complex." Neuron 38 (1): 9-12.) (2003). Consistent with this hypothesis: PS knock-out mice exhibit significant reductions in β-amyloid production (De Strooper. B et al., "Deficiency of presenilin-1 inhibits the normal cleavage of amyloid precursor protein." *Nature* 391(6665): 387-90 (1998); Haass, C. et al. "Alzheimer's disease. A technical KO of amyloid-beta peptide." *Nature* 391 (6665) 339-40 (1998); Herreman, A., L et al. "Total inactivation of gamma-secretase activity in presenilin-deficient embryonic stem cells." Nat Cell Biol 2(7): 461-2 (2000)); point mutations of putative active site aspartate residues in PS trans-membrane domains inhibit β-amyloid production in cells in a dominant negative fashion (Wolfe, M. S. et al. "Two transmembrane aspartates in presenilin-1 required for presenilin endoproteolysis and gamma-secretase activity." *Nature* 398 (6727): 513-7 (1999); Kimberly, W. T. et al. "The transmembrane aspartates in presenilin 1 and 2 are obligatory for gamma-secretase activity and amyloid beta-protein generation." *J Biol Chem* 275(5): 3173-8 (2000)); active site directed substrate-based transition state isosteres designed to inhibit gamma secretase directly conjugate to PS (Esler, W. P., et al. "Transition-state analogue inhibitors of gamma-secretase bind directly to presenilin-1." *Nat Cell Biol* 2(7): 428-34 (2000); Li, Y. M., et al "Photoactivated gamma-secretase inhibitors directed to the active site covalently label presenilin 1." *Nature* 405(6787): 689-94 (2000).); finally, allosteric gamma secretase inhibitors have likewise been demonstrated to bind directly to PS (Seiffert, D., et al. "Presenilin-1 and -2 are molecular targets for gamma-secretase inhibitors" *J Biol Chem* 275 (44) 34086-91 (2000)).

Current evidence indicates that in addition to APP processing leading to β-amyloid synthesis, gamma-secretase also mediates the intra-membrane cleavage of other type I trans-membrane proteins (reviewed in Fortini, M. E. "Gamma-secretase-mediated proteolysis in cell-surface-receptor signaling." *Nat Rev Mol Cell Biol* 3 (9): 673-84 (2002), see also Struhl, G. et al. "Requirements for presenilin-dependent cleavage of notch and other transmembrane proteins." *Mol Cell* 6(3): 625-36. (2000).) Noteworthy among the known substrates of gamma-secretase is mammalian Notch 1. The Notch 1 protein is important for cell fate determination during development, and tissue homeostasis in the adult. Upon ligand engagement via the Notch ecto-domain, Notch undergoes sequential extra-cellular and intra-membrane processing analogous to APP. The intra-membrane processing of Notch mediated by gamma secretase leads to release of the Notch intracellular domain (NICD). The NICD fragment mediates Notch signaling via translocation to the nucleus, where it regulates expression of genes mediating cellular differentiation in many tissues during development, as well as in the adult.

Disruption of Notch signaling via genetic knock-out (KO) results in embryonic lethal phenotype in mice (Swiatek, P. J et al. "Notch1 is essential for postimplantation development in mice." *Genes Dev* 8 (6): 707-19 (1994) and Conlon, R. A et al. "Notch1 is required for the coordinate segmentation of somites" *Development* 121 (5): 1533-45 (1995)). The Notch KO phenotype is very similar to the phenotype observed PS1 KO mice, and precisely reproduced by PS1/PS2 double KO mice (De Strooper et al. "Deficiency of presenilin-1 inhibits the normal cleavage of amyloid precursor protein." *Nature* 391(6665): 387-90 (1998); Donoviel, D. B., et al. "Mice lacking both presenilin genes exhibit early embryonic patterning defects." *Genes Dev* 13(21): 2801-10 (1999); and Herreman, A., et al "Total inactivation of gamma-secretase activity in presenilin-deficient embryonic stem cells" *Nat Cell Biol* 2 (7): 461-2 (2000)).

Gamma-secretase inhibitors have also been shown to increase angiogenesis. See US 2006/0264380. As such, the gamma secretase inhibitors of the invention are useful in promoting angiogenesis.

Other studies have found that gamma-secretase inhibitors can prevent Notch activation and reduce proliferation in some human cancers. Konishi J, et al., Cancer Res. 2007 Sep. 1; 67(17):8051-7; Miele L, et al., Curr Cancer Drug Targets. 2006 June; 6(4):313-23, "NOTCH signaling as a novel cancer therapeutic target".

SUMMARY OF THE INVENTION

In a broad aspect, the invention provides compounds of Formula I:

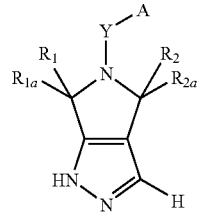

Formula I stereoisomers, tautomers, mixtures of stereoisomers and/or tautomers or pharmaceutically acceptable salts thereof, wherein A is $C_1$-$C_6$ alkyl, aryl, $C_3$-$C_6$ cycloalkyl, heteroaryl or heterocyclyl, wherein each ring is optionally substituted at a substitutable position with one or more of halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, hydroxyl, hydroxyalkyl, CN, aryloxy, arylalkyloxy, —$SO_2$—($C_1$-$C_6$ alkyl), —NR'R", $C_1$-$C_6$ alkanoyl, $C_0$-$C_3$alkyl-C(O)OR', heteroaryl, heterocyclyl, aryl, arylalkyl, aroyl, or —$SO_2$—NR'R", and wherein when A is $C_1$-$C_6$ alkyl, the $C_1$-$C_6$ alkyl group is optionally substituted at a substitutable position with one or more of halogen, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkoxy, hydroxyl, hydroxyalkyl, CN, aryloxy, arylalkyloxy, —$SO_2$—($C_1$-$C_6$ alkyl), —NR'R", $C_1$-$C_6$ alkanoyl, $C_0$-$C_3$alkyl-C(O)OR', heteroaryl, heterocyclyl, aryl, arylalkyl, aroyl, or —$SO_2$—NR'R", $R_1$, $R_{1a}$, $R_2$, and $R_{2a}$, are independently hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, $C_1$-$C_6$ haloalkyl, aryl, aryl$C_1$-$C_6$ alkyl, heteroaryl, heterocyclyl, —C(O)OR', —CONR'R", $C_1$-$C_4$ haloalkoxyalkyl, hydroxy $C_1$-$C_6$ alkyl, $C_1$-$C_6$ alkoxy, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, CN, or —$C_0$-$C_6$ alkyl-OC(O)-heterocyclyl, wherein each aryl, heteroaryl, and heterocyclyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, CN, or —C(O)OR'; or $R_1$ and $R_{1a}$, or $R_2$ and $R_{2a}$ together with the carbon to which they are attached form $C_3$-$C_6$ cycloalkyl group wherein one of the carbons is optionally replaced with a heteroatom selected from N, O or S and wherein said ring may be optionally substituted with $C_1$-$C_6$ alkyl; or $R_1$ and $R_{1a}$, or $R_2$ and $R_{2a}$ together with the carbon to which they are attached form an oxo group;

R' and R" are independently H or $C_1$-$C_6$ alkyl; or R' and R" together with the atom to which they are attached may form a 3-8 membered ring optionally including an additional heteroatom such as N, O or S;

Y is —$SO_2$— or —$SO_2$—O—. or $SO_2$-$NR_{10}$—; and $R_{10}$ is H or $C_1$-$C_6$ alkyl.

The compounds of Formula I inhibit β-amyloid peptide release and/or its synthesis and, therefore, are useful in the prevention of Alzheimer's Disease (AD) in patients susceptible to AD and/or in the treatment of patients with AD in order to inhibit further deterioration in their condition. The invention also encompasses pharmaceutical compositions containing the compounds of Formula I, and methods employing such compounds or compositions in the treatment of cognitive diseases, including Alzheimer's disease, including prodromal Alzheimer's disease.

The invention also provides a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, age related macular degeneration or diffuse Lewy body type of Alzheimer's disease and who is in need of such treatment which comprises administration of a therapeutically effective amount of a compound of Formula I.

The invention further provides a method of influencing a disease state in a cell, a group of cells, or an organism, comprising: administering at least one gamma-secretase inhibitor or a gamma-secretase pathway inhibitor of Formula I, or a pharmaceutically acceptable salt thereof, to the cell, group of cells, or organism, wherein the disease is selected from the group consisting of cancer, intraocular disorders (e.g. age related macular degeneration) and protein deposition-related diseases described above, Down's syndrome, Hereditary Cerebral Hemorrhage with Amyloidosis of the Dutch-Type, cerebral amyloid angiopathy, Parkinson's disease, progressive supranuclear palsy, dementia associated with cortical basal degeneration, age related macular degeneration and diffuse Lewy body type of Alzheimer's disease Still further, the invention provides a method of increasing the angiogenic process in a cell, a group of cells, or an organism, comprising administering a pharmaceutical composition comprising a pharmaceutically effective amount of at least one gamma-secretase inhibitor or gamma-secretase pathway inhibitor of Formula I, or a pharmaceutically acceptable salt thereof, to the cell, group of cells, or organism.

Further still, the invention provides a method of increasing the angiogenic process in a cell, a group of cells, or an organism, comprising administering a pharmaceutical composition comprising a pharmaceutically effective amount of at least one gamma-secretase inhibitor or gamma-secretase pathway inhibitor of Formula I, or a pharmaceutically acceptable salt thereof, to the cell, group of cells, or organism, wherein the pharmaceutical composition is administered to prevent, treat, or cure a condition treatable by increasing angiogenesis.

And still further the invention provides a method of treating cancer, including, but not limited to medulloblastoma with high levels of the Notch2 gene, colorectal cancers (treated with compounds of the invention alone, or in conjunction with taxanes), lung cancers, acute lymphoblastic leukemia and other hematologic cancers, Kaposi's sarcoma, breast cancer and melanoma.

The invention also provides a method for screening for a substance which initiates or increases angiogenesis, comprising: measuring an activity of a gamma-secretase pathway in the presence of a candidate compound in a suitable model; measuring an activity of a gamma-secretase pathway in the absence of a candidate compound; and comparing said activity in the presence of a candidate compound with said activity in the absence of the candidate compound, wherein a change in activity indicates that said candidate initiates or increases angiogenesis.

In another aspect, the invention provides methods of preparing the compounds of interest, as well as intermediates useful in preparing the compounds of interest.

DETAILED DESCRIPTION OF THE INVENTION

As described above, the invention provides compounds of Formula I.

In yet another aspect, the invention provides compounds of Formula 2, i.e., compounds of Formula I, wherein $R_1$ and $R_2$, are independently hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, $C_1$-$C_6$ haloalkyl, aryl, aryl$C_1$-$C_6$ alkyl, heteroaryl, heterocyclyl —C(O)OR', —CONR'R", $C_1$-$C_6$ haloalkyl, $C_1$-$C_4$ haloalkoxyalkyl, hydroxy $C_1$-$C_6$ alkyl, $C_1$-$C_6$ alkoxy, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, CN, or —$C_0$-$C_6$ alkyl-OC(O)-heterocyclyl, wherein each aryl, heteroaryl, and heterocyclyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, CN, or —C(O)OR'.

In yet another aspect, the invention provides compounds of Formula 3, i.e., compounds of Formula I, wherein $R_2$ is hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, $C_1$-$C_6$ haloalkyl, aryl, aryl$C_1$-$C_6$ alkyl, heteroaryl, heterocyclyl, —C(O)OR', —CONR'R", $C_1$-$C_6$ haloalkyl, $C_1$-$C_4$ haloalkoxyalkyl, hydroxy $C_1$-$C_6$ alkyl, $C_1$-$C_6$ alkoxy, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, CN, or —$C_0$-$C_6$ alkyl-OC(O)-heterocyclyl, wherein each aryl, heteroaryl, and heterocyclyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, CN, or —C(O)OR'; and $R_1$, $R_{1a}$ and $R_{2a}$ are independently H or $C_1$-$C_6$ alkyl.

In another aspect, the invention provides compounds of Formula 3a, i.e. compounds of Formula 3, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, and $R_{1a}$ and $R_{2a}$ are hydrogen.

In another aspect, the invention provides compounds of Formula 3b, i.e. compounds of Formula 3, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy; $R_1$ is hydrogen, $C_1$-$C_6$ alkyl, $C_3$-$C_6$cycloalkyl, $C_3$-$C_6$cycloalkylalkyl, halo $C_1$-$C_4$ alkyl, halo $C_1$-$C_4$ alkoxy, —C(O)NR'R", —NR'R", hydroxyl, hydroxy $C_1$-$C_4$ alkyl, CN, or —C(O)OR'; R' is $C_1$-$C_6$ alkyl; and $R_{1a}$ and $R_{2a}$ are hydrogen.

In another aspect, the invention provides compounds of Formula 3c, i.e. compounds of Formula 3, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is heteroaryl and $R_{1a}$ and $R_{2a}$ are hydrogen.

In another aspect, the invention provides compounds of Formula 4, i.e., compounds of Formula I, wherein A is naphthyl, which is optionally substituted at one or more substitutable positions with halogen, $C_1$-$C_6$ alkyl, $C_1$-$C_6$ alkoxy, $C_1$-$C_6$ haloalkyl, $C_1$-$C_6$ haloalkoxy, hydroxyl, hydroxyalkyl, CN, phenyloxy, benzyloxy, benzoyl, —SO$_2$—($C_1$-$C_6$ alkyl), —NR'R", $C_1$-$C_6$ alkanoyl, phenyl, benzyl, benzoyl or —SO$_2$—NR'R", where each R' and R" is independently H or $C_1$-$C_6$ alkyl.

In another aspect, the invention provides compounds of Formula 4A, i.e., compounds of Formula I having the formula:

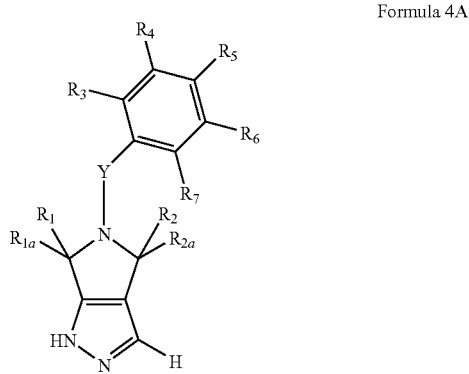

Formula 4A wherein,
$R_3$, $R_4$, $R_5$, $R_6$, and $R_7$ are independently H, halogen, $C_1$-$C_6$ alkyl, $C_1$-$C_6$ alkoxy, $C_1$-$C_6$ haloalkyl, $C_1$-$C_6$ haloalkoxy, hydroxyl, hydroxyalkyl, CN, aryloxy (e.g., phenyloxy), arylalkyloxy (e.g., benzyloxy), —SO$_2$—($C_1$-$C_6$ alkyl), —NR'R", $C_1$-$C_6$ alkanoyl, aryl (e.g., phenyl), arylalkyl (e.g. benzyl), aroyl (e.g., benzoyl), or —SO$_2$—NR'R", or
$R_3$ and $R_4$ and the carbons to which they are attached form a bicyclic aryl ring or a heteroaryl ring selected from the group of thienyl, furanyl, pyrrolyl, thiazolyl, oxazolyl, imidazolyl, isothiazolyl, isoxazolyl and imidazolyl, each of which is optionally substituted with 1, 2, or 3 groups that are independently $C_1$-$C_4$ alkyl, $C_1$-$C_4$ alkoxy, halogen, $C_1$-$C_4$ haloalkyl, or $C_1$-$C_4$ alkanoyl, wherein the alkanoyl group is optionally substituted with up to 3 halogen atoms; or
when $R_3$ and $R_4$ are not part of a ring, then $R_4$ and $R_5$ and the carbons to which they are attached may form a phenyl ring or a heteroaryl ring selected from the group of thienyl, furanyl, pyrrolyl, thiazolyl, oxazolyl, imidazolyl, isothiazolyl, isoxazolyl and imidazolyl, each of which is optionally substituted with 1, 2, or 3 groups that are independently $C_1$-$C_4$ alkyl, $C_1$-$C_4$ alkoxy, halogen, $C_1$-$C_4$ haloalkyl, or $C_1$-$C_4$ alkanoyl, wherein the alkanoyl group is optionally substituted with up to 3 halogen atoms; and
$R_1$, $R_{1a}$, $R_2$, and $R_{2a}$, are independently hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, aryl, aryl$C_1$-$C_6$ alkyl, heteroaryl, heterocyclyl, —C(O)OR', —CONR'R", $C_1$-$C_6$ haloalkyl, $C_1$-$C_6$ haloalkoxy, $C_1$-$C_4$ haloalkoxyalkyl, hydroxy $C_1$-$C_6$ alkyl, $C_1$-$C_6$ alkoxy, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, CN, or —$C_0$-$C_6$ alkyl-OC(O)-heterocyclyl, wherein each aryl, heteroaryl, and heterocyclyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo$C_1$-$C_4$ alkoxy, —C(O)NR'R", —NR'R", hydroxyl, CN, or —C(O)OR'; or $R_1$ and $R_{1a}$, or $R_2$ and $R_{2a}$ together with the carbon to which they are attached form $C_3$-$C_6$ cycloalkyl group wherein one of the carbons is optionally replaced with a heteroatom selected from N, O or S and wherein said ring may be optionally substituted with $C_1$-$C_6$ alkyl; or $R_1$ and $R_{1a}$, or $R_2$ and $R_{2a}$ together with the carbon to which they are attached form an oxo group; and R' and R" are independently H or $C_1$-$C_6$ alkyl; or R' and R" together with the atom to which they are attached form a 3-8 membered ring optionally including an additional heteroatom such as N, O or S.

In yet another aspect, the invention provides compounds of Formula 5, i.e., compounds of Formulas 4 or 4A, wherein $R_1$ is hydrogen, $C_1$-$C_6$ alkyl, $C_3$-$C_6$cycloalkyl, $C_3$-$C_6$cycloalkylalkyl, halo $C_1$-$C_4$ alkyl, halo $C_1$-$C_4$ alkoxy, —C(O)NR'R", —NR'R", hydroxyl, hydroxy $C_1$-$C_4$ alkyl, CN, or —C(O)OR', and $R_{1a}$ and $R_{2a}$ are both H.

In yet another aspect, the invention provides compounds of Formula 5a, i.e., compounds of Formulas 4 or 4A, wherein $R_1$ is heteroaryl. In one embodiment, $R_1$ is 1,2,4-oxadiazolyl; 1,3,4-oxadiazolyl; furanyl; pyridyl or thienyl; each of which is optionally substituted with one or more groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, CN, or —C(O)OR', where R' and R" are independently H or $C_1$-$C_6$ alkyl, or R' and R" together with the atom to which they are attached form a 3-6 membered ring.

In another aspect, the invention provides compounds of Formula 5b, i.e., compounds of Formula 5a, wherein $R_1$ is 1,2,4-oxadiazolyl; 1,3,4-oxadiazolyl; furanyl; pyridyl or thienyl; each of which is substituted with at least one group that is halogen, $C_1$-$C_4$ alkyl, $C_1$-$C_4$ alkoxy, $C_2$-$C_4$ alkanoyl, halo $C_1$-$C_4$ alkyl, halo $C_1$-$C_4$ alkoxy, —C(O)NR'R", —NR'R", hydroxyl, —C(O)OR', where R' and R" are independently H or $C_1$-$C_4$ alkyl.

In another aspect, the invention provides compounds of Formula 5c, i.e., compounds of Formula 5a, wherein $R_1$ is 1,2,4-oxadiazolyl; 1,3,4-oxadiazolyl; furanyl; pyridyl or thienyl; each of which is unsubstituted.

In yet another aspect, the invention provides compounds of Formula 5d, i.e., compounds of Formulas 4 or 4A, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$cycloalkyl, or $C_3$-$C_6$cycloalkyl$C_1$-$C_6$ alkyl; and $R_{1a}$ and $R_{2a}$ are both H.

In another aspect, the invention provides compounds of Formula 5e, i.e., compounds of Formulas 4 or 4A, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, or $C_3$-$C_6$ cycloalkyl, and $R_{1a}$ and $R_{2a}$ are both H.

In another aspect, the invention provides compounds of Formula 5f, i.e., compounds of Formulas 4 or 4A, wherein $R_1$ and $R_2$ are hydrogen, $C_1$-$C_4$ alkyl, $C_1$-$C_4$ haloalkyl, $C_1$-$C_4$ haloalkoxy, or $C_3$-$C_6$ cycloalkyl; and $R_{1a}$ and $R_{2a}$ are both H. In one embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is H. In another embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is methyl, ethyl, propyl, isopropyl or cyclopropyl. In still another embodiment, $R_1$ is methyl, ethyl, propyl, isopropyl or cyclopropyl and $R_2$ is hydrogen, $C_1$-$C_4$ alkyl, $C_1$-$C_4$ haloalkyl, $C_1$-$C_4$ haloalkoxy, or $C_3$-$C_6$cycloalkyl. In a further embodiment, $R_1$ and $R_2$ are both methyl, ethyl, isopropyl, or cyclopropyl. In a further embodiment, $R_1$ and $R_2$ are both ethyl. In a further embodiment, $R_1$ and $R_2$ are both cyclopropyl. $R_1$ and $R_2$ may be cis or trans relative to each other.

In yet another aspect, the invention provides compounds of Formula 6, i.e., compounds according to any one of Formulas 4, 4A, 5, 5a, 5b, 5c, 5d, or 5e, wherein $R_2$ is hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, phenyl, or phenyl$C_1$-$C_6$ alkyl, wherein each phenyl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R'', —NR'R'', hydroxyl, CN, or —C(O)OR'.

In yet another aspect, the invention provides compounds of Formula 6a, i.e., compounds according to any one of Formulas 4, 4A, 5, 5a, 5b, 5c, 5d, or 5e, wherein $R_2$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$cycloalkyl, or $C_3$-$C_6$cycloalkyl$C_1$-$C_6$ alkyl.

In yet another aspect, the invention provides compounds of Formula 6b, i.e., compounds according to any one of Formulas 4 or 4A, wherein $R_2$ is hydrogen, $C_1$-$C_4$ alkyl, $C_3$-$C_6$ cycloalkyl, $C_1$-$C_4$ haloalkyl, $C_1$-$C_4$ alkoxy, or $C_1$-$C_4$ haloalkoxy, and $R_1$, $R_{1a}$ and $R_{2a}$ are independently hydrogen or $C_1$-$C_6$ alkyl.

In yet another aspect, the invention provides compounds of Formula 6c, i.e., compounds according to any one of Formulas 4, 4A, 5, 5a, 5b, 5c, 5d, or 5e, wherein $R_2$ is hydrogen, $C_1$-$C_4$ alkyl, $C_1$-$C_4$ haloalkyl, or $C_3$-$C_6$cycloalkyl.

In another aspect, the invention provides compounds of Formula 6d, i.e., compounds of Formulas 4 or 4A, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is —C(O)OR', R' is $C_1$-$C_6$ alkyl and $R_{1a}$ and $R_{2a}$ are hydrogen.

In another aspect, the invention provides compounds of Formula 6e, i.e., compounds of Formulas 4, 4A, or 5a, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is heteroaryl and $R_{1a}$ and $R_{2a}$ are hydrogen.

In another aspect, the invention provides compounds of Formula 6f, i.e., compounds of Formulas 4, 4A, or 5a, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is 1,2,4-oxadiazolyl or 1,3,4-oxadiazolyl, and $R_{1a}$ and $R_{2a}$ are hydrogen.

In another aspect, the invention provides compounds of Formula 6g, i.e., compounds of Formulas 4, 4A, 5 or 5a, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is furanyl, pyridyl or thienyl, and $R_{1a}$ and $R_{2a}$ are hydrogen.

In another aspect, the invention provides compounds of Formula 7c, i.e., compounds of Formulas 4 or 4A, wherein $R_1$ and $R_2$ are both $C_1$-$C_2$ haloalkyl and $R_{1a}$ and $R_{2a}$ are both H. $R_1$ and $R_2$ may be cis or trans relative to each other. In one embodiment, $R_1$ and $R_2$ are —$CH_2F$, —$CH_2CF_3$, —$CH_2CHF_2$, $CF_3$, or —$CF_2CH_3$.

In yet still another aspect, the invention provides compounds of Formula 7d, i.e., compounds of Formulas 4 or 4A, where, $R_1$, $R_{1a}$ and $R_{2a}$ are hydrogen and $R_2$ is $C_3$, $C_4$, $C_5$, or $C_6$-cycloalkyl.

In yet another aspect, the invention provides compounds of Formula 7e, i.e., compounds of Formulas 4 or 4A, where, $R_{1a}$ and $R_{2a}$ are hydrogen and $R_1$ and $R_2$ are $C_3$, $C_4$, $C_5$, or $C_6$-cycloalkyl. In one embodiment, at least one of $R_1$ and $R_2$ is $C_3$-cycloalkyl. In another embodiment, $R_1$ and $R_2$ are $C_3$-cycloalkyl.

In yet another aspect, the invention provides compounds of Formula 7f, i.e., compounds of Formulas 4 or 4A, where, $R_{1a}$ and $R_{2a}$ are hydrogen, $R_1$ is methyl, ethyl, propyl or isopropyl, and $R_2$ is $C_3$, $C_4$, $C_5$, or $C_6$-cycloalkyl. In one embodiment $R^1$ is ethyl and $R_2$ is $C_3$, $C_4$, $C_5$, or $C_6$-cycloalkyl. In one embodiment, $R_2$ is $C_3$ cycloalkyl.

In another aspect, the invention provides compounds of Formula 7g, i.e., compounds of Formulas 4 or 4A, where, $R_{1a}$ and $R_{2a}$ are hydrogen, $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 7h, i.e., compounds of Formula 7g, wherein $R_2$ is $C_3$, $C_5$, or $C_6$ cycloalkyl. In one embodiment, $R_2$ is cyclopropyl.

In an aspect, the invention provides compounds of Formula 7I, i.e., compounds of Formula 7g, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 7j, i.e., compounds of Formula 7g, wherein $R_2$ is $C_1$-$C_4$ hydroxyalkyl. In one embodiment, $R_2$ is $CH_2OH$.

In an aspect, the invention provides compounds of Formula 7k, i.e., compounds of Formula 7g, wherein $R_2$ is H or $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 7l, i.e., compounds of Formulas 4 or 4A, wherein $R_{1a}$ and $R_{2a}$ are hydrogen and $R_1$ is $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 7m, i.e., compounds of Formula 7l, wherein $R_2$ is H.

In an aspect, the invention provides compounds of Formula 7n, i.e., compounds of Formula 7l, wherein $R_2$ is $C_3$, $C_5$, or $C_6$ cycloalkyl. In one embodiment, $R_2$ is cyclopropyl.

In an aspect, the invention provides compounds of Formula 7o, i.e., compounds of Formula 7l, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 7p, i.e., compounds of Formula 7l, wherein $R_2$ is $C_1$-$C_4$ hydroxyalkyl. In one embodiment, $R_2$ is $CH_2OH$.

In an aspect, the invention provides compounds of Formula 7q, i.e., compounds of Formulas 4 or 4A, wherein $R_{1a}$, $R_{2a}$, and $R_1$ are hydrogen In an aspect, the invention provides compounds of Formula 7r, i.e., compounds of Formula 7q, wherein $R_2$ is H.

In an aspect, the invention provides compounds of Formula 7s, i.e., compounds of Formula 7q, wherein $R_2$ is $C_3$, $C_5$, or $C_6$ cycloalkyl. In one embodiment, $R_2$ is cyclopropyl.

In an aspect, the invention provides compounds of Formula 7t, i.e., compounds of Formula 7q, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 7u, i.e., compounds of Formula 7q, wherein $R_2$ is $C_1$-$C_4$ hydroxyalkyl. In one embodiment, $R_2$ is $CH_2OH$.

In an aspect, the invention provides compounds of Formula 7v, i.e., compounds of Formulas 4 or 4A, wherein $R_{1a}$ and $R_{2a}$ are hydrogen and $R_1$ is $C_1$-$C_4$ hydroxyalkyl. In one embodiment, $R_1$ is $CH_2OH$.

In an aspect, the invention provides compounds of Formula 7w, i.e., compounds of Formula 7v, wherein $R_2$ is $C_1$-$C_4$ hydroxyalkyl. In one embodiment, $R_2$ is $CH_2OH$.

In an aspect, the invention provides compounds of Formula 7x, i.e., compounds of Formula 7v, wherein $R_2$ is $C_3$, $C_5$, or $C_6$ cycloalkyl. In one embodiment, $R_2$ is cyclopropyl.

In an aspect, the invention provides compounds of Formula 7y, i.e., compounds of Formula 7v, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 7z, i.e., compounds of Formulas 4 or 4A, wherein $R_{1a}$ and $R_{2a}$ are hydrogen and $R_1$ is $C_1$-$C_4$ haloalkyl. In one embodiment, $R_1$ is $CF_3$, $CH_2F$ or $CH_2Cl$. In another embodiment, $R_1$ is $CF_3$. In yet another embodiment, $R_1$ is $CH_2F$.

In an aspect, the invention provides compounds of Formula 7z1, i.e., compounds of Formula 7z, wherein $R_2$ is H.

In an aspect, the invention provides compounds of Formula 7z2, i.e., compounds of Formula 7z, wherein $R_2$ is $C_3$, $C_5$, or $C_6$ cycloalkyl. In one embodiment, $R_2$ is cyclopropyl.

In an aspect, the invention provides compounds of Formula 7z3, i.e., compounds of Formula 7z, wherein $R_2$ is $C_1$-$C_4$ haloalkyl. In one embodiment, $R_2$ is $CF_3$. In another embodiment, $R_2$ is $CH_2$—F or $CH_2$—Cl.

In another aspect, the invention provides compounds of Formula 7z4, i.e., compounds of Formulas 4 or 4A, where, $R_{1a}$ and $R_{2a}$ are hydrogen, $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 7z5, i.e., compounds of Formula 7z4, wherein $R_1$ is $C_3$, $C_5$, or $C_6$ cycloalkyl. In one embodiment, $R_1$ is cyclopropyl.

In an aspect, the invention provides compounds of Formula 7z6, i.e., compounds of Formula 7z4, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 7z7, i.e., compounds of Formula 7z4, wherein $R_1$ is $C_1$-$C_4$ hydroxyalkyl. In one embodiment, $R_1$ is $CH_2OH$.

In an aspect, the invention provides compounds of Formula 7z8, i.e., compounds of Formula 7z4, wherein $R_1$ is H or $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 7z9, i.e., compounds of Formulas 4 or 4A, wherein $R_{1a}$ and $R_{2a}$ are hydrogen and $R_2$ is $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 7z10, i.e., compounds of Formula 7z9, wherein $R_1$ is H.

In an aspect, the invention provides compounds of Formula 7z11, i.e., compounds of Formula 7z9, wherein $R_1$ is $C_3$, $C_5$, or $C_6$ cycloalkyl. In one embodiment, $R_1$ is cyclopropyl.

In an aspect, the invention provides compounds of Formula 7z12, i.e., compounds of Formula 7z9, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 7z13, i.e., compounds of Formula 7z9, wherein $R_1$ is $C_1$-$C_4$ hydroxyalkyl. In one embodiment, $R_1$ is $CH_2OH$.

In an aspect, the invention provides compounds of Formula 7z14, i.e., compounds of Formulas 4 or 4A, wherein $R_{1a}$, $R_{2a}$, and $R_2$ are hydrogen In an aspect, the invention provides compounds of Formula 7z15, i.e., compounds of Formula 7z14, wherein $R_1$ is $C_3$, $C_5$, or $C_6$ cycloalkyl. In one embodiment, $R_1$ is cyclopropyl.

In an aspect, the invention provides compounds of Formula 7z16, i.e., compounds of Formula 7z14, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 7z17, i.e., compounds of Formula 7z14, wherein $R_1$ is $C_1$-$C_4$ hydroxyalkyl. In one embodiment, $R_1$ is $CH_2OH$.

In an aspect, the invention provides compounds of Formula 7z18, i.e., compounds of Formulas 4 or 4A, wherein $R_{1a}$ and $R_{2a}$ are hydrogen and $R_2$ is $C_1$-$C_4$ hydroxyalkyl. In one embodiment, $R_2$ is $CH_2OH$.

In an aspect, the invention provides compounds of Formula 7z19, i.e., compounds of Formula 7z18, wherein $R_1$ is $C_1$-$C_4$ hydroxyalkyl. In one embodiment, $R_1$ is $CH_2OH$.

In an aspect, the invention provides compounds of Formula 7z20, i.e., compounds of Formula 7z18, wherein $R_1$ is $C_3$, $C_5$, or $C_6$ cycloalkyl. In one embodiment, $R_1$ is cyclopropyl.

In an aspect, the invention provides compounds of Formula 7z21, i.e., compounds of Formula 7z18, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 7z22, i.e., compounds of Formulas 4 or 4A, wherein $R_{1a}$ and $R_{2a}$ are hydrogen and $R_2$ is $C_1$-$C_4$ haloalkyl. In one embodiment, $R_2$ is $CF_3$, $CH_2F$ or $CH_2Cl$. In another embodiment, $R_2$ is $CF_3$. In yet another embodiment, $R_2$ is $CH_2F$.

In an aspect, the invention provides compounds of Formula 7z23, i.e., compounds of Formula 7z22, wherein $R_1$ is H.

In an aspect, the invention provides compounds of Formula 7z24, i.e., compounds of Formula 7z22, wherein $R_1$ is $C_3$, $C_5$, or $C_6$ cycloalkyl. In one embodiment, $R_1$ is cyclopropyl.

In an aspect, the invention provides compounds of Formula 7z25, i.e., compounds of Formula 7z22, wherein $R_1$ is $C_1$-$C_4$ haloalkyl. In one embodiment, $R_1$ is $CF_3$. In another embodiment, $R_1$ is $CH_2$—F or $CH_2$—Cl.

In yet still another aspect, the invention provides compounds of Formula 8, i.e., compounds of Formulas 4 or 4A, wherein $R_2$ and $R_{2a}$ combine to form oxo or $C_3$-$C_6$ cycloalkyl.

In still another aspect, the invention provides compounds of Formula 8a, i.e., compounds of Formula 8 where, $R_1$ is H, $C_1$-$C_4$ alkyl, or $C_3$-$C_6$ cycloalkyl, and $R_{1a}$ is H.

In still another aspect, the invention provides compounds of Formula 8b, i.e., compounds of Formulas 8 or 8a where, $R_1$ is H, methyl, ethyl or isopropyl. In one embodiment, $R_1$ is H. In another embodiment, $R_1$ is methyl or ethyl.

In yet another aspect, the invention provides compounds of Formula 8c, i.e., compounds of Formulas 8 or 8a, where $R_1$ is $C_3$, $C_4$, $C_5$, or $C_6$ cyclolakyl. In one embodiment, $R_1$ is $C_3$-cycloalkyl.

In yet another aspect, the invention provides compounds of Formula 8d, i.e., compounds of Formulas 4 or 4A, wherein $R_2$ and $R_{2a}$ combine to form oxo, and $R_1$ and $R_{1a}$ are hydrogen.

In another aspect, the invention provides compounds of Formula 8e, i.e., compounds of Formulas 4 or 4A, wherein $R_2$ and $R_{2a}$ combine to form cyclopropyl, and $R_1$ and $R_{1a}$ are hydrogen.

In one aspect, the invention provides compounds of Formula 8f, i.e., compounds of Formulas 4 or 4A, wherein $R_2$ and $R_{2a}$ combine to form oxo, and $R_{1a}$ is hydrogen.

In another aspect, the invention provides compounds of Formula 8g, i.e., compounds of Formula 8f, wherein $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 8h, i.e., compounds of Formula 8f, wherein $R_1$ is $C_1$-$C_4$ hydroxyalkyl. In one embodiment, $R_1$ is $CH_2OH$.

In another aspect, the invention provides compounds of Formula 8i, i.e., compounds of Formula 8f, wherein $R_1$ is $C_1$-$C_4$ haloalkyl. In one embodiment, $R_1$ is $CH_2F$ or $CH_2Cl$.

In yet still another aspect, the invention provides compounds of Formula 8j, i.e., compounds of Formulas 4 or 4A, wherein $R_1$ and $R_{1a}$ combine to form oxo or $C_3$-$C_6$ cycloalkyl.

In still another aspect, the invention provides compounds of Formula 8k, i.e., compounds of Formula 8j where, $R_2$ is H, $C_1$-$C_4$ alkyl, or $C_3$-$C_6$ cycloalkyl, and $R_{2a}$ is H.

In still another aspect, the invention provides compounds of Formula 8l, i.e., compounds of Formulas 8j or 8k, where $R_2$ is H, methyl, ethyl or isopropyl. In one embodiment, $R_2$ is H. In another embodiment, $R_2$ is methyl or ethyl.

In yet another aspect, the invention provides compounds of Formula 8m, i.e., compounds of Formulas 8j or 8k, where $R_2$ is $C_3$, $C_4$, $C_5$, or $C_6$ cyclolakyl. In one embodiment, $R_2$ is $C_3$-cycloalkyl.

In yet another aspect, the invention provides compounds of Formula 8n, i.e., compounds of Formulas 4 or 4A, wherein $R_1$ and $R_{1a}$ combine to form oxo, and $R_2$ and $R_{2a}$ are hydrogen.

In yet another aspect, the invention provides compounds of Formula 8o, i.e., compounds of Formulas 4 or 4A, wherein $R_1$ and $R_{1a}$ combine to form cyclopropyl, and $R_2$ and $R_{2a}$ are hydrogen.

In one aspect, the invention provides compounds of Formula 8p, i.e., compounds of Formulas 4 or 4A, wherein $R_1$ and $R_{1a}$ combine to form oxo, and $R_{2a}$ is hydrogen.

In another aspect, the invention provides compounds of Formula 8q, i.e., compounds of Formula 8p, wherein $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 8r, i.e., compounds of Formula 8p, wherein $R_2$ is $C_1$-$C_4$ hydroxyalkyl. In one embodiment, $R_2$ is $CH_2OH$.

In another aspect, the invention provides compounds of Formula 8s, i.e., compounds of Formula 8p, wherein $R_2$ is $C_1$-$C_4$ haloalkyl. In one embodiment, $R_2$ is $CH_2F$ or $CH_2Cl$.

In still yet another aspect, the invention provides compounds of Formula 9, i.e., compounds according to any one of Formulas 4A up to and including 8s, wherein $R_3$, $R_4$, $R_5$, $R_6$, and $R_7$ are independently of each other hydrogen, halogen, $C_1$-$C_4$ alkyl, halo$C_1$-$C_4$alkyl, $C_1$-$C_4$ alkoxy, or halo$C_1$-$C_4$ alkoxy.

In still yet another aspect, the invention provides compounds of Formula 9a, i.e., compounds of Formula 9, wherein $R_3$, $R_4$, $R_5$, $R_6$, and $R_7$ are independently of each other methyl, ethyl, propyl or isopropyl.

In still yet another aspect, the invention provides compounds of Formula 9b, i.e., compounds of Formula 9, wherein $R_3$, $R_4$, $R_5$, $R_6$, and $R_7$ are independently of each other H, Cl, F, $CF_3$, $CHF_2$ methoxy, $OCF_3$, or $OCHF_2$.

In still yet another aspect, the invention provides compounds of Formula 9c, i.e., compounds of Formula 9, wherein $R_5$ is methyl, ethyl, propyl or isopropyl. In one embodiment, $R_3$, $R_4$, $R_6$, and $R_7$ are also independently of each other H, Cl, F, $CF_3$, $CHF_2$ methoxy, $OCF_3$, or $OCHF_2$.

In still yet another aspect, the invention provides compounds of Formula 9d, i.e., compounds of Formula 9, wherein $R_5$ is H, Cl, F, $CF_3$, $CHF_2$ methoxy, $OCF_3$, or $OCHF_2$.

In still yet another aspect, the invention provides compounds of Formula 9e, i.e., compounds of Formula 9 wherein $R_5$ is chloro. In one embodiment, $R_3$, $R_4$, $R_6$, and $R_7$ are also independently of each other H, Cl, F, $CF_3$, $CHF_2$ methoxy, $OCF_3$, or $OCHF_2$.

In still yet another aspect, the invention provides compounds of Formula 9f, i.e., compounds of Formula 9, wherein $R_5$ is fluoro. In one embodiment, $R_3$, $R_4$, $R_6$, and $R_7$ are also independently of each other H, Cl, F, $CF_3$, $CHF_2$ methoxy, $OCF_3$, or $OCHF_2$.

In still yet another aspect, the invention provides compounds of Formula 9g, i.e., compounds of Formula 9, wherein $R_5$ is $CF_3$. In one embodiment, $R_3$, $R_4$, $R_6$, and $R_7$ are also independently of each other H, Cl, F, $CF_3$, $CHF_2$ methoxy, $OCF_3$, or $OCHF_2$.

In still yet another aspect, the invention provides compounds of Formula 9h, i.e., compounds of Formula 9, wherein $R_5$ is $OCF_3$. In one embodiment, $R_3$, $R_4$, $R_6$, and $R_7$ are also independently of each other H, Cl, F, $CF_3$, $CHF_2$ methoxy, $OCF_3$, or $OCHF_2$.

In still yet another aspect, the invention provides compounds of Formula 9h1, i.e., compounds according to any one of Formulas 4A up to and including 8s, wherein $R_3$, $R_4$, $R_5$, $R_6$, and $R_7$ are independently of each other hydrogen, halogen, $C_1$-$C_2$alkyl, halo$C_1$-$C_2$alkyl, $C_1$-$C_2$ alkoxy, halo$C_1$-$C_2$ alkoxy, phenyloxy, benzyloxy, —$SO_2$—($C_1$-$C_4$ alkyl), —NR'R", $C_1$-$C_6$ alkanoyl, phenyl, benzyl, or benzoyl. In one embodiment, one of $R_3$, $R_4$, $R_5$, $R_6$, and $R_7$ is phenyloxy, benzyloxy, —$SO_2$—($C_1$-$C_4$ alkyl), —NR'R", $C_1$-$C_4$ alkanoyl, phenyl, benzyl, or benzoyl. In another embodiment, one of $R_3$, $R_4$, $R_5$, $R_6$, and $R_7$ is phenyloxy, benzyloxy, —$SO_2$—($C_1$-$C_4$ alkyl), —NR'R", $C_1$-$C_4$ alkanoyl, phenyl, benzyl, or benzoyl, while the other variables are H.

In still yet another aspect, the invention provides compounds of Formula 9i, i.e., compounds of Formulas 9, 9a, 9b, 9c, 9d, 9e, 9f, 9g, 9h, or 9h1 wherein $R_3$, $R_4$, $R_6$ and $R_7$ are H.

In yet another aspect, the invention provides compounds of Formula 9j, i.e., compounds according to any one of Formulas 4A up to and including 8s, wherein $R_3$ and $R_4$ and the carbons to which they are attached form a phenyl ring, which is optionally substituted with 1, 2, or 3 groups that are independently $C_1$-$C_4$ alkyl, $C_1$-$C_4$ alkoxy, halogen, $C_1$-$C_4$ haloalkyl, or $C_1$-$C_4$ alkanoyl, wherein the alkanoyl group is optionally substituted with up to 3 halogen atoms. In one embodiment, the phenyl ring is unsubstituted.

In yet still another aspect, the invention provides compounds of Formula 9k, i.e., compounds according to any one of Formulas 4A up to and including 8s, wherein $R_3$ and $R_4$ and the carbons to which they are attached form a heteroaryl ring that is selected from the group of thienyl, furanyl, pyrrolyl, thiazolyl, oxazolyl, imidazolyl, isothiazolyl, isoxazolyl and imidazolyl, each of which is optionally substituted with 1, 2, or 3 groups that are independently $C_1$-$C_4$ alkyl, $C_1$-$C_4$ alkoxy, halogen, $C_1$-$C_4$ haloalkyl, or $C_2$-$C_4$ alkanoyl, wherein the alkanoyl group is optionally substituted with up to 3 halogen atoms.

In another aspect, the invention provides compounds of Formula 9l, i.e., compounds according to any one of Formulas 4A up to and including 8s, wherein $R_3$ and $R_4$ and the carbons to which they are attached form a heteroaryl ring that is selected from the group of thienyl, furanyl, pyrrolyl, thiazolyl, oxazolyl, imidazolyl, isothiazolyl, isoxazolyl and imidazolyl, each of which substituted with 1 or 2 groups that are independently $C_1$-$C_4$ alkyl, $C_1$-$C_4$ alkoxy, halogen, $C_1$-$C_2$ haloalkyl, or $C_2$-$C_4$ alkanoyl, wherein the alkanoyl group is optionally substituted with up to 3 halogen atoms.

In another aspect, the invention provides compounds of Formula 9m, i.e., compounds of Formula 9l, wherein $R_3$ and $R_4$ and the carbons to which they are attached form a heteroaryl ring that is selected from the group of thienyl, furanyl, and pyrrolyl.

In another aspect, the invention provides compounds of Formula 9n, i.e., compounds of Formula 9l, wherein $R_3$ and $R_4$ and the carbons to which they are attached form a heteroaryl ring that is selected from the group of thiazolyl, oxazolyl, imidazolyl, isothiazolyl, isoxazolyl and imidazolyl.

In another aspect, the invention provides compounds of Formula 9o, i.e., compounds of Formulas 9j, 9k, 9l, 9m or 9n, wherein $R_6$ and $R_7$ are H.

In one aspect, the invention provides compounds of Formula 9p, i.e., compounds of Formula 9o, wherein $R_5$ is F, Cl, $CF_3$, or H. In one embodiment, $R_5$ is H.

In one aspect, the invention provides compounds of Formula 9q, i.e., compounds according to any one of Formulas 4 up to and including 8s, wherein when $R_3$ and $R_4$ and the carbons to which they are attached do not form a ring, then $R_4$ and $R_5$ and the carbons to which they are attached may form a phenyl ring or a heteroaryl ring selected from the group of thienyl, furanyl, pyrrolyl, thiazolyl, oxazolyl, imidazolyl, isothiazolyl, isoxazolyl and imidazolyl, each of which is optionally substituted with 1, 2, or 3 groups that are independently $C_1$-$C_4$ alkyl, $C_1$-$C_4$ alkoxy, halogen, $C_1$-$C_2$ haloalkyl, or $C_2$-$C_4$ alkanoyl, wherein the alkanoyl group is optionally substituted with up to 3 halogen atoms.

In one aspect, the invention provides compounds of Formula 9r, i.e., compounds of Formula 9q, wherein $R_4$ and $R_5$ and the carbons to which they are attached form a phenyl ring, which is optionally substituted with 1, 2, or 3 groups that are independently $C_1$-$C_4$ alkyl, $C_1$-$C_4$ alkoxy, halogen, $C_1$-$C_2$ haloalkyl (e.g., $CF_3$ or $CH_2F$), or $C_2$-$C_4$ alkanoyl, wherein the alkanoyl group is optionally substituted with up to 3 halogen atoms. In one embodiment, the phenyl ring is unsubstituted.

In one aspect, the invention provides compounds of Formula 9s, i.e., compounds of Formula 9q, wherein $R_4$ and $R_5$ and the carbons to which they are attached form a heteroaryl selected from the group of thienyl, furanyl, and pyrrolyl, each of which is optionally substituted with 1, 2, or 3 groups that are independently $C_1$-$C_4$ alkyl, $C_1$-$C_4$ alkoxy, halogen, $C_1$-$C_2$ haloalkyl, or $C_2$-$C_4$ alkanoyl, wherein the alkanoyl group is optionally substituted with up to 3 halogen atoms. In one embodiment the heteroaryl group is unsubstituted.

In one aspect, the invention provides compounds of Formula 9t, i.e., compounds of Formula 9q, wherein $R_4$ and $R_5$ and the carbons to which they are attached form a heteroaryl ring selected from the group of thiazolyl, oxazolyl, imidazolyl, isothiazolyl, isoxazolyl and imidazolyl, each of which is optionally substituted with 1, 2, or 3 groups that are independently $C_1$-$C_4$ alkyl, $C_1$-$C_4$ alkoxy, halogen, $C_1$-$C_2$ haloalkyl, or $C_2$-$C_4$ alkanoyl, wherein the alkanoyl group is optionally substituted with up to 3 halogen atoms. In one embodiment the heteroaryl group is unsubstituted.

In one aspect, the invention provides compounds of Formula 9u, i.e., compounds according to any one of Formulas 4A to 9t, having the formula:

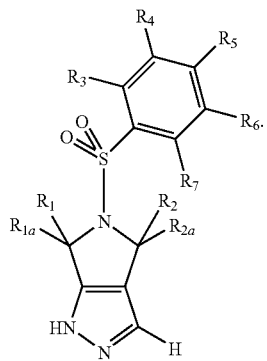

In one aspect, the invention provides compounds of Formula 9v, i.e., compounds according to any one of Formulas 4A to 9t, having the formula:

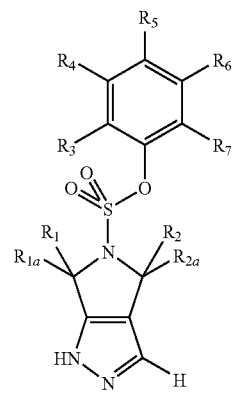

In one aspect, the invention provides compounds of Formula 9w, i.e., compounds according to any one of Formulas 4A to 9t, having the formula:

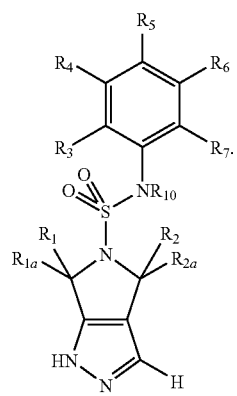

In one aspect, the invention provides compounds of Formula 9x, i.e., compounds of Formula 9w, wherein $R_{10}$ is $C_1$-$C_4$ alkyl or H. In one embodiment, $R_{10}$ is methyl. In another embodiment, $R_{10}$ is hydrogen.

In still another aspect, the invention provides compounds of Formula 10, i.e., compounds of Formula I having the following formula:

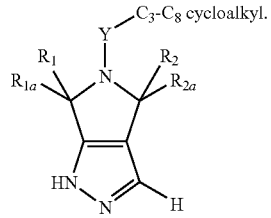

Formula 10 wherein, the $C_3$-$C_8$ cycloalkyl group is optionally substituted at a substitutable position with halogen, $C_1$-$C_6$ alkyl, $C_1$-$C_6$ alkoxy, haloalkyl, haloalkoxy, hydroxyl, CN, aryloxy (e.g., phenyloxy), benzyloxy, —$SO_2$—($C_1$-$C_6$ alkyl), —NR'R", $C_1$-$C_6$ alkanoyl, pyridyl, phenyl, or —$SO_2$—NR'R";

$R_1$, $R_{1a}$, $R_2$, and $R_{2a}$, are independently hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, $C_1$-$C_6$ haloalkyl, aryl, aryl$C_1$-$C_6$ alkyl, heteroaryl, heterocyclyl, —C(O)OR', —CONR'R", $C_1$-$C_6$ haloalkyl, $C_1$-$C_4$ haloalkoxyalkyl, hydroxy $C_1$-$C_6$ alkyl, $C_1$-$C_6$ alkoxy, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, CN, or —$C_0$-$C_6$ alkyl-OC(O)-heterocyclyl, wherein each aryl, heteroaryl, and heterocyclyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo$C_1$-$C_4$ alkoxy, —C(O)NR'R", —NR'R", hydroxyl, CN, or —C(O)OR'; or $R_1$ and $R_{1a}$, or $R_2$ and $R_{2a}$ together with the carbon to which they are attached form $C_3$-$C_6$ cycloalkyl group wherein one of the carbons is optionally replaced with a heteroatom selected from N, O or S and wherein said ring may be optionally substituted with $C_1$-$C_6$ alkyl; or $R_1$ and $R_{1a}$, or $R_2$ and $R_{2a}$ together with the carbon to which they are attached form an oxo group; and R' and R" are independently H or $C_1$-$C_6$ alkyl; or R' and R" together with the atom to which they are attached may form a 3-8 membered ring optionally including an additional heteroatom such as N, O or S.

In yet another aspect, the invention provides compounds of Formula 11, i.e., compounds of Formula 10, wherein $R_1$ is hydrogen, $C_1$-$C_6$ alkyl, $C_3$-$C_6$cycloalkyl, $C_3$-$C_6$cycloalkylalkyl, halo $C_1$-$C_4$ alkyl, halo $C_1$-$C_4$ alkoxy, —C(O)NR'R", —NR'R", hydroxyl, hydroxy $C_1$-$C_4$ alkyl, CN, or —C(O)OR', and $R_{1a}$ and $R_{2a}$ are both H.

In yet another aspect, the invention provides compounds of Formula 11a, i.e., compounds of Formula 10, wherein $R_1$ is heteroaryl. In one embodiment, $R_1$ is 1,2,4-oxadiazolyl; 1,3,4-oxadiazolyl; furanyl; pyridyl or thienyl; each of which is optionally substituted with one or more groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, CN, or —C(O)OR', where R' and R" are independently H or $C_1$-$C_6$ alkyl, or R' and R" together with the atom to which they are attached form a 3-6 membered ring.

In another aspect, the invention provides compounds of Formula 11b, i.e., compounds of Formula 10, wherein $R_1$ is 1,2,4-oxadiazolyl; 1,3,4-oxadiazolyl; furanyl; pyridyl or thienyl; each of which is substituted with at least one group that is halogen, $C_1$-$C_4$ alkyl, $C_1$-$C_4$ alkoxy, $C_2$-$C_4$ alkanoyl, halo $C_1$-$C_4$ alkyl, halo $C_1$-$C_4$ alkoxy, —C(O)NR'R", —NR'R", hydroxyl, —C(O)OR', where R' and R" are independently H or $C_1$-$C_4$ alkyl.

In another aspect, the invention provides compounds of Formula 11c, i.e., compounds of Formula 10, wherein $R_1$ is 1,2,4-oxadiazolyl; 1,3,4-oxadiazolyl; furanyl; pyridyl or thienyl; each of which is unsubstituted.

In yet another aspect, the invention provides compounds of Formula 11d, i.e., compounds of Formula 10, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$cycloalkyl, or $C_3$-$C_6$cycloalkyl$C_1$-$C_6$ alkyl; and $R_{1a}$ and $R_{2a}$ are both H.

In another aspect, the invention provides compounds of Formula 11e, i.e., compounds of Formula 10, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, or $C_3$-$C_6$ cycloalkyl, and $R_{1a}$ and $R_{2a}$ are both H.

In another aspect, the invention provides compounds of Formula 11f, i.e., compounds of Formula 10, wherein $R_1$ and $R_2$ are hydrogen, $C_1$-$C_4$ alkyl, $C_1$-$C_4$ haloalkyl, $C_1$-$C_4$ haloalkoxy, or $C_3$-$C_6$ cycloalkyl; and $R_{1a}$ and $R_{2a}$ are both H. In one embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is H. In another embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is methyl, ethyl, propyl, isopropyl or cyclopropyl. In still another embodiment, $R_1$ is methyl, ethyl, propyl, isopropyl or cyclopropyl and $R_2$ is hydrogen, $C_1$-$C_4$ alkyl, $C_1$-$C_4$ haloalkyl, $C_1$-$C_4$ haloalkoxy, or $C_3$-$C_6$cycloalkyl. In a further embodiment, $R_1$ and $R_2$ are both methyl, ethyl, isopropyl, or cyclopropyl. In a further embodiment, $R_1$ and $R_2$ are both ethyl. In a further embodiment, $R_1$ and $R_2$ are both cyclopropyl. $R_1$ and $R_2$ may be cis or trans relative to each other.

In yet another aspect, the invention provides compounds of Formula 12, i.e., compounds according to any one of Formulas 10, 11, 11a, 11b, 11c, 11d, or 11e, wherein $R_2$ is hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, phenyl, phenyl$C_1$-$C_6$ alkyl, wherein each phenyl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, CN, or —C(O)OR'.

In yet another aspect, the invention provides compounds of Formula 12a, i.e., compounds according to any one of Formulas 10, 11, 11a, 11b, 11c, 11d, or 11e, wherein $R_2$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$cycloalkyl, or $C_3$-$C_6$cycloalkyl$C_1$-$C_6$ alkyl.

In yet another aspect, the invention provides compounds of Formula 12b, i.e., compounds according to any one of Formulas 10, 11, 11a, 11b, 11c, 11d, or 11e, wherein $R_2$ is hydrogen, $C_1$-$C_4$ alkyl, $C_3$-$C_6$ cycloalkyl, $C_1$-$C_4$ haloalkyl, $C_1$-$C_4$ alkoxy, or $C_1$-$C_4$ haloalkoxy, and $R_{1a}$ and $R_{2a}$ are independently hydrogen or $C_1$-$C_6$ alkyl.

In yet another aspect, the invention provides compounds of Formula 12c, i.e., compounds according to any one of Formulas 10, 11, 11a, 11b, 11c, 11d, or 11e, wherein $R_2$ is hydrogen, $C_1$-$C_4$ alkyl, $C_1$-$C_4$ haloalkyl, or $C_3$-$C_6$cycloalkyl.

In another aspect, the invention provides compounds of Formula 12d, i.e. compounds according to Formula 10, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is —C(O)OR', R' is $C_1$-$C_6$ alkyl and $R_{1a}$ and $R_{2a}$ are hydrogen.

In another aspect, the invention provides compounds of Formula 12e, i.e. compounds of Formula 10, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is heteroaryl and $R_{1a}$ and $R_{2a}$ are hydrogen.

In another aspect, the invention provides compounds of Formula 12f, i.e., compounds of Formulas 10 or 11a, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is 1,2,4-oxadiazolyl or 1,3,4-oxadiazolyl, and $R_{1a}$ and $R_{2a}$ are hydrogen.

In another aspect, the invention provides compounds of Formula 12g, i.e., compounds of Formulas 10 or 11a, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is furanyl, pyridyl or thienyl, and $R_{1a}$ and $R_{2a}$ are hydrogen.

In another aspect, the invention provides compounds of Formula 13c, i.e., compounds of Formula 10, wherein $R_1$ and $R_2$ are both $C_1$-$C_2$ haloalkyl and $R_{1a}$ and $R_{2a}$ are both H. $R_1$ and $R_2$ may be cis or trans relative to each other. In one embodiment, $R_1$ and $R_2$ are —$CH_2F$, —$CH_2CF_3$, —$CH_2CHF_2$, $CF_3$, or —$CF_2CH_3$.

In yet still another aspect, the invention provides compounds of Formula 13d, i.e., compounds of Formula 10, wherein, $R_1$, $R_{1a}$ and $R_{2a}$ are hydrogen and $R_2$ is $C_3$, $C_4$, $C_5$, or $C_6$-cycloalkyl.

In yet another aspect, the invention provides compounds of Formula 13e, i.e., compounds of Formula 10 wherein, $R_{1a}$ and $R_{2a}$ are hydrogen and $R_1$ and $R_2$ are $C_3$, $C_4$, $C_5$, or $C_6$ cycloalkyl. In one embodiment one of $R_1$ and $R_2$ is $C_3$-cycloalkyl. In another embodiment, $R_1$ and $R_2$ are $C_3$-cycloalkyl.

In yet another aspect, the invention provides compounds of Formula 13f, i.e., compounds of Formula 10 wherein, where, $R_{1a}$ and $R_{2a}$ are hydrogen, $R_1$ is methyl, ethyl, propyl or isopropyl, and $R_2$ is $C_3$, $C_4$, $C_5$, or $C_6$-cycloalkyl. In one embodiment $R_1$ is ethyl and $R_2$ is $C_3$, $C_4$, $C_5$, or $C_6$-cycloalkyl. In one embodiment, $R_2$ is $C_3$-cycloalkyl.

In another aspect, the invention provides compounds of Formula 13g, i.e., compounds of Formula 10, where, $R_{1a}$ and $R_{2a}$ are hydrogen, $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 13h, i.e., compounds of Formula 13g, wherein $R_2$ is $C_3$, $C_5$, or $C_6$ cycloalkyl. In one embodiment, $R_2$ is cyclopropyl.

In an aspect, the invention provides compounds of Formula 13i, i.e., compounds of Formula 13g, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 13j, i.e., compounds of Formula 13g, wherein $R_2$ is $C_1$-$C_4$ hydroxyalkyl. In one embodiment, $R_2$ is $CH_2OH$.

In an aspect, the invention provides compounds of Formula 13k, i.e., compounds of Formula 13g, wherein $R_2$ is H or $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 13l, i.e., compounds of Formula 10, wherein $R_{1a}$ and $R_{2a}$ are hydrogen and $R_1$ is $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 13m, i.e., compounds of Formula 13l, wherein $R_2$ is H.

In an aspect, the invention provides compounds of Formula 13n, i.e., compounds of Formula 13l, wherein $R_2$ is $C_3$, $C_5$, or $C_6$ cycloalkyl. In one embodiment, $R_2$ is cyclopropyl.

In an aspect, the invention provides compounds of Formula 13o, i.e., compounds of Formula 13l, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 13p, i.e., compounds of Formula 13l, wherein $R_2$ is $C_1$-$C_4$ hydroxyalkyl. In one embodiment, $R_2$ is $CH_2OH$.

In an aspect, the invention provides compounds of Formula 13q, i.e., compounds of Formula 10, wherein $R_{1a}$, $R_{2a}$, and $R_1$ are hydrogen In an aspect, the invention provides compounds of Formula 13r, i.e., compounds of Formula 13q, wherein $R_2$ is H.

In an aspect, the invention provides compounds of Formula 13s, i.e., compounds of Formula 13q, wherein $R_2$ is $C_3$, $C_5$, or $C_6$ cycloalkyl. In one embodiment, $R_2$ is cyclopropyl.

In an aspect, the invention provides compounds of Formula 13t, i.e., compounds of Formula 13q, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 13u, i.e., compounds of Formula 13q, wherein $R_2$ is $C_1$-$C_4$ hydroxyalkyl. In one embodiment, $R_2$ is $CH_2OH$.

In an aspect, the invention provides compounds of Formula 13v, i.e., compounds of Formula 10, wherein $R_{1a}$ and $R_{2a}$ are hydrogen and $R_1$ is $C_1$-$C_4$ hydroxyalkyl. In one embodiment, $R_1$ is $CH_2OH$.

In an aspect, the invention provides compounds of Formula 13w, i.e., compounds of Formula 13v, wherein $R_2$ is $C_1$-$C_4$ hydroxyalkyl. In one embodiment, $R_2$ is $CH_2OH$.

In an aspect, the invention provides compounds of Formula 13x, i.e., compounds of Formula 13v, wherein $R_2$ is $C_3$, $C_5$, or $C_6$ cycloalkyl. In one embodiment, $R_2$ is cyclopropyl.

In an aspect, the invention provides compounds of Formula 13y, i.e., compounds of Formula 13v, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 13z, i.e., compounds of Formula 10, wherein $R_{1a}$ and $R_{2a}$ are hydrogen and $R_1$ is $C_1$-$C_4$ haloalkyl. In one embodiment, $R_1$ is $CF_3$, $CH_2F$ or $CH_2Cl$. In another embodiment, $R_1$ is $CF_3$. In yet another embodiment, $R_1$ is $CH_2F$.

In an aspect, the invention provides compounds of Formula 13z1, i.e., compounds of Formula 13z, wherein $R_2$ is H.

In an aspect, the invention provides compounds of Formula 13z2, i.e., compounds of Formula 13z, wherein $R_2$ is $C_3$, $C_5$, or $C_6$ cycloalkyl. In one embodiment, $R_2$ is cyclopropyl.

In an aspect, the invention provides compounds of Formula 13z3, i.e., compounds of Formula 13z, wherein $R_2$ is $C_1$-$C_4$ haloalkyl. In one embodiment, $R_2$ is $CF_3$. In another embodiment, $R_2$ is $CH_2$—F or $CH_2$—Cl.

In another aspect, the invention provides compounds of Formula 13z4, i.e., compounds of Formula 10, where, $R_{1a}$ and $R_{2a}$ are hydrogen, $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 13z5, i.e., compounds of Formula 13z4, wherein $R_1$ is $C_3$, $C_5$, or $C_6$ cycloalkyl. In one embodiment, $R_1$ is cyclopropyl.

In an aspect, the invention provides compounds of Formula 13z6, i.e., compounds of Formula 13z4, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 13z7, i.e., compounds of Formula 13z4, wherein $R_1$ is $C_1$-$C_4$ hydroxyalkyl. In one embodiment, $R_1$ is $CH_2OH$.

In an aspect, the invention provides compounds of Formula 13z8, i.e., compounds of Formula 13z4, wherein $R_1$ is H or $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 13z9, i.e., compounds of Formula 10, wherein $R_{1a}$ and $R_{2a}$ are hydrogen and $R_2$ is $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 13z10, i.e., compounds of Formula 13z9, wherein $R_1$ is H.

In an aspect, the invention provides compounds of Formula 13z11, i.e., compounds of Formula 13z9, wherein $R_1$ is $C_3$, $C_5$, or $C_6$ cycloalkyl. In one embodiment, $R_1$ is cyclopropyl.

In an aspect, the invention provides compounds of Formula 13z12, i.e., compounds of Formula 13z9, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 13z13, i.e., compounds of Formula 13z9, wherein $R_1$ is $C_1$-$C_4$ hydroxyalkyl. In one embodiment, $R_1$ is $CH_2OH$.

In an aspect, the invention provides compounds of Formula 13z14, i.e., compounds of Formula 10, wherein $R_{1a}$, $R_{2a}$, and $R_2$ are hydrogen In an aspect, the invention provides compounds of Formula 13z15, i.e., compounds of Formula 13z14, wherein $R_1$ is $C_3$, $C_5$, or $C_6$ cycloalkyl. In one embodiment, $R_1$ is cyclopropyl.

In an aspect, the invention provides compounds of Formula 13z16, i.e., compounds of Formula 13z14, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 13z17, i.e., compounds of Formula 13z14, wherein $R_1$ is $C_1$-$C_4$ hydroxyalkyl. In one embodiment, $R_1$ is $CH_2OH$.

In an aspect, the invention provides compounds of Formula 13z18, i.e., compounds of Formula 10, wherein $R_{1a}$ and $R_{2a}$ are hydrogen and $R_2$ is $C_1$-$C_4$ hydroxyalkyl. In one embodiment, $R_2$ is $CH_2OH$.

In an aspect, the invention provides compounds of Formula 13z19, i.e., compounds of Formula 13z18, wherein $R_1$ is $C_1$-$C_4$ hydroxyalkyl. In one embodiment, $R_1$ is $CH_2OH$.

In an aspect, the invention provides compounds of Formula 13z20, i.e., compounds of Formula 13z18, wherein $R_1$ is $C_3$, $C_5$, or $C_6$ cycloalkyl. In one embodiment, $R_1$ is cyclopropyl.

In an aspect, the invention provides compounds of Formula 13z21, i.e., compounds of Formula 13z18, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 13z22, i.e., compounds of Formula 10, wherein $R_{1a}$ and $R_{2a}$ are hydrogen and $R_2$ is $C_1$-$C_4$ haloalkyl. In one embodiment, $R_2$ is $CF_3$, $CH_2F$ or $CH_2Cl$. In another embodiment, $R_2$ is $CF_3$. In yet another embodiment, $R_2$ is $CH_2F$.

In an aspect, the invention provides compounds of Formula 13z23, i.e., compounds of Formula 13z22, wherein $R_1$ is H.

In an aspect, the invention provides compounds of Formula 13z24, i.e., compounds of Formula 13z22, wherein $R_1$ is $C_3$, $C_5$, or $C_6$ cycloalkyl. In one embodiment, $R_1$ is cyclopropyl.

In an aspect, the invention provides compounds of Formula 13z25, i.e., compounds of Formula 13z22, wherein $R_1$ is $C_1$-$C_4$ haloalkyl. In one embodiment, $R_1$ is $CF_3$. In another embodiment, $R_1$ is $CH_2$—F or $CH_2$—Cl.

In yet still another aspect, the invention provides compounds of Formula 14, i.e., compounds of Formula 10, wherein $R_2$ and $R_{2a}$ combine to form oxo or $C_3$-$C_6$ cycloalkyl.

In still another aspect, the invention provides compounds of Formula 14a, i.e., compounds of Formula 14 where, $R_1$ is H, $C_1$-$C_4$ alkyl, or $C_3$-$C_6$ cycloalkyl, and $R_{1a}$ is H.

In still another aspect, the invention provides compounds of Formula 14b, i.e., compounds of Formulas 14 or 14a where, $R_1$ is H, methyl, ethyl or isopropyl. In one embodiment, $R_1$ is H. In another embodiment, $R_1$ is methyl or ethyl.

In yet another aspect, the invention provides compounds of Formula 14c, i.e., compounds of Formulas 14, or 14a where, $R_1$ is $C_3$, $C_4$, $C_5$, or $C_6$ cyclolakyl. In one embodiment, $R_1$ is $C_3$-cycloalkyl.

In yet another aspect, the invention provides compounds of Formula 14d, i.e., compounds of Formula 14, wherein $R_2$ and $R_{2a}$ combine to form oxo, and $R_1$ and $R_{1a}$ are hydrogen.

In yet another aspect, the invention provides compounds of Formula 14e, i.e., compounds of Formula 14, wherein $R_2$ and $R_{2a}$ combine to form cyclopropyl, and $R_1$ and $R_{1a}$ are hydrogen.

In one aspect, the invention provides compounds of Formula 14f, i.e., compounds of Formula 10, wherein $R_2$ and $R_{2a}$ combine to form oxo, and $R_{1a}$ is hydrogen.

In another aspect, the invention provides compounds of Formula 14g, i.e., compounds of Formula 14f, wherein $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 14h, i.e., compounds of Formula 14f, wherein $R_1$ is $C_1$-$C_4$ hydroxyalkyl. In one embodiment, $R_1$ is $CH_2OH$.

In another aspect, the invention provides compounds of Formula 14i, i.e., compounds of Formula 14f, wherein $R_1$ is $C_1$-$C_4$ haloalkyl. In one embodiment, $R_1$ is $CH_2F$ or $CH_2Cl$.

In yet still another aspect, the invention provides compounds of Formula 14j, i.e., compounds of Formula 10, wherein $R_1$ and $R_{1a}$ combine to form oxo or $C_3$-$C_6$ cycloalkyl.

In still another aspect, the invention provides compounds of Formula 14k, i.e., compounds of Formula 14j where, $R_2$ is H, $C_1$-$C_4$ alkyl, or $C_3$-$C_6$ cycloalkyl, and $R_{2a}$ is H.

In still another aspect, the invention provides compounds of Formula 14l, i.e., compounds of Formulas 14j or 14k, where $R_2$ is H, methyl, ethyl or isopropyl. In one embodiment, $R_2$ is H. In another embodiment, $R_2$ is methyl or ethyl.

In yet another aspect, the invention provides compounds of Formula 14m, i.e., compounds of Formulas 14j or 14k, where $R_2$ is $C_3$, $C_4$, $C_5$, or $C_6$ cyclolakyl. In one embodiment, $R_2$ is $C_3$-cycloalkyl.

In yet another aspect, the invention provides compounds of Formula 14n, i.e., compounds of Formula 10, wherein $R_1$ and $R_{1a}$ combine to form oxo, and $R_2$ and $R_{2a}$ are hydrogen.

In yet another aspect, the invention provides compounds of Formula 14o, i.e., compounds of Formula 10, wherein $R_1$ and $R_{1a}$ combine to form cyclopropyl, and $R_2$ and $R_{2a}$ are hydrogen.

In one aspect, the invention provides compounds of Formula 14p, i.e., compounds of Formula 10, wherein $R_1$ and $R_{1a}$ combine to form oxo, and $R_{2a}$ is hydrogen.

In another aspect, the invention provides compounds of Formula 14q, i.e., compounds of Formula 14p, wherein $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 14r, i.e., compounds of Formula 14p, wherein $R_2$ is $C_1$-$C_4$ hydroxyalkyl. In one embodiment, $R_2$ is $CH_2OH$.

In another aspect, the invention provides compounds of Formula 14s, i.e., compounds of Formula 14p, wherein $R_2$ is $C_1$-$C_4$ haloalkyl. In one embodiment, $R_2$ is $CH_2F$ or $CH_2Cl$.

In yet another aspect, the invention provides compounds of Formula 15, i.e., compounds according to any one of Formulas 10 up to and including 14s, wherein the $C_3$-$C_8$ cycloalkyl group (group A in Formula I) is cyclopropyl optionally substituted with, halogen, $C_1$-$C_2$alkyl, halo$C_1$-$C_2$alkyl, $C_1$-$C_2$ alkoxy, halo$C_1$-$C_2$ alkoxy, phenyloxy, benzyloxy, —$SO_2$—($C_1$-$C_4$ alkyl), —NR'R", $C_1$-$C_6$ alkanoyl, phenyl, benzyl, or benzoyl. In one embodiment, the cyclopropyl group is substituted with phenyloxy, benzyloxy, —$SO_2$—($C_1$-$C_4$ alkyl), —NR'R", $C_1$-$C_4$ alkanoyl, phenyl, benzyl, or benzoyl. In another embodiment, the cyclopropyl group is substituted with phenyloxy, benzyloxy, phenyl, benzyl, or benzoyl. In another embodiment, the cyclopropyl group is substituted with —$SO_2$—($C_1$-$C_4$ alkyl), —NR'R", or $C_1$-$C_4$ alkanoyl. In yet another embodiment, the cyclopropyl group is unsubstituted.

In yet another aspect, the invention provides compounds of Formula 16, i.e., compounds according to any one of Formulas 10 up to and including 14s, wherein the $C_3$-$C_8$ cycloalkyl group (group A in Formula I) is cyclobutyl optionally substituted with, halogen, $C_1$-$C_2$alkyl, halo$C_1$-$C_2$alkyl, $C_1$-$C_2$ alkoxy, halo$C_1$-$C_2$ alkoxy, phenyloxy, benzyloxy, —$SO_2$—($C_1$-$C_4$ alkyl), —NR'R", $C_1$-$C_6$ alkanoyl, phenyl, benzyl, or benzoyl. In one embodiment, the cyclobutyl group is substituted with phenyloxy, benzyloxy, —$SO_2$—($C_1$-$C_4$ alkyl), —NR'R", $C_1$-$C_4$ alkanoyl, phenyl, benzyl, or benzoyl. In another embodiment, the cyclobutyl group is substituted with phenyloxy, benzyloxy, phenyl, benzyl, or benzoyl. In another embodiment, the cyclobutyl group is substituted with —$SO_2$—($C_1$-$C_4$ alkyl), —NR'R", or $C_1$-$C_4$ alkanoyl. In yet another embodiment, the cyclobutyl group is unsubstituted.

In yet another aspect, the invention provides compounds of Formula 17, i.e., compounds according to any one of Formulas 10 up to and including 14s, wherein the $C_3$-$C_8$ cycloalkyl group (group A in Formula I) is cyclopentyl optionally substituted with, halogen, $C_1$-$C_2$alkyl, halo$C_1$-$C_2$alkyl, $C_1$-$C_2$ alkoxy, halo$C_1$-$C_2$ alkoxy, phenyloxy, benzyloxy, —$SO_2$—($C_1$-$C_4$ alkyl), —NR'R", $C_1$-$C_6$ alkanoyl, phenyl, benzyl, or benzoyl. In one embodiment, the cyclopentyl group is substituted with phenyloxy, benzyloxy, —$SO_2$—($C_1$-$C_4$ alkyl), —NR'R", $C_1$-$C_4$ alkanoyl, phenyl, benzyl, or benzoyl. In another embodiment, the cyclopentyl group is substituted with phenyloxy, benzyloxy, phenyl, benzyl, or benzoyl. In another embodiment, the cyclopentyl group is substituted with —$SO_2$—($C_1$-$C_4$ alkyl), —NR'R", or $C_1$-$C_4$ alkanoyl. In yet another embodiment, the cyclopentyl group is unsubstituted.

In yet another aspect, the invention provides compounds of Formula 18, i.e., compounds according to any one of Formulas 10 up to and including 14s, wherein the $C_3$-$C_8$ cycloalkyl group (group A in Formula I) is cyclohexyl optionally substituted with, halogen, $C_1$-$C_2$alkyl, halo$C_1$-$C_2$alkyl, $C_1$-$C_2$ alkoxy, halo$C_1$-$C_2$ alkoxy, phenyloxy, benzyloxy, —$SO_2$—($C_1$-$C_4$ alkyl), —NR'R", $C_1$-$C_6$ alkanoyl, phenyl, benzyl, or benzoyl. In one embodiment, the cyclohexyl group is substituted with phenyloxy, benzyloxy, —$SO_2$—($C_1$-$C_4$ alkyl), —NR'R", $C_1$-$C_4$ alkanoyl, phenyl, benzyl, or benzoyl. In another embodiment, the cyclohexyl group is substituted with phenyloxy, benzyloxy, phenyl, benzyl, or benzoyl. In another embodiment, the cyclohexyl group is substituted with —$SO_2$—($C_1$-$C_4$ alkyl), —NR'R", or $C_1$-$C_4$ alkanoyl. In yet another embodiment, the cyclohexyl group is unsubstituted.

In yet another aspect, the invention provides compounds of Formula 19, i.e., compounds of according to any one of Formulas 10 up to and including 14s, wherein the $C_3$-$C_8$ cycloalkyl group (group A in Formula I) is cycloheptyl optionally substituted with, halogen, $C_1$-$C_2$alkyl, halo$C_1$-$C_2$alkyl, $C_1$-$C_2$ alkoxy, halo$C_1$-$C_2$ alkoxy, phenyloxy, benzyloxy, —$SO_2$—($C_1$-$C_4$ alkyl), —NR'R", $C_1$-$C_6$ alkanoyl, phenyl, benzyl, or benzoyl. In one embodiment, the cycloheptyl group is substituted with phenyloxy, benzyloxy, —$SO_2$—($C_1$-$C_4$ alkyl), —NR'R", $C_1$-$C_4$ alkanoyl, phenyl, benzyl, or benzoyl. In another embodiment, the cycloheptyl group is substituted with phenyloxy, benzyloxy, phenyl, benzyl, or benzoyl. In another embodiment, the cycloheptyl group is substituted with —$SO_2$—($C_1$-$C_4$ alkyl), —NR'R", or $C_1$-$C_4$ alkanoyl. In yet another embodiment, the cycloheptyl group is unsubstituted.

In still yet another aspect, the invention provides compounds of Formula 20, i.e., compounds according to any one of Formulas 10 up to and including 14s, wherein the $C_3$-$C_8$ cycloalkyl group (group A in Formula I) is cyclooctyl optionally substituted with, halogen, $C_1$-$C_2$alkyl, halo$C_1$-$C_2$alkyl, $C_1$-$C_2$ alkoxy, halo$C_1$-$C_2$ alkoxy, phenyloxy, benzyloxy, —$SO_2$—($C_1$-$C_4$ alkyl), —NR'R", $C_1$-$C_6$ alkanoyl, phenyl, benzyl, or benzoyl. In one embodiment, the cyclooctyl group is substituted with phenyloxy, benzyloxy, —$SO_2$—($C_1$-$C_4$ alkyl), —NR'R", $C_1$-$C_4$ alkanoyl, phenyl, benzyl, or benzoyl. In another embodiment, the cyclooctyl group is substituted with phenyloxy, benzyloxy, phenyl, benzyl, or benzoyl. In another embodiment, the cyclooctyl group is substituted with —$SO_2$—($C_1$-$C_4$ alkyl), —NR'R", or $C_1$-$C_4$ alkanoyl. In yet another embodiment, the cyclooctyl group is unsubstituted.

In still yet another aspect, the invention provides compounds of Formula 20a, i.e., compounds according to any one of Formulas 10 up to and including 20, having the formula:

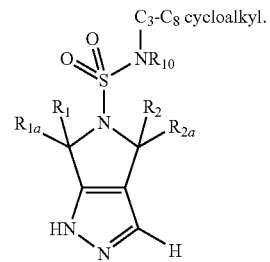

In still yet another aspect, the invention provides compounds of Formula 20b, i.e., compounds according to any one of Formulas 10 up to and including 20, having the formula:

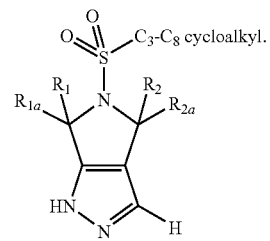

In still yet another aspect, the invention provides compounds of Formula 20c, i.e., compounds according to any one of Formulas 10 up to and including 20, having the formula:

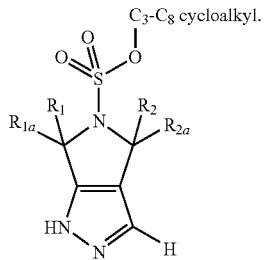

In another aspect, the invention provides compounds of Formula I wherein A is heteroaryl, which is optionally substituted at a substitutable position with halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, heteroaryl, aryl, or —$SO_2$—NR'R", where each R' and R" is independently H or $C_1$-$C_6$ alkyl.

In still another aspect, the invention provides compounds of Formula 21, i.e., compounds of Formula I with the following formula,

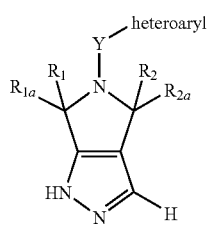

Formula 21 wherein
the heteroaryl group is optionally substituted at a substitutable position with halogen, $C_1$-$C_6$ alkyl, $C_1$-$C_6$ alkoxy, haloalkyl, haloalkoxy, hydroxyl, CN, phenyloxy, benzyloxy, —$SO_2$—($C_1$-$C_6$ alkyl), —NR'R", $C_1$-$C_6$ alkanoyl, phenyl, or —$SO_2$—NR'R";

$R_1$, $R_{1a}$, $R_2$, and $R_{2a}$, are independently hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, $C_1$-$C_6$ haloalkyl, aryl, aryl$C_1$-$C_6$ alkyl, heteroaryl, heterocyclyl, —C(O)OR', —CONR'R", $C_1$-$C_6$ haloalkyl, $C_1$-$C_4$ haloalkoxyalkyl, hydroxy $C_1$-$C_6$ alkyl, $C_1$-$C_6$ alkoxy, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, CN, or —$C_0$-$C_6$ alkyl-OC(O)-heterocyclyl, wherein each aryl, heteroaryl, and heterocyclyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo$C_1$-$C_4$ alkoxy, —C(O)NR'R", —NR'R", hydroxyl, CN, or —C(O)OR'; or $R_1$ and $R_{1a}$, or $R_2$ and $R_{2a}$ together with the carbon to which they are attached form $C_3$-$C_6$ cycloalkyl group wherein one of the carbons is optionally replaced with a heteroatom selected from N, O or S and wherein said ring may be optionally substituted with $C_1$-$C_6$ alkyl; or $R_1$ and $R_{1a}$, or $R_2$ and $R_{2a}$ together with the carbon to which they are attached form an oxo group; and R' and R" are independently H or $C_1$-$C_6$ alkyl; or R' and R" together with the atom to which they are attached may form a 3-8 membered ring optionally including an additional heteroatom such as N, O or S.

In yet another aspect, the invention provides compounds of Formula 21a, i.e., compounds of Formula 21, wherein $R_1$ is hydrogen, $C_1$-$C_6$ alkyl, $C_3$-$C_6$cycloalkyl, $C_3$-$C_6$cycloalkylalkyl, halo $C_1$-$C_4$ alkyl, halo $C_1$-$C_4$ alkoxy, —C(O)NR'R", —NR'R", hydroxyl, hydroxy $C_1$-$C_4$ alkyl, CN, or —C(O)OR', and $R_{1a}$ and $R_{2a}$ are both H.

In yet another aspect, the invention provides compounds of Formula 21b, i.e., compounds of Formula 21, wherein $R_1$ is heteroaryl. In one embodiment, $R_1$ is 1,2,4-oxadiazolyl; 1,3,4-oxadiazolyl; furanyl; pyridyl or thienyl; each of which is optionally substituted with one or more groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, CN, or —C(O)OR', where R' and R" are independently H or $C_1$-$C_6$ alkyl, or R' and R" together with the atom to which they are attached form a 3-6 membered ring.

In another aspect, the invention provides compounds of Formula 21c, i.e., compounds of Formula 21, wherein $R_1$ is 1,2,4-oxadiazolyl; 1,3,4-oxadiazolyl; furanyl; pyridyl or thienyl; each of which is substituted with at least one group that is halogen, $C_1$-$C_4$ alkyl, $C_1$-$C_4$ alkoxy, $C_2$-$C_4$ alkanoyl, halo $C_1$-$C_4$ alkyl, halo $C_1$-$C_4$ alkoxy, —C(O)NR'R", —NR'R", hydroxyl, —C(O)OR', where R' and R" are independently H or $C_1$-$C_4$ alkyl.

In another aspect, the invention provides compounds of Formula 21d, i.e., compounds of Formula 21, wherein $R_1$ is 1,2,4-oxadiazolyl; 1,3,4-oxadiazolyl; furanyl; pyridyl or thienyl; each of which is unsubstituted.

In yet another aspect, the invention provides compounds of Formula 21e, i.e., compounds of Formula 21, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$cycloalkyl, or $C_3$-$C_6$cycloalkyl$C_1$-$C_6$ alkyl; and $R_{1a}$ and $R_{2a}$ are both H.

In another aspect, the invention provides compounds of Formula 21f, i.e., compounds of Formula 21, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, or $C_3$-$C_6$ cycloalkyl, and $R_{1a}$ and $R_{2a}$ are both H.

In another aspect, the invention provides compounds of Formula 21g, i.e., compounds of Formula 21, wherein $R_1$ and $R_2$ are hydrogen, $C_1$-$C_4$ alkyl, $C_1$-$C_4$ haloalkyl, $C_1$-$C_4$ haloalkoxy, or $C_3$-$C_6$ cycloalkyl; and $R_{1a}$ and $R_{2a}$ are both H. In one embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is H. In another embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is methyl, ethyl, propyl, isopropyl or cyclopropyl. In still another embodiment, $R_1$ is methyl, ethyl, propyl, isopropyl or cyclopropyl and $R_2$ is hydrogen, $C_1$-$C_4$ alkyl, $C_1$-$C_4$ haloalkyl, $C_1$-$C_4$ haloalkoxy, or $C_3$-$C_6$cycloalkyl. In a further embodiment, $R_1$ and $R_2$ are both methyl, ethyl, isopropyl, or cyclopropyl. In a further embodiment, $R_1$ and $R_2$ are both ethyl. In a further embodiment, $R_1$ and $R_2$ are both cyclopropyl. $R_1$ and $R_2$ may be cis or trans relative to each other.

In yet another aspect, the invention provides compounds of Formula 22, i.e., compounds according to any one of Formulas 21, 21a, 21b, 21c, 21d, 21e, or 21f, wherein $R_2$ is hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, phenyl, phenyl$C_1$-$C_6$ alkyl, wherein each phenyl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, CN, or —C(O)OR'.

In yet another aspect, the invention provides compounds of Formula 22a, i.e., compounds according to any one of Formulas 21, 21a, 21b, 21c, 21d, 21e, or 21f, wherein $R_2$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$cycloalkyl, or $C_3$-$C_6$cycloalkyl$C_1$-$C_6$ alkyl.

In yet another aspect, the invention provides compounds of Formula 22b, i.e., compounds according to any one of Formulas 21, 21a, 21b, 21c, 21d, 21e, or 21f, wherein $R_2$ is hydrogen, $C_1$-$C_4$ alkyl, $C_3$-$C_6$ cycloalkyl, $C_1$-$C_4$ haloalkyl, $C_1$-$C_4$ alkoxy, or $C_1$-$C_4$ haloalkoxy, and $R_{1a}$ and $R_{2a}$ are independently hydrogen or $C_1$-$C_6$ alkyl.

In yet another aspect, the invention provides compounds of Formula 22c, i.e., compounds according to any one of Formulas 21, 21a, 21b, 21c, 21d, 21e, or 21f, wherein $R_2$ is hydrogen, $C_1$-$C_4$ alkyl, $C_1$-$C_4$ haloalky, or $C_3$-$C_6$cycloalkyl.

In another aspect, the invention provides compounds of Formula 22d, i.e. compounds of Formula 21, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is —C(O)OR', R' is $C_1$-$C_6$ alkyl and $R_{1a}$ and $R_{2a}$ are hydrogen.

In another aspect, the invention provides compounds of Formula 22e, i.e. compounds of Formula 21, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is heteroaryl and $R_{1a}$ and $R_{2a}$ are hydrogen.

In another aspect, the invention provides compounds of Formula 22f, i.e., compounds of Formulas 21 or 21b, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is 1,2,4-oxadiazolyl or 1,3,4-oxadiazolyl, and $R_{1a}$ and $R_{2a}$ are hydrogen.

In another aspect, the invention provides compounds of Formula 22g, i.e., compounds of Formulas 21 or 21b, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is furanyl, pyridyl or thienyl, and $R_{1a}$ and $R_{2a}$ are hydrogen.

In another aspect, the invention provides compounds of Formula 23c, i.e., compounds of Formula 21, wherein $R_1$ and $R_2$ are both $C_1$-$C_2$ haloalkyl and $R_{1a}$ and $R_{2a}$ are both H. $R_1$ and $R_2$ may be cis or trans relative to each other. In one embodiment, $R_1$ and $R_2$ are —CH$_2$F, —CH$_2$CF$_3$, —CH$_2$CHF$_2$, CF$_3$, or —CF$_2$CH$_3$.

In yet still another aspect, the invention provides compounds of Formula 23d, i.e., compounds of Formula 21, wherein $R_1$, $R_{1a}$ and $R_{2a}$ are hydrogen and $R_2$ is $C_3$, $C_4$, $C_5$, or $C_6$ cycloalkyl.

In yet another aspect, the invention provides compounds of Formula 23e, i.e., compounds of Formula 21, wherein where, $R_{1a}$ and $R_{2a}$ are hydrogen and $R_1$ and $R_2$ are $C_3$, $C_4$, $C_5$, or $C_6$-cycloalkyl. In one embodiment one of $R_1$ and $R_2$ is $C_3$ cycloalkyl. In another embodiment, both of $R_1$ and $R_2$ are $C_3$-cycloalkyl.

In yet another aspect, the invention provides compounds of Formula 23f, i.e., compounds of Formula 21, wherein where, $R_{1a}$ and $R_{2a}$ are hydrogen, $R_1$ is methyl, ethyl, propyl or isopropyl, and $R_2$ are $C_3$, $C_4$, $C_5$, or $C_6$-cycloalkyl. In one embodiment $R_1$ is ethyl and $R_2$ is $C_3$, $C_4$, $C_5$, or $C_6$-cycloalkyl. In one embodiment, $R_2$ is $C_3$-cycloalkyl.

In another aspect, the invention provides compounds of Formula 23g, i.e., compounds of Formula 21, where, $R_{1a}$ and $R_{2a}$ are hydrogen, $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 23h, i.e., compounds of Formula 23g, wherein $R_2$ is $C_3$, $C_5$, or $C_6$ cycloalkyl. In one embodiment, $R_2$ is cyclopropyl.

In an aspect, the invention provides compounds of Formula 23i, i.e., compounds of Formula 23g, wherein $R_2$ is $C_1$-$C_4$ haloalkyl. In one embodiment, $R_2$ is CF$_3$. In another embodiment, $R_2$ is CH$_2$—F or CH$_2$—Cl.

In an aspect, the invention provides compounds of Formula 23j, i.e., compounds of Formula 23g, wherein $R_2$ is $C_1$-$C_4$ hydroxyalkyl. In one embodiment, $R_2$ is CH$_2$OH.

In an aspect, the invention provides compounds of Formula 23k, i.e., compounds of Formula 23g, wherein $R_2$ is H or $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 23l, i.e., compounds of Formula 21, wherein $R_{1a}$ and $R_{2a}$ are hydrogen and $R_1$ is $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 23m, i.e., compounds of Formula 23l, wherein $R_2$ is H.

In an aspect, the invention provides compounds of Formula 23n, i.e., compounds of Formula 23l, wherein $R_2$ is $C_3$, $C_5$, or $C_6$ cycloalkyl. In one embodiment, $R_2$ is cyclopropyl.

In an aspect, the invention provides compounds of Formula 23o, i.e., compounds of Formula 23l, wherein $R_2$ is $C_1$-$C_4$ haloalkyl. In one embodiment, $R_2$ is CF$_3$. In another embodiment, $R_2$ is CH$_2$—F or CH$_2$—Cl.

In an aspect, the invention provides compounds of Formula 23p, i.e., compounds of Formula 23l, wherein $R_2$ is $C_1$-$C_4$ hydroxyalkyl. In one embodiment, $R_2$ is CH$_2$OH.

In an aspect, the invention provides compounds of Formula 23q, i.e., compounds of Formula 21, wherein $R_{1a}$, $R_{2a}$, and $R_1$ are hydrogen In an aspect, the invention provides compounds of Formula 23r, i.e., compounds of Formula 23q, wherein $R_2$ is H.

In an aspect, the invention provides compounds of Formula 23s, i.e., compounds of Formula 23q, wherein $R_2$ is $C_3$, $C_5$, or $C_6$ cycloalkyl. In one embodiment, $R_2$ is cyclopropyl.

In an aspect, the invention provides compounds of Formula 23t, i.e., compounds of Formula 23q, wherein $R_2$ is $C_1$-$C_4$ haloalkyl. In one embodiment, $R_2$ is CF$_3$. In another embodiment, $R_2$ is CH$_2$—F or CH$_2$—Cl.

In an aspect, the invention provides compounds of Formula 23u, i.e., compounds of Formula 23q, wherein $R_2$ is $C_1$-$C_4$ hydroxyalkyl. In one embodiment, $R_2$ is CH$_2$OH.

In an aspect, the invention provides compounds of Formula 23v, i.e., compounds of Formula 21, wherein $R_{1a}$ and $R_{2a}$ are hydrogen and $R_1$ is $C_1$-$C_4$ hydroxyalkyl. In one embodiment, $R_1$ is CH$_2$OH.

In an aspect, the invention provides compounds of Formula 23w, i.e., compounds of Formula 23v, wherein $R_2$ is $C_1$-$C_4$ hydroxyalkyl. In one embodiment, $R_2$ is CH$_2$OH.

In an aspect, the invention provides compounds of Formula 23x, i.e., compounds of Formula 23v, wherein $R_2$ is $C_3$, $C_5$, or $C_6$ cycloalkyl. In one embodiment, $R_2$ is cyclopropyl.

In an aspect, the invention provides compounds of Formula 23y, i.e., compounds of Formula 23v, wherein $R_2$ is $C_1$-$C_4$ haloalkyl. In one embodiment, $R_2$ is CF$_3$. In another embodiment, $R_2$ is CH$_2$—F or CH$_2$—Cl.

In an aspect, the invention provides compounds of Formula 23z, i.e., compounds of Formula 21, wherein $R_{1a}$ and $R_{2a}$ are hydrogen and $R_1$ is $C_1$-$C_4$ haloalkyl. In one embodiment, $R_1$ is $CF_3$, $CH_2F$ or $CH_2Cl$. In another embodiment, $R_1$ is $CF_3$. In yet another embodiment, $R_1$ is $CH_2F$.

In an aspect, the invention provides compounds of Formula 23z1, i.e., compounds of Formula 23z, wherein $R_2$ is H.

In an aspect, the invention provides compounds of Formula 23z2, i.e., compounds of Formula 23z, wherein $R_2$ is $C_3$, $C_5$, or $C_6$ cycloalkyl. In one embodiment, $R_2$ is cyclopropyl.

In an aspect, the invention provides compounds of Formula 23z3, i.e., compounds of Formula 23z, wherein $R_2$ is $C_1$-$C_4$ haloalkyl. In one embodiment, $R_2$ is $CF_3$. In another embodiment, $R_2$ is $CH_2$—F or $CH_2$—Cl.

In another aspect, the invention provides compounds of Formula 23z4, i.e., compounds of Formula 21, where, $R_{1a}$ and $R_{2a}$ are hydrogen, $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 23z5, i.e., compounds of Formula 23z4, wherein $R_1$ is $C_3$, $C_5$, or $C_6$ cycloalkyl. In one embodiment, $R_1$ is cyclopropyl.

In an aspect, the invention provides compounds of Formula 23z6, i.e., compounds of Formula 23z4, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 23z7, i.e., compounds of Formula 23z4, wherein $R_1$ is $C_1$-$C_4$ hydroxyalkyl. In one embodiment, $R_1$ is $CH_2OH$.

In an aspect, the invention provides compounds of Formula 23z8, i.e., compounds of Formula 23z4, wherein $R_1$ is H or $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 23z9, i.e., compounds of Formula 21, wherein $R_{1a}$ and $R_{2a}$ are hydrogen and $R_2$ is $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 23z10, i.e., compounds of Formula 23z9, wherein $R_1$ is H.

In an aspect, the invention provides compounds of Formula 23z11, i.e., compounds of Formula 23z9, wherein $R_1$ is $C_3$, $C_5$, or $C_6$ cycloalkyl. In one embodiment, $R_1$ is cyclopropyl.

In an aspect, the invention provides compounds of Formula 23z12, i.e., compounds of Formula 23z9, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 23z13, i.e., compounds of Formula 23z9, wherein $R_1$ is $C_1$-$C_4$ hydroxyalkyl. In one embodiment, $R_1$ is $CH_2OH$.

In an aspect, the invention provides compounds of Formula 23z14, i.e., compounds of Formula 21, wherein $R_{1a}$, $R_{2a}$, and $R_2$ are hydrogen.

In an aspect, the invention provides compounds of Formula 23z15, i.e., compounds of Formula 23z14, wherein $R_1$ is $C_3$, $C_5$, or $C_6$ cycloalkyl. In one embodiment, $R_1$ is cyclopropyl.

In an aspect, the invention provides compounds of Formula 23z16, i.e., compounds of Formula 23z14, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 23z17, i.e., compounds of Formula 23z14, wherein $R_1$ is $C_1$-$C_4$ hydroxyalkyl. In one embodiment, $R_1$ is $CH_2OH$.

In an aspect, the invention provides compounds of Formula 23z18, i.e., compounds of Formula 21, wherein $R_{1a}$ and $R_{2a}$ are hydrogen and $R_2$ is $C_1$-$C_4$ hydroxyalkyl. In one embodiment, $R_2$ is $CH_2OH$.

In an aspect, the invention provides compounds of Formula 23z19, i.e., compounds of Formula 23z18, wherein $R_1$ is $C_1$-$C_4$ hydroxyalkyl. In one embodiment, $R_1$ is $CH_2OH$.

In an aspect, the invention provides compounds of Formula 23z20, i.e., compounds of Formula 23z18, wherein $R_1$ is $C_3$, $C_5$, or $C_6$ cycloalkyl. In one embodiment, $R_1$ is cyclopropyl.

In an aspect, the invention provides compounds of Formula 23z21, i.e., compounds of Formula 23z18, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 23z22, i.e., compounds of Formula 21, wherein $R_{1a}$ and $R_{2a}$ are hydrogen and $R_2$ is $C_1$-$C_4$ haloalkyl. In one embodiment, $R_2$ is $CF_3$, $CH_2F$ or $CH_2Cl$. In another embodiment, $R_2$ is $CF_3$. In yet another embodiment, $R_2$ is $CH_2F$.

In an aspect, the invention provides compounds of Formula 23z23, i.e., compounds of Formula 23z22, wherein $R_1$ is H.

In an aspect, the invention provides compounds of Formula 23z24, i.e., compounds of Formula 23z22, wherein $R_1$ is $C_3$, $C_5$, or $C_6$ cycloalkyl. In one embodiment, $R_1$ is cyclopropyl.

In an aspect, the invention provides compounds of Formula 23z25, i.e., compounds of Formula 23z22, wherein $R_1$ is $C_1$-$C_4$ haloalkyl. In one embodiment, $R_1$ is $CF_3$. In another embodiment, $R_1$ is $CH_2$—F or $CH_2$—Cl.

In yet still another aspect, the invention provides compounds of Formula 24, i.e., compounds of Formula 21, wherein $R_2$ and $R_{2a}$ combine to form oxo or $C_3$-$C_6$cycloalkyl.

In still another aspect, the invention provides compounds of Formula 24a, i.e., compounds of Formula 24 where, $R_1$ is H, $C_1$-$C_4$ alkyl, or $C_3$-$C_6$ cycloalkyl, and $R_{1a}$ is H.

In still another aspect, the invention provides compounds of Formula 24b, i.e., compounds of Formulas 24 or 24a where, $R_1$ is H, methyl, ethyl or isopropyl. In one embodiment, $R_1$ is H. In another embodiment, $R_1$ is methyl or ethyl.

In yet another aspect, the invention provides compounds of Formula 24c, i.e., compounds of Formulas 24, or 24a where, $R_1$ is $C_3$, $C_4$, $C_5$, or $C_6$ cyclolakyl. In one embodiment, $R_1$ is $C_3$ cycloalkyl.

In yet another aspect, the invention provides compounds of Formula 24d, i.e., compounds of Formula 21, wherein $R_2$ and $R_{2a}$ combine to form oxo, and $R_1$ and $R_{1a}$ are hydrogen.

In yet another aspect, the invention provides compounds of Formula 24e, i.e., compounds of Formula 21, wherein $R_2$ and $R_{2a}$ combine to form cyclopropyl, and $R_1$ and $R_{1a}$ are hydrogen.

In one aspect, the invention provides compounds of Formula 24f, i.e., compounds of Formula 21, wherein $R_2$ and $R_{2a}$ combine to form oxo, and $R_{1a}$ is hydrogen.

In another aspect, the invention provides compounds of Formula 24g, i.e., compounds of Formula 24f, wherein $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 24h, i.e., compounds of Formula 24f, wherein $R_1$ is $C_1$-$C_4$ hydroxyalkyl. In one embodiment, $R_1$ is $CH_2OH$.

In another aspect, the invention provides compounds of Formula 24i, i.e., compounds of Formula 24f, wherein $R_1$ is $C_1$-$C_4$ haloalkyl. In one embodiment, $R_1$ is $CH_2F$ or $CH_2Cl$.

In yet still another aspect, the invention provides compounds of Formula 24j, i.e., compounds of Formula 21, wherein $R_1$ and $R_{1a}$ combine to form oxo or $C_3$-$C_6$cycloalkyl.

In still another aspect, the invention provides compounds of Formula 24k, i.e., compounds of Formula 24j where, $R_2$ is H, $C_1$-$C_4$ alkyl, or $C_3$-$C_6$ cycloalkyl, and $R_{2a}$ is H.

In still another aspect, the invention provides compounds of Formula 24l, i.e., compounds of Formulas 24j or 24k, where $R_2$ is H, methyl, ethyl or isopropyl. In one embodiment, $R_2$ is H. In another embodiment, $R_2$ is methyl or ethyl.

In yet another aspect, the invention provides compounds of Formula 24m, i.e., compounds of Formulas 24j or 24k, where $R_2$ is $C_3$, $C_4$, $C_5$, or $C_6$ cyclolakyl. In one embodiment, $R_2$ is $C_3$-cycloalkyl.

In yet another aspect, the invention provides compounds of Formula 24n, i.e., compounds of Formula 21, wherein $R_1$ and $R_{1a}$ combine to form oxo, and $R_2$ and $R_{2a}$ are hydrogen.

In yet another aspect, the invention provides compounds of Formula 24o, i.e., compounds of Formula 21, wherein $R_1$ and $R_{1a}$ combine to form cyclopropyl, and $R_2$ and $R_{2a}$ are hydrogen.

In one aspect, the invention provides compounds of Formula 24p, i.e., compounds of Formula 21, wherein $R_1$ and $R_{1a}$ combine to form oxo, and $R_{2a}$ is hydrogen.

In another aspect, the invention provides compounds of Formula 24q, i.e., compounds of Formula 24p, wherein $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 24r, i.e., compounds of Formula 24p, wherein $R_2$ is $C_1$-$C_4$ hydroxyalkyl. In one embodiment, $R_2$ is $CH_2OH$.

In another aspect, the invention provides compounds of Formula 24s, i.e., compounds of Formula 24p, wherein $R_2$ is $C_1$-$C_4$ haloalkyl. In one embodiment, $R_2$ is $CH_2F$ or $CH_2Cl$.

In yet still another aspect, the invention provides compounds of Formula 25, i.e., compounds according to any one of Formulas 21 up to and including 24s, wherein the heteroaryl group (group A in Formula I) is pyridyl optionally substituted with 1 or 2 groups that are independently halogen, $C_1$-$C_4$ alkyl, $C_1$-$C_4$ alkoxy, $CF_3$, $OCF_3$, OH, amino, mono or di($C_1$-$C_4$ alkyl)amino, phenyloxy, benzyloxy, —$SO_2$—($C_1$-$C_4$ alkyl), $C_1$-$C_6$ alkanoyl, phenyl, benzyl, or benzoyl. In one embodiment, the pyridyl group is substituted with phenyloxy, benzyloxy, —$SO_2$—($C_1$-$C_4$ alkyl), —NR'R", $C_1$-$C_4$ alkanoyl, phenyl, benzyl, or benzoyl. In another embodiment, the pyridyl group is substituted with phenyloxy, benzyloxy, phenyl, benzyl, or benzoyl. In another embodiment, the pyridyl group is substituted with —$SO_2$—($C_1$-$C_4$ alkyl), —NR'R", or $C_1$-$C_4$ alkanoyl. In yet another embodiment, the pyridyl group is optionally substituted with 1 or 2 groups that are independently halogen, $C_1$-$C_4$ alkyl, $C_1$-$C_4$ alkoxy, $CF_3$, $OCF_3$, OH, amino, mono or di($C_1$-$C_4$ alkyl)amino.

In yet still another aspect, the invention provides compounds of Formula 25a, i.e., compounds of Formula 25, wherein the pyridyl is substituted with one group that is halogen, $C_1$-$C_4$ alkyl, $C_1$-$C_4$ alkoxy, $CF_3$, $OCF_3$, OH, amino, or mono or di($C_1$-$C_4$ alkyl)amino.

In yet still another aspect, the invention provides compounds of Formula 25b, i.e., compounds of Formula 25, wherein the pyridyl is substituted at the 4-position.

In yet still another aspect, the invention provides compounds of Formula 25c, i.e., compounds of Formulas 25, wherein the pyridyl is substituted with one group that is halogen. In one embodiment, the pyridyl is a pyrid-2-yl. In another embodiment, the pyridyl is a pyrid-3-yl. In still another embodiment, the pyridyl is a pyrid-4-yl.

In yet still another aspect, the invention provides compounds of Formula 25d, i.e., compounds of Formula 25, wherein the heteroaryl group has the following structure:

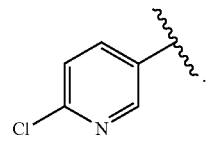

In yet still another aspect, the invention provides compounds of Formula 25e, wherein the heteroaryl group (group A in Formula I) is an unsubstituted pyridyl. In one embodiment, the pyridyl is a pyrid-2-yl. In another embodiment, the pyridyl is a pyrid-3-yl. In still another embodiment, the pyridyl is a pyrid-4-yl.

In yet still another aspect, the invention provides compounds of Formula 25f, i.e., compounds of Formulas 25, wherein the pyridyl is substituted with one group that is $C_1$-$C_4$ haloalkyl. In one embodiment, the $C_1$-$C_4$ haloalkyl group is $CF_3$. In another embodiment, pyridyl is a pyrid-2-yl. In still another embodiment, the pyridyl is a pyrid-3-yl. In yet another embodiment, the pyridyl is a pyrid-4-yl.

In yet still another aspect, the invention provides compounds of Formula 25g, i.e., compounds of Formula 25, wherein the heteroaryl group has the following structure:

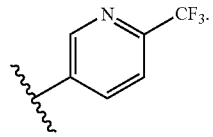

In yet still another aspect, the invention provides compounds of Formula 26, i.e., compounds according to any one of Formulas 21 up to and including 24s wherein the heteroaryl group (group A in Formula I) is thienyl optionally substituted with 1 or 2 groups that are independently halogen, $C_1$-$C_4$ alkyl, $C_1$-$C_4$ alkoxy, $CF_3$, $OCF_3$, OH, amino, mono or di($C_1$-$C_4$ alkyl)amino phenyloxy, benzyloxy, —$SO_2$—($C_1$-$C_4$ alkyl), $C_1$-$C_6$ alkanoyl, phenyl, benzyl, or benzoyl. In one embodiment, the thienyl group is substituted with phenyloxy, benzyloxy, —$SO_2$—($C_1$-$C_4$ alkyl), —NR'R", $C_1$-$C_4$ alkanoyl, phenyl, benzyl, or benzoyl. In another embodiment, the thienyl group is substituted with phenyloxy, benzyloxy, phenyl, benzyl, or benzoyl. In another embodiment, the thienyl group is substituted with —$SO_2$—($C_1$-$C_4$ alkyl), —NR'R", or $C_1$-$C_4$ alkanoyl. In yet another embodiment, the thienyl group is optionally substituted with 1 or 2 groups that are independently halogen, $C_1$-$C_4$ alkyl, $C_1$-$C_4$ alkoxy, $CF_3$, $OCF_3$, OH, amino, mono or di($C_1$-$C_4$ alkyl)amino.

In yet still another aspect, the invention provides compounds of Formula 26a, i.e., compounds of Formula 26 where the thienyl group is substituted with one group that is halogen, $C_1$-$C_4$ alkyl, $C_1$-$C_4$ alkoxy, $CF_3$, $OCF_3$, OH, amino, or mono or di($C_1$-$C_4$ alkyl)amino.

In yet still another aspect, the invention provides compounds of Formula 26b, i.e., compounds of Formulas 26 or 26a, wherein the thienyl group is substituted with one halogen.

In yet still another aspect, the invention provides compounds of Formula 26c, i.e., compounds of Formula 26b, wherein the thienyl group has the formula:

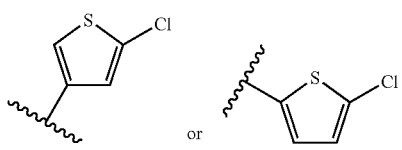

In yet still another aspect, the invention provides compounds of Formula 26d, i.e., compounds of Formula 26, wherein the thienyl group is unsubstituted.

In yet still another aspect, the invention provides compounds of Formula 26e, i.e., compounds of Formula 26d, wherein the thienyl group has the formula:

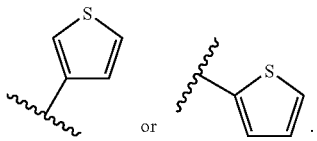

In another aspect, the invention provides compounds of Formula 26f, i.e., compounds according to any one of Formulas 21 up to and including 26e, having the formula:

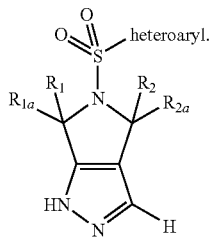

In another aspect, the invention provides compounds of Formula 26g, i.e., compounds according to any one of Formulas 21 up to and including 26e, having the formula:

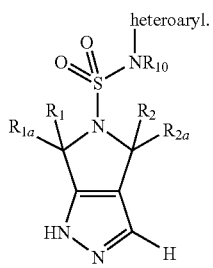

In another aspect, the invention provides compounds of Formula 26h, i.e., compounds according to any one of Formulas 21 up to and including 26e, having the formula:

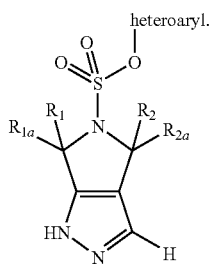

In another aspect, the invention provides compounds of Formula I, wherein A is heterocyclyl, which is optionally substituted at a substitutable position with halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, heteroaryl, aryl, or —$SO_2$—NR'R", where each R' and R" is independently H or $C_1$-$C_6$ alkyl.

In another aspect, the invention provides compounds of Formula 27, i.e., compounds of Formula I having the following formula

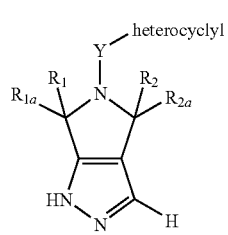

Formula 27 wherein
the heterocyclyl group is optionally substituted at a substitutable position with halogen, $C_1$-$C_6$ alkyl, $C_1$-$C_6$ alkoxy, haloalkyl, haloalkoxy, hydroxyl, CN, phenyloxy, benzyloxy, —$SO_2$—($C_1$-$C_6$ alkyl), —NR'R", $C_1$-$C_6$ alkanoyl, pyridyl, phenyl, or —$SO_2$—NR'R", $R_1$, $R_{1a}$, $R_2$, and $R_{2a}$, are independently hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, $C_1$-$C_6$ haloalkyl, aryl, aryl$C_1$-$C_6$ alkyl, heteroaryl, heterocyclyl, —C(O)OR', —CONR'R", $C_1$-$C_6$ haloalkyl, $C_1$-$C_4$ haloalkoxyalkyl, hydroxy $C_1$-$C_6$ alkyl, $C_1$-$C_6$ alkoxy, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, CN, or —$C_0$-$C_6$ alkyl-OC(O)-heterocyclyl, wherein each aryl, heteroaryl, and heterocyclyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo$C_1$-$C_4$ alkoxy, —C(O)NR'R", —NR'R", hydroxyl, CN, or —C(O)OR'; or $R_1$ and $R_{1a}$, or $R_2$ and $R_{2a}$ together with the carbon to which they are attached form $C_3$-$C_6$ cycloalkyl group wherein one of the carbons is optionally replaced with a heteroatom selected from N, O or S and wherein said ring may be optionally substituted with $C_1$-$C_6$ alkyl; or $R_1$ and $R_{1a}$, or $R_2$ and $R_{2a}$ together with the carbon to which they are attached form an oxo group; and R' and R" are independently H or $C_1$-$C_6$ alkyl; or R' and R" together with the atom to which they are attached may form a 3-8 membered ring optionally including an additional heteroatom such as N, O or S.

In yet another aspect, the invention provides compounds of Formula 28, i.e., compounds of Formula 27, wherein $R_1$ is hydrogen, $C_1$-$C_6$ alkyl, $C_3$-$C_6$cycloalkyl, $C_3$-$C_6$cycloalkylalkyl, halo $C_1$-$C_4$ alkyl, halo $C_1$-$C_4$ alkoxy, —C(O)NR'R", —NR'R", hydroxyl, hydroxy $C_1$-$C_4$ alkyl, CN, or —C(O)OR', and $R_{1a}$ and $R_{2a}$ are both H.

In yet another aspect, the invention provides compounds of Formula 28a, i.e., compounds of Formula 27, wherein $R_1$ is heteroaryl. In one embodiment, $R_1$ is 1,2,4-oxadiazolyl; 1,3,4-oxadiazolyl; furanyl; pyridyl or thienyl; each of which is optionally substituted with one or more groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, CN, or —C(O)OR', where R' and R" are independently H or $C_1$-$C_6$ alkyl, or R' and R" together with the atom to which they are attached form a 3-6 membered ring.

In another aspect, the invention provides compounds of Formula 28b, i.e., compounds of Formula 27, wherein $R_1$ is 1,2,4-oxadiazolyl; 1,3,4-oxadiazolyl; furanyl; pyridyl or thienyl; each of which is substituted with at least one group that is halogen, $C_1$-$C_4$ alkyl, $C_1$-$C_4$ alkoxy, $C_2$-$C_4$ alkanoyl, halo $C_1$-$C_4$ alkyl, halo $C_1$-$C_4$ alkoxy, —C(O)NR'R'', —NR'R'', hydroxyl, —C(O)OR', where R' and R'' are independently H or $C_1$-$C_4$ alkyl.

In another aspect, the invention provides compounds of Formula 28c, i.e., compounds of Formula 27, wherein $R_1$ is 1,2,4-oxadiazolyl; 1,3,4-oxadiazolyl; furanyl; pyridyl or thienyl; each of which is unsubstituted.

In yet another aspect, the invention provides compounds of Formula 28d, i.e., compounds of Formula 27, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$ cycloalkyl, or $C_3$-$C_6$ cycloalkyl$C_1$-$C_6$ alkyl; and $R_{1a}$ and $R_{2a}$ are both H.

In another aspect, the invention provides compounds of Formula 28e, i.e., compounds of Formula 27, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, or $C_3$-$C_6$ cycloalkyl, and $R_{1a}$ and $R_{2a}$ are both H.

In another aspect, the invention provides compounds of Formula 28f, i.e., compounds of Formula 27, wherein $R_1$ and $R_2$ are hydrogen, $C_1$-$C_4$ alkyl, $C_1$-$C_4$ haloalkyl, $C_1$-$C_4$ haloalkoxy, or $C_3$-$C_6$ cycloalkyl; and $R_{1a}$ and $R_{2a}$ are both H. In one embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is H. In another embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is methyl, ethyl, propyl, isopropyl or cyclopropyl. In still another embodiment, $R_1$ is methyl, ethyl, propyl, isopropyl or cyclopropyl and $R_2$ is hydrogen, $C_1$-$C_4$ alkyl, $C_1$-$C_4$ haloalkyl, $C_1$-$C_4$ haloalkoxy, or $C_3$-$C_6$ cycloalkyl. In a further embodiment, $R_1$ and $R_2$ are both methyl, ethyl, isopropyl, or cyclopropyl. In a further embodiment, $R_1$ and $R_2$ are both ethyl. In a further embodiment, $R_1$ and $R_2$ are both cyclopropyl. $R_1$ and $R_2$ may be cis or trans relative to each other.

In yet another aspect, the invention provides compounds of Formula 29, i.e., compounds according to any one of Formulas 27, 28, 28a, 28b, 28c, 28d, or 28e, wherein $R_2$ is hydrogen, $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkyl$C_1$-$C_6$ alkyl, phenyl, phenyl$C_1$-$C_6$ alkyl, wherein each phenyl group is optionally substituted with 1, 2, 3, 4, or 5 groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R'', —NR'R'', hydroxyl, CN, or —C(O)OR'.

In yet another aspect, the invention provides compounds of Formula 29a, i.e., compounds according to any one of Formulas 27, 28, 28a, 28b, 28c, 28d, or 28e, wherein $R_2$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$ cycloalkyl, or $C_3$-$C_6$ cycloalkyl$C_1$-$C_6$ alkyl.

In yet another aspect, the invention provides compounds of Formula 29b, i.e., compounds according to any one of Formulas 27, 28, 28a, 28b, 28c, 28d, or 28e, wherein $R_2$ is hydrogen, $C_1$-$C_4$ alkyl, $C_3$-$C_6$ cycloalkyl, $C_1$-$C_4$ haloalkyl, $C_1$-$C_4$ alkoxy, or $C_1$-$C_4$ haloalkoxy, and $R_1$, $R_{1a}$ and $R_{2a}$ are independently hydrogen or $C_1$-$C_6$ alkyl.

In yet another aspect, the invention provides compounds of Formula 29c, i.e., compounds according to any one of Formulas 27, 28, 28a, 28b, 28c, 28d, or 28e, wherein $R_2$ is hydrogen, $C_1$-$C_4$ alkyl, $C_1$-$C_4$ haloalkyl, or $C_3$-$C_6$ cycloalkyl.

In another aspect, the invention provides compounds of Formula 29d, i.e. compounds of Formula 27, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is —C(O)OR', R' is $C_1$-$C_6$ alkyl and $R_{1a}$ and $R_{2a}$ are hydrogen.

In another aspect, the invention provides compounds of Formula 29e, i.e. compounds of Formula 27, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is heteroaryl and $R_{1a}$ and $R_{2a}$ are hydrogen.

In another aspect, the invention provides compounds of Formula 29f, i.e., compounds of Formulas 27, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is 1,2,4-oxadiazolyl or 1,3,4-oxadiazolyl, and $R_{1a}$ and $R_{2a}$ are hydrogen.

In another aspect, the invention provides compounds of Formula 29g, i.e., compounds of Formulas 27 or 28a, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is furanyl, pyridyl or thienyl, and $R_{1a}$ and $R_{2a}$ are hydrogen.

In another aspect, the invention provides compounds of Formula 30c, i.e., compounds of Formula 27, wherein $R_1$ and $R_2$ are both $C_1$-$C_2$ haloalkyl and $R_{1a}$ and $R_{2a}$ are both H. $R_1$ and $R_2$ may be cis or trans relative to each other. In one embodiment, $R_1$ and $R_2$ are —$CH_2F$, —$CH_2CF_3$, —$CH_2CHF_2$, $CF_3$, or —$CF_2CH_3$.

In yet still another aspect, the invention provides compounds of Formula 30d, i.e., compounds of Formula 27, wherein $R_1$, $R_{1a}$ and $R_{2a}$ are hydrogen and $R_2$ is $C_3$, $C_4$, $C_5$, or $C_6$-cycloalkyl.

In yet another aspect, the invention provides compounds of Formula 30e, i.e., compounds of Formula 27, wherein $R_{1a}$ and $R_{2a}$ are hydrogen and $R_1$ and $R_2$ are $C_3$, $C_4$, $C_5$, or $C_6$ cycloalkyl. In one embodiment one of $R_1$ and $R_2$ is $C_3$ cycloalkyl. In another embodiment, both of $R_1$ and $R_2$ are $C_3$-cycloalkyl.

In yet another aspect, the invention provides compounds of Formula 30f, i.e., compounds of Formula 27, wherein $R_{1a}$ and $R_{2a}$ are hydrogen, $R^1$ is methyl, ethyl, propyl and isopropyl, and $R_2$ are $C_3$, $C_4$, $C_5$, or $C_6$-cycloalkyl. In one embodiment $R^1$ is ethyl and $R_2$ is $C_3$, $C_4$, $C_5$, or $C_6$-cycloalkyl. In one embodiment, $R_2$ is $C_3$ cycloalkyl.

In another aspect, the invention provides compounds of Formula 30g, i.e., compounds of Formula 27, wherein $R_{1a}$ and $R_{2a}$ are hydrogen, $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 30h, i.e., compounds of Formula 30g, wherein $R_2$ is $C_3$, $C_5$, or $C_6$ cycloalkyl. In one embodiment, $R_2$ is cyclopropyl.

In an aspect, the invention provides compounds of Formula 30i, i.e., compounds of Formula 30g, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 30j, i.e., compounds of Formula 30g, wherein $R_2$ is $C_1$-$C_4$ hydroxyalkyl. In one embodiment, $R_2$ is $CH_2OH$.

In an aspect, the invention provides compounds of Formula 30k, i.e., compounds of Formula 30g, wherein $R_2$ is H or $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 30l, i.e., compounds of Formula 27, wherein $R_{1a}$ and $R_{2a}$ are hydrogen and $R_1$ is $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 30m, i.e., compounds of Formula 30l, wherein $R_2$ is H.

In an aspect, the invention provides compounds of Formula 30n, i.e., compounds of Formula 30l, wherein $R_2$ is $C_3$, $C_5$, or $C_6$ cycloalkyl. In one embodiment, $R_2$ is cyclopropyl.

In an aspect, the invention provides compounds of Formula 30o, i.e., compounds of Formula 30l, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 30p, i.e., compounds of Formula 30l, wherein $R_2$ is $C_1$-$C_4$ hydroxyalkyl. In one embodiment, $R_2$ is $CH_2OH$.

In an aspect, the invention provides compounds of Formula 30q, i.e., compounds of Formula 27, wherein $R_{1a}$, $R_{2a}$, and $R_1$ are hydrogen In an aspect, the invention provides compounds of Formula 30r, i.e., compounds of Formula 30q, wherein $R_2$ is H.

In an aspect, the invention provides compounds of Formula 30s, i.e., compounds of Formula 30q, wherein $R_2$ is $C_3$, $C_5$, or $C_6$ cycloalkyl. In one embodiment, $R_2$ is cyclopropyl.

In an aspect, the invention provides compounds of Formula 30t, i.e., compounds of Formula 30q, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 30u, i.e., compounds of Formula 30q, wherein $R_2$ is $C_1$-$C_4$ hydroxyalkyl. In one embodiment, $R_2$ is $CH_2OH$.

In an aspect, the invention provides compounds of Formula 30v, i.e., compounds of Formula 27, wherein $R_{1a}$ and $R_{2a}$ are hydrogen and $R_1$ is $C_1$-$C_4$ hydroxyalkyl. In one embodiment, $R_1$ is $CH_2OH$.

In an aspect, the invention provides compounds of Formula 30w, i.e., compounds of Formula 30v, wherein $R_2$ is $C_1$-$C_4$ hydroxyalkyl. In one embodiment, $R_2$ is $CH_2OH$.

In an aspect, the invention provides compounds of Formula 30x, i.e., compounds of Formula 30v, wherein $R_2$ is $C_3$, $C_5$, or $C_6$ cycloalkyl. In one embodiment, $R_2$ is cyclopropyl.

In an aspect, the invention provides compounds of Formula 30y, i.e., compounds of Formula 30v, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 30z, i.e., compounds of Formula 27, wherein $R_{1a}$ and $R_{2a}$ are hydrogen and $R_1$ is $C_1$-$C_4$ haloalkyl. In one embodiment, $R_1$ is $CF_3$, $CH_2F$ or $CH_2Cl$. In another embodiment, $R_1$ is $CF_3$. In yet another embodiment, $R_1$ is $CH_2F$.

In an aspect, the invention provides compounds of Formula 30z1, i.e., compounds of Formula 30z, wherein $R_2$ is H.

In an aspect, the invention provides compounds of Formula 30z2, i.e., compounds of Formula 30z, wherein $R_2$ is $C_3$, $C_5$, or $C_6$ cycloalkyl. In one embodiment, $R_2$ is cyclopropyl.

In an aspect, the invention provides compounds of Formula 30z3, i.e., compounds of Formula 30z, wherein $R_2$ is $C_1$-$C_4$ haloalkyl. In one embodiment, $R_2$ is $CF_3$. In another embodiment, $R_2$ is $CH_2$—F or $CH_2$—Cl.

In another aspect, the invention provides compounds of Formula 30z4, i.e., compounds of Formula 27, where, $R_{1a}$ and $R_{2a}$ are hydrogen, $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 30z5, i.e., compounds of Formula 30z4, wherein $R_1$ is $C_3$, $C_5$, or $C_6$ cycloalkyl. In one embodiment, $R_1$ is cyclopropyl.

In an aspect, the invention provides compounds of Formula 30z6, i.e., compounds of Formula 30z4, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 30z7, i.e., compounds of Formula 30z4, wherein $R_1$ is $C_1$-$C_4$ hydroxyalkyl. In one embodiment, $R_1$ is $CH_2OH$.

In an aspect, the invention provides compounds of Formula 30z8, i.e., compounds of Formula 30z4, wherein $R_1$ is H or $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 30z9, i.e., compounds of Formula 27, wherein $R_{1a}$ and $R_{2a}$ are hydrogen and $R_2$ is $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 30z10, i.e., compounds of Formula 30z9, wherein $R_1$ is H.

In an aspect, the invention provides compounds of Formula 30z11, i.e., compounds of Formula 30z9, wherein $R_1$ is $C_3$, $C_5$, or $C_6$ cycloalkyl. In one embodiment, $R_1$ is cyclopropyl.

In an aspect, the invention provides compounds of Formula 30z12, i.e., compounds of Formula 30z9, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 30z13, i.e., compounds of Formula 30z9, wherein $R_1$ is $C_1$-$C_4$ hydroxyalkyl. In one embodiment, $R_1$ is $CH_2OH$.

In an aspect, the invention provides compounds of Formula 30z14, i.e., compounds of Formula 27, wherein $R_{1a}$, $R_{2a}$, and $R_2$ are hydrogen In an aspect, the invention provides compounds of Formula 30z15, i.e., compounds of Formula 30z14, wherein $R_1$ is $C_3$, $C_5$, or $C_6$ cycloalkyl. In one embodiment, $R_1$ is cyclopropyl.

In an aspect, the invention provides compounds of Formula 30z16, i.e., compounds of Formula 30z14, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 30z17, i.e., compounds of Formula 30z14, wherein $R_1$ is $C_1$-$C_4$ hydroxyalkyl. In one embodiment, $R_1$ is $CH_2OH$.

In an aspect, the invention provides compounds of Formula 30z18, i.e., compounds of Formula 27, wherein $R_{1a}$ and $R_{2a}$ are hydrogen and $R_2$ is $C_1$-$C_4$ hydroxyalkyl. In one embodiment, $R_2$ is $CH_2OH$.

In an aspect, the invention provides compounds of Formula 30z19, i.e., compounds of Formula 30z18, wherein $R_1$ is $C_1$-$C_4$ hydroxyalkyl. In one embodiment, $R_1$ is $CH_2OH$.

In an aspect, the invention provides compounds of Formula 30z20, i.e., compounds of Formula 30z18, wherein $R_1$ is $C_3$, $C_5$, or $C_6$ cycloalkyl. In one embodiment, $R_1$ is cyclopropyl.

In an aspect, the invention provides compounds of Formula 30z21, i.e., compounds of Formula 30z18, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 30z22, i.e., compounds of Formula 27, wherein $R_{1a}$ and $R_{2a}$ are hydrogen and $R_2$ is $C_1$-$C_4$ haloalkyl. In one embodiment, $R_2$ is $CF_3$, $CH_2F$ or $CH_2Cl$. In another embodiment, $R_2$ is $CF_3$. In yet another embodiment, $R_2$ is $CH_2F$.

In an aspect, the invention provides compounds of Formula 30z23, i.e., compounds of Formula 30z22, wherein $R_1$ is H.

In an aspect, the invention provides compounds of Formula 30z24, i.e., compounds of Formula 30z22, wherein $R_1$ is $C_3$, $C_5$, or $C_6$ cycloalkyl. In one embodiment, $R_1$ is cyclopropyl.

In an aspect, the invention provides compounds of Formula 30z25, i.e., compounds of Formula 30z22, wherein $R_1$ is $C_1$-$C_4$ haloalkyl. In one embodiment, $R_1$ is $CF_3$. In another embodiment, $R_1$ is $CH_2$—F or $CH_2$—Cl.

In yet still another aspect, the invention provides compounds of Formula 31, i.e., compounds of Formula 27, wherein $R_2$ and $R_{2a}$ combine to form oxo or $C_3$-$C_6$cycloalkyl.

In still another aspect, the invention provides compounds of Formula 31a, i.e., compounds of Formula 31 where, $R_1$ is H, $C_1$-$C_4$ alkyl, or $C_3$-$C_6$ cycloalkyl, and $R_{1a}$ is H.

In still another aspect, the invention provides compounds of Formula 31b, i.e., compounds of Formulas 31 or 31a where, $R_1$ is H, methyl, ethyl or isopropyl. In one embodiment, $R_1$ is H. In another embodiment, $R_1$ is methyl or ethyl.

In yet another aspect, the invention provides compounds of Formula 31c, i.e., compounds of Formulas 31 or 31a, where, $R_1$ is $C_3$, $C_4$, $C_5$, or $C_6$ cyclolakyl. In one embodiment, $R_1$ is $C_3$ cycloalkyl.

In yet another aspect, the invention provides compounds of Formula 31d, i.e., compounds of Formula 31, wherein $R_2$ and $R_{2a}$ combine to form oxo, and $R_1$ and $R_{1a}$ are hydrogen.

In yet another aspect, the invention provides compounds of Formula 31e, i.e., compounds of Formula 31, wherein $R_2$ and $R_{2a}$ combine to form cyclopropyl, and $R_1$ and $R_{1a}$ are hydrogen.

In one aspect, the invention provides compounds of Formula 31f, i.e., compounds of Formula 27, wherein $R_2$ and $R_{2a}$ combine to form oxo, and $R_{1a}$ is hydrogen.

In another aspect, the invention provides compounds of Formula 31g, i.e., compounds of Formula 31f, wherein $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 31h, i.e., compounds of Formula 31f, wherein $R_1$ is $C_1$-$C_4$ hydroxyalkyl. In one embodiment, $R_1$ is $CH_2OH$.

In another aspect, the invention provides compounds of Formula 31i, i.e., compounds of Formula 31f, wherein $R_1$ is $C_1$-$C_4$ haloalkyl. In one embodiment, $R_1$ is $CH_2F$ or $CH_2Cl$.

In yet still another aspect, the invention provides compounds of Formula 31j, i.e., compounds of Formula 27, wherein $R_1$ and $R_{1a}$ combine to form oxo or $C_3$-$C_6$cycloalkyl.

In still another aspect, the invention provides compounds of Formula 31k, i.e., compounds of Formula 31j where, $R_2$ is H, $C_1$-$C_4$ alkyl, or $C_3$-$C_6$ cycloalkyl, and $R_{2a}$ is H.

In still another aspect, the invention provides compounds of Formula 31l, i.e., compounds of Formulas 31j or 31k, where $R_2$ is H, methyl, ethyl or isopropyl. In one embodiment, $R_2$ is H. In another embodiment, $R_2$ is methyl or ethyl.

In yet another aspect, the invention provides compounds of Formula 31m, i.e., compounds of Formulas 31j or 31k, where $R_2$ is $C_3$, $C_4$, $C_5$, or $C_6$ cyclolakyl. In one embodiment, $R_2$ is $C_3$-cycloalkyl.

In yet another aspect, the invention provides compounds of Formula 31n, i.e., compounds of Formula 27, wherein $R_1$ and $R_{1a}$ combine to form oxo, and $R_2$ and $R_{2a}$ are hydrogen.

In yet another aspect, the invention provides compounds of Formula 31o, i.e., compounds of Formula 27, wherein $R_1$ and $R_{1a}$ combine to form cyclopropyl, and $R_2$ and $R_{2a}$ are hydrogen.

In one aspect, the invention provides compounds of Formula 31p, i.e., compounds of Formula 27, wherein $R_1$ and $R_{1a}$ combine to form oxo, and $R_{2a}$ is hydrogen.

In another aspect, the invention provides compounds of Formula 31q, i.e., compounds of Formula 31p, wherein $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 31r, i.e., compounds of Formula 31p, wherein $R_2$ is $C_1$-$C_4$ hydroxyalkyl. In one embodiment, $R_2$ is $CH_2OH$.

In another aspect, the invention provides compounds of Formula 31s, i.e., compounds of Formula 31p, wherein $R_2$ is $C_1$-$C_4$ haloalkyl. In one embodiment, $R_2$ is $CH_2F$ or $CH_2Cl$.

In another aspect, the invention provides compounds of formula 32, i.e., compounds according to any one of Formulas 27 up to and including 31s, wherein the heterocyclyl group (the A-group in Formula 1) is piperidinyl, piperazinyl, pyrrolidinyl, morpholinyl, thiomorpholinyl, thiomorpholinyl S,S-dioxide, tetrahydrofuranyl, or imidazolidinyl, each of which is optionally substituted with halogen, $C_1$-$C_6$ alkyl, $C_1$-$C_6$ alkoxy, haloalkyl, haloalkoxy, hydroxyl, CN, aryloxy, arylalkyloxy, —$SO_2$—($C_1$-$C_6$ alkyl), —NR'R", $C_1$-$C_6$ alkanoyl, pyridyl, phenyl, or —$SO_2$—NR'R".

In yet another aspect, the invention provides compounds of Formula 32a, i.e., compounds according to any one of Formulas 27 up to and including 32, wherein the heterocyclyl group (group A in Formula I) is morpholinyl optionally substituted with one or more groups that are independently halogen, $C_1$-$C_6$ alkyl, $C_1$-$C_6$ alkoxy, haloalkyl, haloalkoxy, hydroxyl, CN, phenyloxy, benzyloxy, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of Formula 32b, i.e., compounds of Formula 32a where the morpholinyl group is not attached to the sulfur of the $SO_2$ group via the ring nitrogen.

In still another aspect, the invention provides compounds of Formula 32c, i.e., compounds of Formula 32a where the morpholinyl group is attached to the sulfur of the $SO_2$ group via the ring nitrogen.

In yet another aspect, the invention provides compounds of Formula 33, i.e., compounds according to any one of Formulas 27 up to and including 31s, wherein the heterocyclyl group (group A in Formula I) is thiomorpholinyl optionally substituted with one or more groups that are independently halogen, $C_1$-$C_6$ alkyl, $C_1$-$C_6$ alkoxy, haloalkyl, haloalkoxy, hydroxyl, CN, phenyloxy, benzyloxy, benzoyl, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of Formula 33a, i.e., compounds of Formula 33 where the thiomorpholinyl group is not attached to the sulfur of the $SO_2$ group via the ring nitrogen.

In still another aspect, the invention provides compounds of Formula 33b, i.e., compounds of Formula 33 where the thiomorpholinyl group is attached to the sulfur of the $SO_2$ group via the ring nitrogen.

In yet another aspect, the invention provides compounds of Formula 34, i.e., compounds according to any one of Formulas 27 up to and including 31s wherein the heterocyclyl group (group A in Formula I) is thiomorpholinyl S,S-dioxide optionally substituted with one or more groups that are independently halogen, $C_1$-$C_6$ alkyl, $C_1$-$C_6$ alkoxy, haloalkyl, haloalkoxy, hydroxyl, CN, phenyloxy, benzyloxy, benzoyl, —$SO_2$—($C_1$-$C_6$ alkyl), —NR'R", $C_1$-$C_6$ alkanoyl, pyridyl, phenyl, or —$SO_2$—NR'R", where each R' and R" is independently H or $C_1$-$C_6$ alkyl.

In still another aspect, the invention provides compounds of Formula 34a, i.e., compounds of Formula 34 where the thiomorpholinyl S,S-dioxide group is not attached to the sulfur of the SO₂ group via the ring nitrogen.

In still another aspect, the invention provides compounds of Formula 34b, i.e., compounds of Formula 34 where the thiomorpholinyl S,S-dioxide group is attached to the sulfur of the SO₂ group via the ring nitrogen.

In yet another aspect, the invention provides compounds of Formula 35, i.e., compounds according to any one of Formulas 27 up to and including 31s, wherein the heterocyclyl group (group A in Formula I) is piperidinyl optionally substituted with one or more groups that are independently halogen, $C_1$-$C_6$ alkyl, $C_1$-$C_6$ alkoxy, haloalkyl, haloalkoxy, hydroxyl, CN, phenyloxy, benzyloxy, benzoyl, —SO₂—($C_1$-$C_6$ alkyl), —NR'R", $C_1$-$C_6$ alkanoyl, pyridyl, phenyl, or —SO₂—NR'R", where each R' and R" is independently H or $C_1$-$C_6$ alkyl.

In still another aspect, the invention provides compounds of Formula 35a, i.e., compounds of Formula 35 where the piperidinyl group is not attached to the sulfur of the SO₂ group via the ring nitrogen.

In still another aspect, the invention provides compounds of Formula 35b, i.e., compounds of Formula 35 where the piperidinyl group is attached to the sulfur of the SO₂ group via the ring nitrogen.

In yet another aspect, the invention provides compounds of Formula 36, i.e., compounds according to any one of Formulas 27 up to and including 31s, wherein the heterocyclyl group (group A in Formula I) is piperazinyl optionally substituted with one or more groups that are independently halogen, $C_1$-$C_6$ alkyl, $C_1$-$C_6$ alkoxy, haloalkyl, haloalkoxy, hydroxyl, CN, phenyloxy, benzyloxy, benzoyl, —SO₂—($C_1$-$C_6$ alkyl), —NR'R", $C_1$-$C_6$ alkanoyl, pyridyl, phenyl, or —SO₂—NR'R", where each R' and R" is independently H or $C_1$-$C_6$ alkyl.

In still another aspect, the invention provides compounds of Formula 36a, i.e., compounds of Formula 36 where the piperazinyl group is not attached to the sulfur of the SO₂ group via the ring nitrogen.

In still another aspect, the invention provides compounds of Formula 36b, i.e., compounds of Formula 36 where the piperazinyl group is attached to the sulfur of the SO₂ group via the ring nitrogen.

In another aspect, the invention provides compounds of Formula 36c, i.e., compounds according to any one of Formulas 27 up to and including 36b, having the formula:

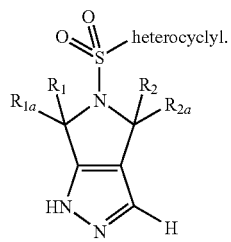

In another aspect, the invention provides compounds of Formula 36d, i.e., compounds according to any one of Formulas 27 up to and including 36b, having the formula:

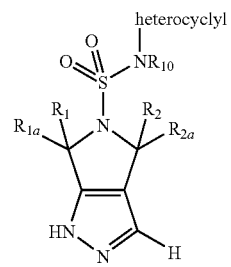

In another aspect, the invention provides compounds of Formula 36e, i.e., compounds according to any one of Formulas 27 up to and including 36b, having the formula:

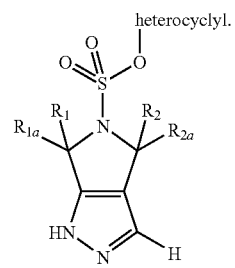

In still another aspect, the invention provides compounds of Formula 37, i.e., compounds of Formula I having the following formula:

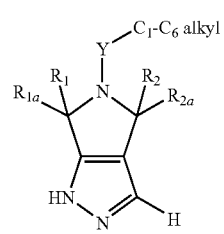

Formula 37 wherein,
the $C_1$-$C_6$ alkyl group is optionally substituted at a substitutable position with halogen, $C_1$-$C_6$ alkoxy, haloalkyl, haloalkoxy, hydroxyl, CN, aryloxy (e.g., phenyloxy), benzyloxy, benzoyl, —SO₂—($C_1$-$C_6$ alkyl), —NR'R", $C_1$-$C_6$ alkanoyl, pyridyl, phenyl, or —SO₂—NR'R";
$R_1$, $R_{1a}$, $R_2$, and $R_{2a}$, are independently hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, $C_1$-$C_6$ haloalkyl, aryl, aryl$C_1$-$C_6$ alkyl, heteroaryl, heterocyclyl, —C(O)OR', —CONR'R", $C_1$-$C_6$ haloalkyl, $C_1$-$C_4$ haloalkoxyalkyl, hydroxy $C_1$-$C_6$ alkyl, $C_1$-$C_6$ alkoxy, $C_2$-$C_6$ alkanoyl, aryloxy$C_1$-$C_6$ alkyl, heteroaryloxy $C_1$-$C_6$ alkyl, —$C_0$-$C_6$ alkyl-OC(O)NR'R", —$C_0$-$C_6$ alkyl-NR'R", hydroxyl, CN, or —$C_0$-$C_6$ alkyl-OC(O)-heterocyclyl, wherein each aryl, heteroaryl, and heterocyclyl group is optionally substituted with one or more groups that are independently halogen, $C_1$-$C_6$ alkyl, $C_1$-$C_6$ alkoxy, $C_1$-$C_6$alkanoyl, halo $C_1$-$C_4$ alkyl, halo$C_1$-$C_4$ alkoxy, —C(O)NR'R", —NR'R", hydroxyl, CN, or —C(O)OR'; or
$R_1$ and $R_{1a}$, or $R_2$ and $R_{2a}$ together with the carbon to which they are attached form $C_3$-$C_6$ cycloalkyl group wherein one of the carbons is optionally replaced with a heteroatom selected from N, O or S and wherein said ring may be optionally substituted with $C_1$-$C_6$ alkyl; or $R_1$ and $R_{1a}$, or $R_2$ and $R_{2a}$ together with the carbon to which they are attached form an oxo group; and R' and R" are independently H or $C_1$-$C_6$ alkyl; or R' and R" together with the atom to which they are attached may form a 3-8 membered ring optionally including an additional heteroatom such as N, O or S.

In yet another aspect, the invention provides compounds of Formula 38, i.e., compounds of Formula 37, wherein $R_1$ is hydrogen, $C_1$-$C_6$ alkyl, $C_3$-$C_6$cycloalkyl, $C_3$-$C_6$cycloalkylalkyl, halo $C_1$-$C_4$ alkyl, halo $C_1$-$C_4$ alkoxy, —C(O)NR'R", —NR'R", hydroxyl, hydroxy $C_1$-$C_4$ alkyl, CN, or —C(O)OR', and $R_{1a}$ and $R_{2a}$ are both H.

In yet another aspect, the invention provides compounds of Formula 38a, i.e., compounds of Formula 37, wherein $R_1$ is heteroaryl. In one embodiment, $R_1$ is 1,2,4-oxadiazolyl; 1,3,4-oxadiazolyl; furanyl; pyridyl or thienyl; each of which is optionally substituted with one or more groups that are independently halogen, $C_1$-$C_6$ alkyl, $C_1$-$C_6$ alkoxy, $C_1$-$C_6$ alkanoyl, halo $C_1$-$C_4$ alkyl, halo $C_1$-$C_4$ alkoxy, —C(O)NR'R", —NR'R", hydroxyl, CN, or —C(O)OR', where R' and R" are independently H or $C_1$-$C_6$ alkyl, or R' and R" together with the atom to which they are attached form a 3-6 membered ring.

In another aspect, the invention provides compounds of Formula 38b, i.e., compounds of Formula 37, wherein $R_1$ is 1,2,4-oxadiazolyl; 1,3,4-oxadiazolyl; furanyl; pyridyl or thienyl; each of which is substituted with at least one group that is halogen, $C_1$-$C_4$ alkyl, $C_1$-$C_4$ alkoxy, $C_2$-$C_4$ alkanoyl, halo $C_1$-$C_4$ alkyl, halo $C_1$-$C_4$ alkoxy, —C(O)NR'R", —NR'R", hydroxyl, —C(O)OR', where R' and R" are independently H or $C_1$-$C_4$ alkyl.

In another aspect, the invention provides compounds of Formula 38c, i.e., compounds of Formula 37, wherein $R_1$ is 1,2,4-oxadiazolyl; 1,3,4-oxadiazolyl; furanyl; pyridyl or thienyl; each of which is unsubstituted.

In yet another aspect, the invention provides compounds of Formula 38d, i.e., compounds of Formula 37, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$cycloalkyl, or $C_3$-$C_6$cycloalkyl$C_1$-$C_6$ alkyl; and $R_{1a}$ and $R_{2a}$ are both H.

In another aspect, the invention provides compounds of Formula 38e, i.e., compounds of Formula 37, wherein $R_1$ is hydrogen, $C_1$-$C_4$ alkyl, $C_1$-$C_4$ haloalkyl, $C_1$-$C_4$ alkoxy; $C_1$-$C_4$ haloalkoxy, or $C_3$-$C_6$ cycloalkyl, and $R_{1a}$ and $R_{2a}$ are both H.

In another aspect, the invention provides compounds of Formula 38f, i.e., compounds of Formula 37, wherein $R_1$ and $R_2$ are hydrogen, $C_1$-$C_4$ alkyl, $C_1$-$C_4$ haloalkyl, $C_1$-$C_4$ haloalkoxy, or $C_3$-$C_6$ cycloalkyl; and $R_{1a}$ and $R_{2a}$ are both H. In one embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is H. In another embodiment, $R_1$ is hydrogen, $C_1$-$C_4$ alkyl, $C_1$-$C_4$ haloalkyl, $C_1$-$C_4$ haloalkoxy, or $C_3$-$C_6$ cycloalkyl and $R_2$ is methyl, ethyl, propyl, isopropyl or cyclopropyl. In still another embodiment, $R_1$ is methyl, ethyl, propyl, isopropyl or cyclopropyl and $R_2$ is hydrogen, $C_1$-$C_4$ alkyl, $C_1$-$C_4$ haloalkyl, $C_1$-$C_4$ haloalkoxy, or $C_3$-$C_6$cycloalkyl. In a further embodiment, $R_1$ and $R_2$ are both methyl, ethyl, isopropyl, or cyclopropyl. In a further embodiment, $R_1$ and $R_2$ are both ethyl. In a further embodiment, $R_1$ and $R_2$ are both cyclopropyl. $R_1$ and $R_2$ may be cis or trans relative to each other.

In yet another aspect, the invention provides compounds of Formula 39, i.e., compounds according to any one of Formulas 37, 38, 38a, 38b, 38c, 38d, or 38e, wherein $R_2$ is hydrogen, $C_1$-$C_6$ alkyl, $C_2$-$C_6$ alkenyl, $C_2$-$C_6$ alkynyl, $C_3$-$C_6$cycloalkyl, $C_3$-$C_6$cycloalkyl$C_1$-$C_6$ alkyl, phenyl, phenyl$C_1$-$C_6$ alkyl, wherein each phenyl group is optionally substituted with 1, 2, 3, 4, or 5 groups that are independently halogen, $C_1$-$C_6$ alkyl, $C_1$-$C_6$ alkoxy, $C_1$-$C_6$alkanoyl, halo $C_1$-$C_4$ alkyl, halo $C_1$-$C_4$ alkoxy, —C(O)NR'R", —NR'R", hydroxyl, CN, or —C(O)OR'.

In yet another aspect, the invention provides compounds of Formula 39a, i.e., compounds according to any one of Formulas 37, 38, 38a, 38b, 38c, 38d, or 38e, wherein $R_2$ is hydrogen, $C_1$-$C_4$ alkyl, $C_1$-$C_4$ haloalkyl, $C_1$-$C_4$ alkoxy; $C_1$-$C_4$ haloalkoxy, $C_1$-$C_4$ haloalkoxyalkyl, hydroxy $C_1$-$C_6$ alkyl, $C_2$-$C_6$ alkanoyl, $C_3$-$C_6$cycloalkyl, or $C_3$-$C_6$cycloalkyl$C_1$-$C_6$ alkyl.

In yet another aspect, the invention provides compounds of Formula 39b, i.e., compounds according to any one of Formulas 37, 38, 38a, 38b, 38c, 38d, or 38e, wherein $R_2$ is hydrogen, $C_1$-$C_4$ alkyl, $C_3$-$C_6$ cycloalkyl, $C_1$-$C_4$ haloalkyl, $C_1$-$C_4$ alkoxy, or $C_1$-$C_4$ haloalkoxy, and $R_1$, $R_{1a}$ and $R_{2a}$ are independently hydrogen or $C_1$-$C_6$ alkyl.

In yet another aspect, the invention provides compounds of Formula 39c, i.e., compounds according to any one of Formulas 37, 38, 38a, 38b, 38c, 38d, or 38e, wherein $R_2$ is hydrogen, $C_1$-$C_4$ alkyl, $C_1$-$C_4$ haloalkyl, or $C_3$-$C_6$cycloalkyl.

In another aspect, the invention provides compounds of Formula 39d, i.e. compounds according to Formula 37, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is —C(O)OR', R' is $C_1$-$C_6$ alkyl and $R_{1a}$ and $R_{2a}$ are hydrogen.

In another aspect, the invention provides compounds of Formula 39e, i.e. compounds of Formula 37 or 38a, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is heteroaryl and $R_{1a}$ and $R_{2a}$ are hydrogen.

In another aspect, the invention provides compounds of Formula 39f, i.e., compounds of Formula 37, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is 1,2,4-oxadiazolyl or 1,3,4-oxadiazolyl, and $R_{1a}$ and $R_{2a}$ are hydrogen.

In another aspect, the invention provides compounds of Formula 39g, i.e., compounds of Formula 37 or 38a, wherein $R_2$ is hydrogen, $C_1$-$C_6$ alkyl, $C_3$-$C_6$ cycloalkyl, $C_1$-$C_6$ haloalkyl, $C_1$-$C_6$ alkoxy, or $C_1$-$C_6$ haloalkoxy, $R_1$ is furanyl, pyridyl or thienyl, and $R_{1a}$ and $R_{2a}$ are hydrogen.

In another aspect, the invention provides compounds of Formula 40c, i.e., compounds of Formula 37, wherein $R_1$ and $R_2$ are both $C_1$-$C_2$ haloalkyl and $R_{1a}$ and $R_{2a}$ are both H. $R_1$ and $R_2$ may be cis or trans relative to each other. In one embodiment, $R_1$ and $R_2$ are —$CH_2F$, —$CH_2CF_3$, —$CH_2CHF_2$, $CF_3$, or —$CF_2CH_3$.

In yet still another aspect, the invention provides compounds of Formula 40d, i.e., compounds of Formula 37, wherein, $R_1$, $R_{1a}$ and $R_{2a}$ are hydrogen and $R_2$ is $C_3$, $C_4$, $C_5$, or $C_6$-cycloalkyl.

In yet another aspect, the invention provides compounds of Formula 40e, i.e., compounds of Formula 37 wherein, $R_{1a}$ and $R_{2a}$ are hydrogen and $R_1$ and $R_2$ are $C_3$, $C_4$, $C_5$, or $C_6$ cycloalkyl. In one embodiment one of $R_1$ and $R_2$ is $C_3$-cycloalkyl. In another embodiment, $R_1$ and $R_2$ are $C_3$-cycloalkyl.

In yet another aspect, the invention provides compounds of Formula 40f, i.e., compounds of Formula 37 wherein, where, $R_{1a}$ and $R_{2a}$ are hydrogen, $R_1$ is methyl, ethyl, propyl or isopropyl, and $R_2$ is $C_3$, $C_4$, $C_5$, or $C_6$-cycloalkyl. In one embodiment $R_1$ is ethyl and $R_2$ is $C_3$, $C_4$, $C_5$, or $C_6$-cycloalkyl. In one embodiment, $R_2$ is $C_3$-cycloalkyl.

In another aspect, the invention provides compounds of Formula 40g, i.e., compounds of Formula 37, where, $R_{1a}$ and $R_{2a}$ are hydrogen, $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 40h, i.e., compounds of Formula 40g, wherein $R_2$ is $C_3$, $C_5$, or $C_6$ cycloalkyl. In one embodiment, $R_2$ is cyclopropyl.

In an aspect, the invention provides compounds of Formula 40i, i.e., compounds of Formula 40g, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 40j, i.e., compounds of Formula 40g, wherein $R_2$ is $C_1$-$C_4$ hydroxyalkyl. In one embodiment, $R_2$ is $CH_2OH$.

In an aspect, the invention provides compounds of Formula 40k, i.e., compounds of Formula 40g, wherein $R_2$ is H or $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 40l, i.e., compounds of Formula 37, wherein $R_{1a}$ and $R_{2a}$ are hydrogen and $R_1$ is $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 40m, i.e., compounds of Formula 40l, wherein $R_2$ is H.

In an aspect, the invention provides compounds of Formula 40n, i.e., compounds of Formula 40l, wherein $R_2$ is $C_3$, $C_5$, or $C_6$ cycloalkyl. In one embodiment, $R_2$ is cyclopropyl.

In an aspect, the invention provides compounds of Formula 40o, i.e., compounds of Formula 40l, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 40p, i.e., compounds of Formula 40l, wherein $R_2$ is $C_1$-$C_4$ hydroxyalkyl. In one embodiment, $R_2$ is $CH_2OH$.

In an aspect, the invention provides compounds of Formula 40q, i.e., compounds of Formula 37, wherein $R_{1a}$, $R_{2a}$, and $R_1$ are hydrogen In an aspect, the invention provides compounds of Formula 40r, i.e., compounds of Formula 40q, wherein $R_2$ is H.

In an aspect, the invention provides compounds of Formula 40s, i.e., compounds of Formula 40q, wherein $R_2$ is $C_3$, $C_5$, or $C_6$ cycloalkyl. In one embodiment, $R_2$ is cyclopropyl.

In an aspect, the invention provides compounds of Formula 40t, i.e., compounds of Formula 40q, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 40u, i.e., compounds of Formula 40q, wherein $R_2$ is $C_1$-$C_4$ hydroxyalkyl. In one embodiment, $R_2$ is $CH_2OH$.

In an aspect, the invention provides compounds of Formula 40v, i.e., compounds of Formula 37, wherein $R_{1a}$ and $R_{2a}$ are hydrogen and $R_1$ is $C_1$-$C_4$ hydroxyalkyl. In one embodiment, $R_1$ is $CH_2OH$.

In an aspect, the invention provides compounds of Formula 40w, i.e., compounds of Formula 40v, wherein $R_2$ is $C_1$-$C_4$ hydroxyalkyl. In one embodiment, $R_2$ is $CH_2OH$.

In an aspect, the invention provides compounds of Formula 40x, i.e., compounds of Formula 40v, wherein $R_2$ is $C_3$, $C_5$, or $C_6$ cycloalkyl. In one embodiment, $R_2$ is cyclopropyl.

In an aspect, the invention provides compounds of Formula 40y, i.e., compounds of Formula 40v, wherein $R_2$ is $C_1$-$C_4$ haloalkyl. In one embodiment, $R_2$ is $CF_3$. In another embodiment, $R_2$ is $CH_2$—F or $CH_2$—Cl.

In an aspect, the invention provides compounds of Formula 40z, i.e., compounds of Formula 37, wherein $R_{1a}$ and $R_{2a}$ are hydrogen and $R_1$ is $C_1$-$C_4$ haloalkyl. In one embodiment, $R_1$ is $CF_3$, $CH_2F$ or $CH_2Cl$. In another embodiment, $R_1$ is $CF_3$. In yet another embodiment, $R_1$ is $CH_2F$.

In an aspect, the invention provides compounds of Formula 40z1, i.e., compounds of Formula 40z, wherein $R_2$ is H.

In an aspect, the invention provides compounds of Formula 40z2, i.e., compounds of Formula 40z, wherein $R_2$ is $C_3$, $C_5$, or $C_6$ cycloalkyl. In one embodiment, $R_2$ is cyclopropyl.

In an aspect, the invention provides compounds of Formula 40z3, i.e., compounds of Formula 40z, wherein $R_2$ is $C_1$-$C_4$ haloalkyl. In one embodiment, $R_2$ is $CF_3$. In another embodiment, $R_2$ is $CH_2$—F or $CH_2$—Cl.

In another aspect, the invention provides compounds of Formula 40z4, i.e., compounds of Formula 37, where, $R_{1a}$ and $R_{2a}$ are hydrogen, $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In an aspect, the invention provides compounds of Formula 40z5, i.e., compounds of Formula 40z4, wherein $R_1$ is $C_3$, $C_5$, or $C_6$ cycloalkyl. In one embodiment, $R_1$ is cyclopropyl.

In an aspect, the invention provides compounds of Formula 40z6, i.e., compounds of Formula 40z4, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 40z7, i.e., compounds of Formula 40z4, wherein $R_1$ is $C_1$-$C_4$ hydroxyalkyl. In one embodiment, $R_1$ is $CH_2OH$.

In an aspect, the invention provides compounds of Formula 40z8, i.e., compounds of Formula 40z4, wherein $R_1$ is H or $C_1$-$C_4$ alkyl. In one embodiment, $R_1$ is methyl or ethyl or n-propyl. In another embodiment, $R_1$ is methyl. In yet another embodiment, $R_1$ is ethyl.

In an aspect, the invention provides compounds of Formula 40z9, i.e., compounds of Formula 37, wherein $R_{1a}$ and $R_{2a}$ are hydrogen and $R_2$ is $C_1$-$C_4$ alkyl. In one embodiment, $R_2$ is methyl or ethyl or n-propyl. In another embodiment, $R_2$ is methyl. In yet another embodiment, $R_2$ is ethyl.

In an aspect, the invention provides compounds of Formula 40z10, i.e., compounds of Formula 40z9, wherein $R_1$ is H.

In an aspect, the invention provides compounds of Formula 40z11, i.e., compounds of Formula 40z9, wherein $R_1$ is $C_3$, $C_5$, or $C_6$ cycloalkyl. In one embodiment, $R_1$ is cyclopropyl.

In an aspect, the invention provides compounds of Formula 40z12, i.e., compounds of Formula 40z9, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 40z13, i.e., compounds of Formula 40z9, wherein $R_1$ is $C_1$-$C_4$ hydroxyalkyl. In one embodiment, $R_1$ is $CH_2OH$.

In an aspect, the invention provides compounds of Formula 40z14, i.e., compounds of Formula 37, wherein $R_{1a}$, $R_{2a}$, and $R_2$ are hydrogen In an aspect, the invention provides compounds of Formula 40z15, i.e., compounds of Formula 40z14, wherein $R_1$ is $C_3$, $C_5$, or $C_6$ cycloalkyl. In one embodiment, $R_1$ is cyclopropyl.

In an aspect, the invention provides compounds of Formula 40z16, i.e., compounds of Formula 40z14, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 40z17, i.e., compounds of Formula 40z14, wherein $R_1$ is $C_1$-$C_4$ hydroxyalkyl. In one embodiment, $R_1$ is $CH_2OH$.

In an aspect, the invention provides compounds of Formula 40z18, i.e., compounds of Formula 37, wherein $R_{1a}$ and $R_{2a}$ are hydrogen and $R_2$ is $C_1$-$C_4$ hydroxyalkyl. In one embodiment, $R_2$ is $CH_2OH$.

In an aspect, the invention provides compounds of Formula 40z19, i.e., compounds of Formula 40z18, wherein $R_1$ is $C_1$-$C_4$ hydroxyalkyl. In one embodiment, $R_1$ is $CH_2OH$.

In an aspect, the invention provides compounds of Formula 40z20, i.e., compounds of Formula 40z18, wherein $R_1$ is $C_3$, $C_5$, or $C_6$ cycloalkyl. In one embodiment, $R_1$ is cyclopropyl.

In an aspect, the invention provides compounds of Formula 40z21, i.e., compounds of Formula 40z18, wherein $R_1$ is $C_1$-$C_4$ haloalkyl. In one embodiment, $R_1$ is $CF_3$. In another embodiment, $R_1$ is $CH_2$—F or $CH_2$—Cl.

In an aspect, the invention provides compounds of Formula 40z22, i.e., compounds of Formula 37, wherein $R_{1a}$ and $R_{2a}$ are hydrogen and $R_2$ is $C_1$-$C_4$ haloalkyl. In one embodiment, $R_2$ is $CF_3$, $CH_2F$ or $CH_2Cl$. In another embodiment, $R_2$ is $CF_3$. In yet another embodiment, $R_2$ is $CH_2F$.

In an aspect, the invention provides compounds of Formula 40z23, i.e., compounds of Formula 40z22, wherein $R_1$ is H.

In an aspect, the invention provides compounds of Formula 40z24, i.e., compounds of Formula 40z22, wherein $R_1$ is $C_3$, $C_5$, or $C_6$ cycloalkyl. In one embodiment, $R_1$ is cyclopropyl.

In an aspect, the invention provides compounds of Formula 40z25, i.e., compounds of Formula 40z22, wherein $R_1$ is $C_1$-$C_4$ haloalkyl. In one embodiment, $R_1$ is $CF_3$. In another embodiment, $R_1$ is $CH_2$—F or $CH_2$—Cl.

In yet still another aspect, the invention provides compounds of Formula 41, i.e., compounds of Formula 37, wherein $R_2$ and $R_{2a}$ combine to form oxo or $C_3$-$C_6$cycloalkyl.

In still another aspect, the invention provides compounds of Formula 41a, i.e., compounds of Formula 41 where, $R_1$ is H, $C_1$-$C_4$ alkyl, or $C_3$-$C_6$ cycloalkyl, and $R_{1a}$ is H.

In still another aspect, the invention provides compounds of Formula 41b, i.e., compounds of Formulas 41 or 41a where, $R_1$ is H, methyl, ethyl or isopropyl. In one embodiment, $R_1$ is H. In another embodiment, $R_1$ is methyl or ethyl.

In yet another aspect, the invention provides compounds of Formula 41c, i.e., compounds of Formulas 41, or 41a where, $R_1$ is $C_3$, $C_4$, $C_5$, or $C_6$ cyclolakyl. In one embodiment, $R_1$ is $C_3$-cycloalkyl.

In yet another aspect, the invention provides compounds of Formula 41d, i.e., compounds of Formula 41, wherein $R_2$ and $R_{2a}$ combine to form oxo, and $R_1$ and $R_{1a}$ are hydrogen.

In yet another aspect, the invention provides compounds of Formula 41e, i.e., compounds of Formula 41, wherein $R_2$ and $R_{2a}$ combine to form cyclopropyl, and $R_1$ and $R_{1a}$ are hydrogen.

In one aspect, the invention provides compounds of Formula 41f, i.e., compounds of Formula 37, wherein $R_2$ and $R_{2a}$ combine to form oxo, and $R_{1a}$ is hydrogen.

In another aspect, the invention provides compounds of Formula 41g, i.e., compounds of Formula 41f, wherein $R_1$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 41h, i.e., compounds of Formula 41f, wherein $R_1$ is $C_1$-$C_4$ hydroxyalkyl. In one embodiment, $R_1$ is $CH_2OH$.

In another aspect, the invention provides compounds of Formula 41i, i.e., compounds of Formula 41f, wherein $R_1$ is $C_1$-$C_4$ haloalkyl. In one embodiment, $R_1$ is $CH_2F$ or $CH_2Cl$.

In yet still another aspect, the invention provides compounds of Formula 41j, i.e., compounds of Formula 37, wherein $R_1$ and $R_{1a}$ combine to form oxo or $C_3$-$C_6$cycloalkyl.

In still another aspect, the invention provides compounds of Formula 41k, i.e., compounds of Formula 41j where, $R_2$ is H, $C_1$-$C_4$ alkyl, or $C_3$-$C_6$ cycloalkyl, and $R_{2a}$ is H.

In still another aspect, the invention provides compounds of Formula 41l, i.e., compounds of Formulas 41j or 41k, where $R_2$ is H, methyl, ethyl or isopropyl. In one embodiment, $R_2$ is H. In another embodiment, $R_2$ is methyl or ethyl.

In yet another aspect, the invention provides compounds of Formula 41m, i.e., compounds of Formulas 41j or 41k, where $R_2$ is $C_3$, $C_4$, $C_5$, or $C_6$ cyclolakyl. In one embodiment, $R_2$ is $C_3$-cycloalkyl.

In yet another aspect, the invention provides compounds of Formula 41n, i.e., compounds of Formula 37, wherein $R_1$ and $R_{1a}$ combine to form oxo, and $R_2$ and $R_{2a}$ are hydrogen.

In yet another aspect, the invention provides compounds of Formula 41o, i.e., compounds of Formula 37, wherein $R_1$ and $R_{1a}$ combine to form cyclopropyl, and $R_2$ and $R_{2a}$ are hydrogen.

In one aspect, the invention provides compounds of Formula 41p, i.e., compounds of Formula 37, wherein $R_1$ and $R_{1a}$ combine to form oxo, and $R_{2a}$ is hydrogen.

In another aspect, the invention provides compounds of Formula 41q, i.e., compounds of Formula 41p, wherein $R_2$ is phenyl substituted with one halogen. In one embodiment, the phenyl is substituted at the 4-position. In another embodiment, the phenyl is substituted at the 3-position. In another embodiment, the halogen is F or Cl. In still another embodiment, it is F.

In another aspect, the invention provides compounds of Formula 41r, i.e., compounds of Formula 41p, wherein $R_2$ is $C_1$-$C_4$ hydroxyalkyl. In one embodiment, $R_2$ is $CH_2OH$.

In another aspect, the invention provides compounds of Formula 41s, i.e., compounds of Formula 41p, wherein $R_2$ is $C_1$-$C_4$ haloalkyl. In one embodiment, $R_2$ is $CH_2F$ or $CH_2Cl$.

In another aspect, the invention provides compounds of Formula 42, i.e., compounds according to any one of formulas 37 up to and including 41s, wherein the $C_1$-$C_6$ alkyl group (the A-group in formula I) is substituted with at least one group that is halogen, $C_1$-$C_6$ alkyl, $C_1$-$C_6$ alkoxy, $C_1$-$C_4$ haloalkyl, $C_1$-$C_4$ haloalkoxy, hydroxyl, CN, phenyloxy, benzyloxy, benzoyl, —$SO_2$—($C_1$-$C_6$ alkyl), —NR'R", $C_2$-$C_6$ alkanoyl, pyridyl, phenyl, or —$SO_2$—NR'R". In one embodiment, R' and R" are independently H or $C_1$-$C_6$ alkyl. In another embodiment, R' and R" together with the atom to which they are attached may form a 3-8 membered ring optionally including an additional heteroatom such as N, O or S.

In another aspect, the invention provides compounds of Formula 42a, i.e., compounds according to any one of formulas 37 up to and including 41s, wherein the $C_1$-$C_6$ alkyl group (the A-group in formula I) is substituted with at least one group that is halogen, $C_1$-$C_4$ alkoxy, $CF_3$, $OCF_3$, hydroxyl, CN, phenyloxy, or benzoyl.

In another aspect, the invention provides compounds of Formula 42b, i.e., compounds according to any one of formulas 37 up to and including 41s, wherein the $C_1$-$C_6$ alkyl group (the A-group in formula I) is substituted with phenyloxy or benzoyl.

In another aspect, the invention provides compounds of Formula 42c, i.e., compounds according to any one of formulas 37 up to and including 41s, wherein the $C_1$-$C_6$ alkyl group (the A-group in formula I) is unsubstituted.

In another aspect, the invention provides compounds of Formula 42d, i.e., compounds according to any one of formulas 37 up to and including 41s, wherein the $C_1$-$C_6$ alkyl group (the A-group in formula I) is selected from the group consisting of n-propyl, isopropyl, n-butyl, sec-butyl, iso-butyl, n-pentyl, iso-pentyl, neo-pentyl, n-hexyl, 4-methylpentyl, 3-methylpentyl, 2-methylpentyl, and hex-2-yl, each of which is optionally substituted with one or more groups that are independently selected from halogen, $C_1$-$C_4$ alkoxy, $CF_3$, $OCF_3$, hydroxyl, CN, phenyloxy and benzoyl.

In another aspect, the invention provides compounds of Formula 42e, i.e., compounds according to any one of formulas 37 up to and including 41s, wherein the $C_1$-$C_6$ alkyl group (the A-group in formula I) is methyl or ethyl, each of which is optionally substituted with 1 or 2 groups that are independently halogen, $C_1$-$C_6$ alkoxy, $C_1$-$C_4$ haloalkyl, $C_1$-$C_4$ haloalkoxy, hydroxyl, CN, phenyloxy, benzyloxy, benzoyl, —$SO_2$—($C_1$-$C_6$ alkyl), —NR'R", $C_2$-$C_6$ alkanoyl, pyridyl, phenyl, or —$SO_2$—NR'R".

In still yet another aspect, the invention provides compounds of Formula 43, i.e., compounds according to any one of Formulas 37 up to and including 42e, having the formula:

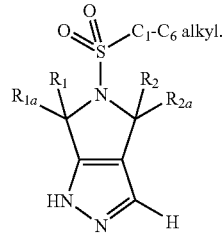

In still yet another aspect, the invention provides compounds of Formula 44, i.e., compounds according to any one of Formulas 37 up to and including 42e, having the formula:

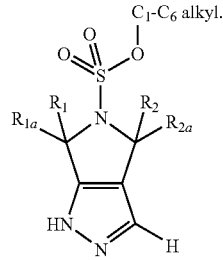

In still yet another aspect, the invention provides compounds of Formula 45, i.e., compounds according to any one of Formulas 37 up to and including 42e, having the formula:

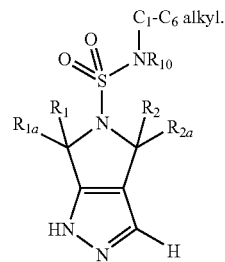

In another aspect, the invention provides compounds selected from:

4-ethyl-5-(4-(trifluoromethyl)phenylsulfonyl)-1,4,5,6-tetrahydropyrrolo[3,4-c]pyrazole;

4-cyclopropyl-5-(4-(trifluoromethyl)phenylsulfonyl)-1,4,5,6-tetrahydropyrrolo[3,4-c]pyrazole;

methyl 4-cyclopropyl-5-(4-(trifluoromethyl)phenylsulfonyl)-2,4,5,6-tetrahydropyrrolo[3,4-c]pyrazole-6-carboxylate;

methyl 4-(trifluoromethyl)-5-(4-(trifluoromethyl)phenylsulfonyl)-2,4,5,6-tetrahydropyrrolo[3,4-c]pyrazole-6-carboxylate;

4-cyclopropyl-6-(difluoromethyl)-5-(4-(trifluoromethyl)phenylsulfonyl)-2,4,5,6-tetrahydropyrrolo[3,4-c]pyrazole;

4-cyclopropyl-5-(4-(trifluoromethyl)phenylsulfonyl)-2,4,5,6-tetrahydropyrrolo[3,4-c]pyrazol-6-yl)methanol;

4-cyclopropyl-5-(4-(trifluoromethyl)phenylsulfonyl)-2,4,5,6-tetrahydropyrrolo[3,4-c]pyrazole-6-carbonitrile;

2-(4-cyclopropyl-5-(4-(trifluoromethyl)phenylsulfonyl)-2,4,5,6-tetrahydropyrrolo[3,4-c]pyrazol-6-yl)-1,3,4-oxadiazole;

5-(-4-cyclopropyl-5-(4-(trifluoromethyl)phenylsulfonyl)-2,4,5,6-tetrahydropyrrolo[3,4-c]pyrazol-6-yl)-1,2,4-oxadiazole; and stereoisomers, tautomers, mixtures of stereoisomers and/or tautomers or pharmaceutically acceptable salts thereof.

The following compounds were made according to the methods and procedures described herein.

| Name | (M + H)+ | 1H NMR |
|---|---|---|
| 5-(4-chlorophenylsulfonyl)-1,4,5,6-tetrahydropyrrolo[3,4-c]pyrazole | 284.0 | (CDCl$_3$) δ = 10.06 (b, 1H), 7.82 (d, J = 8.3 Hz, 2H), 7.50 (d, J = 8.3 Hz, 2H), 7.27 (s, 1H), 4.47 (m, 4H). |
| (R)-4-ethyl-5-(4-(trifluoromethyl)phenylsulfonyl)-1,4,5,6-tetrahydropyrrolo[3,4-c]pyrazole | 346.1 | (CDCl$_3$) δ 7.99 (d, J = 8.2 Hz, 2H), 7.77 (d, J = 8.2 Hz, 2H), 7.26 (s, 1H), 4.82 (m, 1H), 4.54 (dd, J = 13.5, 25.0 Hz, 2H), 2.09 (m, 1H), 1.86 (m, 1H), 0.90 (t, J = 7.2 Hz, 3H). |
| (R)-4-cyclopropyl-5-(4-(trifluoromethyl)phenylsulfonyl)-1,4,5,6-tetrahydropyrrolo[3,4-c]pyrazole | 358.1 | (CDCl$_3$) δ 8.02 (d, J = 8.6 Hz, 2H), 7.76 (d, J = 8.6 Hz, 2H), 7.28 (s, 1H), 4.81 (d, J = 6.2 Hz, 1H), 4.58 (dd, J = 13.4, 21.9 Hz, 2H), 1.38 (m, |

| Name | (M + H)+ | 1H NMR |
|---|---|---|
| 4,6-dicyclopropyl-5-(4-(trifluoromethyl)phenylsulfonyl)-1,4,5,6-tetrahydropyrrolo[3,4-c]pyrazole | 398.1 | 1H), 0.67-0.40 (m, 1H), 0.09 (m, 1H) (CDCl$_3$) δ 8.01 (d, J = 8.2 Hz, 2H), 7.71 (d, J = 8.2 Hz, 2H), 7.19 (s, 1H), 4.59 (d, J = 10.3 Hz, 1H), 4.57 (d, J = 10.3 Hz, 1H), 1.35 (m, 2H), .81 (m, 1H), 0.68-0.44 (m, 5H), (m, 1H), 0.31 (m, 1H), 0.19 (m, 1H |
| 4-cyclopropyl-5-(4-(trifluoromethyl)phenylsulfonyl)-4,5-dihydropyrrolo[3,4-c]pyrazol-6(1H)-one | 372.1 | (CDCl$_3$) δ 8.34 (d, J = 8.4 Hz, 2H), 7.83 (d, J = 8.4 Hz, 2H), 7.68 (s, 1H), 5.28 (d, J = 6.8 Hz, 1H), 2.64 (m, 1H), .83 (m, 2H), 0.42 (m, 1H), 0.07 (m, 1H) |
| 4-cyclopropyl-6-(fluoromethyl)-5-(4-(trifluoromethyl)phenylsulfonyl)-1,4,5,6-tetrahydropyrrolo[3,4-c]pyrazole | 390.1 | (CDCl$_3$) δ 7.99 (d, J = 8.3 Hz, 2H), 7.75 (d, J = 8.3 Hz, 2H), 7.23 (s, 1H), 5.01-4.90 (m, 1H), 4.81-4.74 (m, 1H), 4.65-4.61 (m, 1H), 4.59 (d, J = 7.4 Hz, 1H), 1.26-1.24 (m, 1H), 0.62-0.48 (m, 3H), 0.19-0.17 (m, 1H). |
| (R)-4-cyclopropyl-5-(4-(trifluoromethyl)phenylsulfonyl)-1,4,5,6-tetrahydropyrrolo[3,4-c]pyrazole | 358.1 | (CDCl$_3$) δ 8.02 (d, 2H, J = 8.6 Hz), 7.76 (d, 2H, J = 8.6 Hz), 7.28 (s, 1H), 4.81 (d, 1H, J = 6.2 Hz), 4.58 (dd, 2H, J = 13.4, 21.9 Hz), 1.38 (m, 1H), 0.67-0.40 (m, 1H), 0.09 (m, 1H) |
| ((4R)-4-cyclopropyl-5-(4-(trifluoromethyl)phenylsulfonyl)-1,4,5,6-tetrahydropyrrolo[3,4-c]pyrazol-6-yl)methanol | 388.1 | (CDCl$_3$) δ 7.99 (d, J = 8.2 Hz, 2H), 7.74 (d, J = 8.2 Hz, 2H), 7.19 (s, 1H), 4.76 (dd, J = 5.4, 5.1 Hz, 1H), 4.69 (d, J = 5.6 Hz, 1H), 3.99 (dd, J = 11.5, 5.4 Hz, 1H), 3.92 (dd, J = 11.5, 5.1 Hz, 1H), 1.25-1.20 (m, 1H), 0.93-0.79 (m, 1H), 0.56-0.44 (m, 2H), 0.14-0.04 (m, 1H). |
| 6-(4-fluorophenyl)-5-(4-(trifluoromethyl)phenylsulfonyl)-1,4,5,6-tetrahydropyrrolo[3,4-c]pyrazole | 412.1 | (CD$_3$OD) δ 7.93 (d, J = 8.2 Hz, 2H), 7.83 (d, J = 8.2 Hz, 2H), 7.37 (s, 1H), 7.31 (dd, J = 5.5 and 9.0 Hz, 2H), 6.97 (t, J = 9.0 Hz, 2H), 5.86 (s, 1H), 3.85 (s, 2H) |
| (S)-4-(4-fluorophenyl)-5-(4-(trifluoromethyl)phenylsulfonyl)-1,4,5,6-tetrahydropyrrolo[3,4-c]pyrazole | 412.1 | (CDCl$_3$) δ 7.61 (m, 4H), 7.18 (s, 1H), 7.12 (dd, J = 5.4, 8.6 Hz, 2H), 6.89 (t, J = 8.6 Hz, 1H), 5.94 (s, 1H), 4.79 (d, J = 12.8 Hz, 1H), 4.65 (d, J = 12.8 Hz, 1H) |
| (R)-4-(4-fluorophenyl)-5-(4-(trifluoromethyl)phenylsulfonyl)-1,4,5,6-tetrahydropyrrolo[3,4-c]pyrazole** | | |

**This compound may be prepared using the method used to prepare the (S)-isomer (immediately above in the table) but using (R)-allyl 2-diazo-5-(4-fluorophenyl)-5-(4-methylphenylsulfonamido)-3-oxopentanoate in place of (S)-allyl 2-diazo-5-(4-fluorophenyl)-5-(4-methylphenylsulfonamido)-3-oxopentanoate (see: Dong, C; et al. J. Org. Chem. 2008, 73(5), 1971.

The following compounds are made according to the methods and procedures described herein.

4-cyclopropyl-6-(4-fluorophenyl)-5-(4-(trifluoromethyl)phenylsulfonyl)-2,4,5,6-tetrahydropyrrolo[3,4-c]pyrazole;

4-cyclopropyl-6-(4-fluorophenyl)-5-(6-(trifluoromethyl)pyridin-3-ylsulfonyl)-2,4,5,6-tetrahydropyrrolo[3,4-c]pyrazole;

5-(4-chlorophenylsulfonyl)-4-cyclopropyl-6-(4-fluorophenyl)-2,4,5,6-tetrahydropyrrolo[3,4-c]pyrazole;

6-(4-fluorophenyl)-4-(trifluoromethyl)-5-(4-(trifluoromethyl)phenylsulfonyl)-2,4,5,6-tetrahydropyrrolo[3,4-c]pyrazole;

6-(4-fluorophenyl)-4-(trifluoromethyl)-5-(6-(trifluoromethyl)pyridin-3-ylsulfonyl)-2,4,5,6-tetrahydropyrrolo[3,4-c]pyrazole;

5-(4-chlorophenylsulfonyl)-6-(4-fluorophenyl)-4-(trifluoromethyl)-2,4,5,6-tetrahydropyrrolo[3,4-c]pyrazole;

6-cyclopropyl-4-(4-fluorophenyl)-5-(4-(trifluoromethyl)phenylsulfonyl)-2,4,5,6-tetrahydropyrrolo[3,4-c]pyrazole;

6-cyclopropyl-4-(4-fluorophenyl)-5-(6-(trifluoromethyl)pyridin-3-ylsulfonyl)-2,4,5,6-tetrahydropyrrolo[3,4-c]pyrazole;

5-(4-chlorophenylsulfonyl)-6-cyclopropyl-4-(4-fluorophenyl)-2,4,5,6-tetrahydropyrrolo[3,4-c]pyrazole;

4-(4-fluorophenyl)-6-(trifluoromethyl)-5-(6-(trifluoromethyl)pyridin-3-ylsulfonyl)-2,4,5,6-tetrahydropyrrolo[3,4-c]pyrazole;

5-(4-chlorophenylsulfonyl)-4-(4-fluorophenyl)-6-(trifluoromethyl)-2,4,5,6-tetrahydropyrrolo[3,4-c]pyrazole; and 4-(4-fluorophenyl)-6-(trifluoromethyl)-5-(4-(trifluoromethyl)phenylsulfonyl)-2,4,5,6-tetrahydropyrrolo[3,4-c]pyrazole.

In another aspect the invention provides a pharmaceutical composition comprising a compound or salt of Formula I and at least one pharmaceutically acceptable solvent, adjuvant, excipient, carrier, binder or disintegrant.

In another aspect, the invention provides a method of treating an A beta-related disease comprising administering a therapeutically effective amount of a compound or salt of Formula I to a patient in need of such treatment.

In another aspect, the invention provides a method of treating Alzheimer's disease, prodromal Alzheimer's disease, mild cognitive impairment, dementia, or Down's syndrome comprising administering a therapeutically effective amount of a compound or salt of Formula I to a patient in need of such treatment.

In another aspect, the invention provides a method of treating Alzheimer's disease, prodromal Alzheimer's disease, mild cognitive impairment, dementia, or Down's syndrome comprising administering to a patient in need of such treatment, a therapeutically effective amount of a combination of a compound or salt of Formula I and another therapeutic agent used to treat or prevent said conditions. Such agents include acetylcholine esterase inhibitors, A-beta aggregation inhibitors, glutamate inhibitors, anti-inflammatory agent, anti-oxidants, neurotropic agents, or other gamma or beta secretase inhibitors.

Definitions

The definitions and explanations below are for the terms as used throughout this entire document including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different. It will be understood by those skilled in the art with respect to any group containing one or more substituents that such groups are not intended to introduce any substitution or substitution patterns that are sterically impractical and/or synthetically non-feasable.

APP, amyloid precursor protein, is defined as any APP polypeptide, including APP variants, mutations, and isoforms, for example, as disclosed in U.S. Pat. No. 5,766,846. A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Pharmaceutically acceptable refers to those properties and/or substances that are acceptable to the patient from a toxicological and/or safety point of view.

A therapeutically effective amount is defined as an amount effective to reduce or lessen at least one symptom of the disease being treated or to reduce or delay onset of one or more clinical markers or symptoms of the disease.

By "alkanoyl" is meant an acyl radical Alk-C(O)—, wherein Alk is an alkyl radical as defined herein. Examples of alkanoyl include optionally substituted acetyl, propionyl, butyryl, isobutyryl, valeryl, isovaleryl, 2-methyl-butyryl, 2,2-dimethylpropionyl, valeryl, hexanoyl, heptanoyl, octanoyl and the like.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons. Alkyl groups may be diradicals; the meaning of the term will be clear from the context in which it is used. Alkyl groups may be substituted or unsubstituted.

By "alkylene" is meant a diradical alkyl group, whereby alkyl is as defined above By "alkoxy" and "$C_1$-$C_6$ alkoxy" in the present invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy. Alkoxy groups may be substituted or unsubstituted.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like. Alkenyl groups may be substituted or unsubstituted.

"Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like. Alkynyl groups may be substituted or unsubstituted.

By "aryl" is meant an aromatic carbocyclic group having a single ring (e.g., phenyl) or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. Aryl groups may be substituted or unsubstituted.

By "arylalkyl" or "aralkyl" is meant the group -alkylene-aryl, wherein alkylene and aryl are defined herein.

By "aryloxy" is meant the group —O-aryl wherein the term aryl is as defined herein.

By "arylalkyloxy" or "aralkyloxy" is meant the group —O—$C_{1-4}$-alkylene-aryl wherein the terms aryl and alkylene are as defined herein. An example of arylalkyloxy is benzyloxy (or —O—$CH_2$-phenyl).

By "cycloalkyl" is meant saturated or partially unsaturated carbocyclic radicals having three to twelve carbon atoms. The cycloalkyl can be monocyclic, a polycyclic fused system, or a bi or polycyclic bridged system, such as adamantyl or bicyclo[2.2.1]heptyl. Examples of such radicals include cyclopropyl, cyclobutyl, cyclopentyl and cyclohexyl. Preferred cycloalkyl groups are cyclopentyl, cyclohexyl, and cycloheptyl. Cycloalkyl groups may be substituted or unsubstituted.

By the term "halogen" or "halo" in the present invention is meant fluorine, bromine, chlorine, and/or iodine.

By "haloalkyl" is meant an alkyl radical having the meaning as defined above wherein one or more hydrogens are replaced by a halogen. Examples of such haloalkyls include chloromethyl, 1-bromoethyl, fluoromethyl, difluoromethyl, trifluoromethyl, 1,1,1-trifluoroethyl and the like.

By "heteroaryl" is mean at least one or more aromatic ring systems of 5-, 6-, or 7-membered rings which includes fused ring systems of 9-11 atoms containing at least one and up to four heteroatoms selected from nitrogen, oxygen, or sulfur. Heteroaryl groups of the present invention include pyridyl, pyrimidyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzopyrazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocumarinyl, dihydroisocumarinyl, isoindolinonyl, benzodioxanyl, benzoxazolinonyl, pyrrolyl N-oxide, pyrimidyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, benzothienyl, indolyl, pyridazinyl, pyrazinyl, isoindolyl, isoquinolyl, quinazolinyl, quinoxalinyl, imidazolyl, isoxazolyl, pyrazolyl, oxazolyl, thiazolyl, benzothiazolyl, benzimidazolyl, benzofuranyl, furanyl, thienyl, and pyrrolyl. More preferred heteroaryl groups include pyridyl, pyrimidyl, thienyl, pyrazolyl, oxazolyl, thiazolyl, and pyrrolyl. Still more preferred are pyridyl, pyrimidyl, thienyl, pyrrolyl and thiazolyl. Heteroaryl groups may be substituted or unsubstituted.

By "heterocycle" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidyl, dihydrofuryl, dihydropyranyl, tetrahydrothienyl S-oxide, tetrahydrothienyl S,S-dioxide and homothiomorpholinyl S-oxide. More preferred are piperidinyl, piperazinyl, pyrrolidinyl, morpholinyl, thiomorpholinyl, thiomorpholinyl S,S-dioxide, tetrahydrofuranyl, or imidazolidinyl. Heterocyclyl groups may be substituted or unsubstituted.

By "hydroxyalkyl" is meant an alkyl substituted with a hydroxyl, such as hydroxymethyl, 1-hydroxypropyl, 2-hydroxyethyl, 3-hydroxyethyl, or 3-hydroxybutyl.

Most compounds were named using Autonom 2000 4.01.305, which is available from Beilstein Information Systems, Inc, Englewood, Colo., or ChemDraw v. 9.0.1 or 10.0, (available from Cambridgesoft at 100 Cambridge Park Drive, Cambridge, Mass. 02140). Alternatively, the names were generated based on the IUPAC rules. The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formula I.

The invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

The term "acid prodrug group" denotes a moiety that is converted in vivo into an active carboxylic acid compound of Formula I. Such prodrug groups are generally known in the art and include ester forming groups, to form an ester prodrug, such as benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$-$C_6$) alkoxy optionally substituted by N-morpholino and amide-forming groups such as di($C_1$-$C_6$)alkylamino. Preferred prodrug groups include $C_1$-$C_6$ alkoxy forming an ester, and $O^-M^+$ where $M^+$ represents a cation to form a salt of the acid. Preferred cations include sodium, potassium, and ammonium. Other cations include magnesium and calcium. Further preferred prodrug groups include $O^-M^{++}$ where $M^{++}$ is a divalent cation such as magnesium or calcium.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvates, such as water, ethanol, mineral oil, vegetable oil, and dimethylsulfoxide.

The compounds of the invention can either be used individually or in combination, as is best for the patient. The compounds employed in the methods of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as ARICEPT® and rivastigmine (marketed as EXELON®); inhibitors of glutamate-mediated toxicity such as memantine (NAMENDA®), Flurizan, gamma-secretase inhibitors, for example, E-2012 and LY450139 and their hydrates and salts; anti-inflammatory agents such as cyclooxygenase II inhibitors; anti-oxidants such as Vitamin E, A-beta aggregation inhibitors such as tramiprosate and scyllo-inositol; and ginkolides; immunological approaches, such as, for example, immunization with A beta peptide or administration of anti-A beta peptide antibodies; statins; antiamyloid vaccines, neurotropic agents such as CEREBROLYSIN®, NEOTROFIN® (AIT-082), and other direct or indirect neurotropic agents of the future. Combinations of a gamma secretase inhibitor and one or more of the other agents of this paragraph may be contained within the same pharmaceutical dosage form or may be administered in separate dosages forms together or at desired intervals. It should be apparent to one skilled in the art that the exact dosage and frequency of administration will depend on the particular compounds employed in the methods of the invention administered, the particular condition being treated, the severity of the condition being treated, the age, weight, general physical condition of the particular patient, and other medication the individual may be taking as is well known to administering physicians who are skilled in this art.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, a flavoring agent (or agents) and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered via a transdermal device. Topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. A hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of the combination invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.5 mg to about 500 mg per kilogram of body weight per day are useful in the treatment of the above-indicated conditions. The amount of active ingredient that may be combined with the carrier materials to produce a single dosage form will vary depending upon the host treated and the particular mode of administration. Dosage unit forms will generally contain between from about 1 mg to about 100 mg of an active ingredient, more preferably from about 5 to about 30 mg of the active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a pre-mix for addition to the feed or drinking water.

The disclosures in this document of all articles and references, including patents, are incorporated herein by reference in their entirety.

The invention is illustrated further by the following examples, which are not to be construed as limiting the invention in scope or spirit to the specific procedures described in them.

The starting materials and various intermediates may be obtained from commercial sources, prepared from commercially available compounds, and/or prepared using known synthetic methods.

General Synthetic Procedures

The compounds of the invention can be prepared using methods known in the art of organic synthesis. Representative procedures for preparing compounds of the invention are outlined in the following schemes.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Second Edition, Wiley, New York, 1991, and references cited therein.

The chlorosulfates useful in preparing the sulfamates described herein (that is, where Y is —SO$_2$—O— or where —SO$_2$—O— intervenese between the pyrrolidine ring and the A-group), may be prepared using methods disclosed in Buncel, Erwin., "Chlorosulfates" Chemical Reviews (1970) Vol. 70, No. 3, pp. 323-337, as well as other methods known in the art. The sulfamides useful in preparing the sulfamides described herein (that is, where Y is —SO$_2$—NR$_{10}$— or where —SO$_2$—NR$_{10}$— intervenese between the pyrrolidine ring and the A-group), may be prepared using methods known in the art. See, for example, McDermott, Sean D.; Spillane, William J. Synthesis and reactions of sulfamides. A review. Organic Preparations and Procedures International (1984), 16(1), 49-77.

Certain Abbreviations Used Throughout the Specification have the Following Meanings:
t-Boc refers to N-tert-butoxycarbonyl
conc. refers to concentrated.
DCM refers to dichloromethane.
Dess-Martin periodinane refers to 1,1,1-triacetoxy-1,1-dihydro-1,2-benziodoxol-3(1H)-one.
DMAP refers to dimethylaminopyridine.
DMF refers to dimethyl formamide.
DMF-DMA refers to dimethyl formamide dimethylacetal.
DMSO refers to dimethylsulfoxide.
Et$_2$O or ether refers to diethyl ether.
EtOAc refers to ethyl acetate.
HPLC refers to high pressure liquid chromatography.
IC$_{50}$ refers to the molar concentration of a drug, which produces 50% of the maximum possible inhibition for that drug.
LCMS refers to liquid chromatography/mass spectrometer.
MeOH refers to methanol.
MNNG refers to 1-methyl-3-nitro-1-nitrosoguanidine.
MS stands for mass spectrum.
m/z refers to mass to charge ratio.
NMR refers to nuclear magnetic resonance.
NaHMDS refers to sodium hexamethyldisilazane.
H$_5$IO$_6$ refers to periodic acid.
RT refers to room temperature.
sat. refers to saturated.
TBSCl refers to t-Butyldimethylsilyl chloride.
THF refers to tetrahydrofuran.
TEA refers to triethylamine.
TFA refers to trifluoroacetic acid.

Scheme 1:

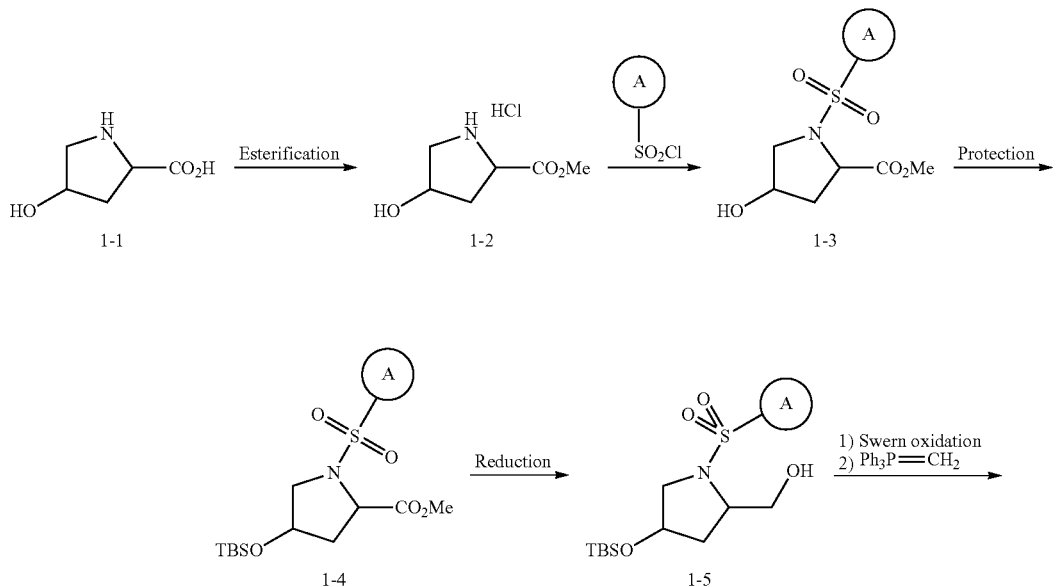

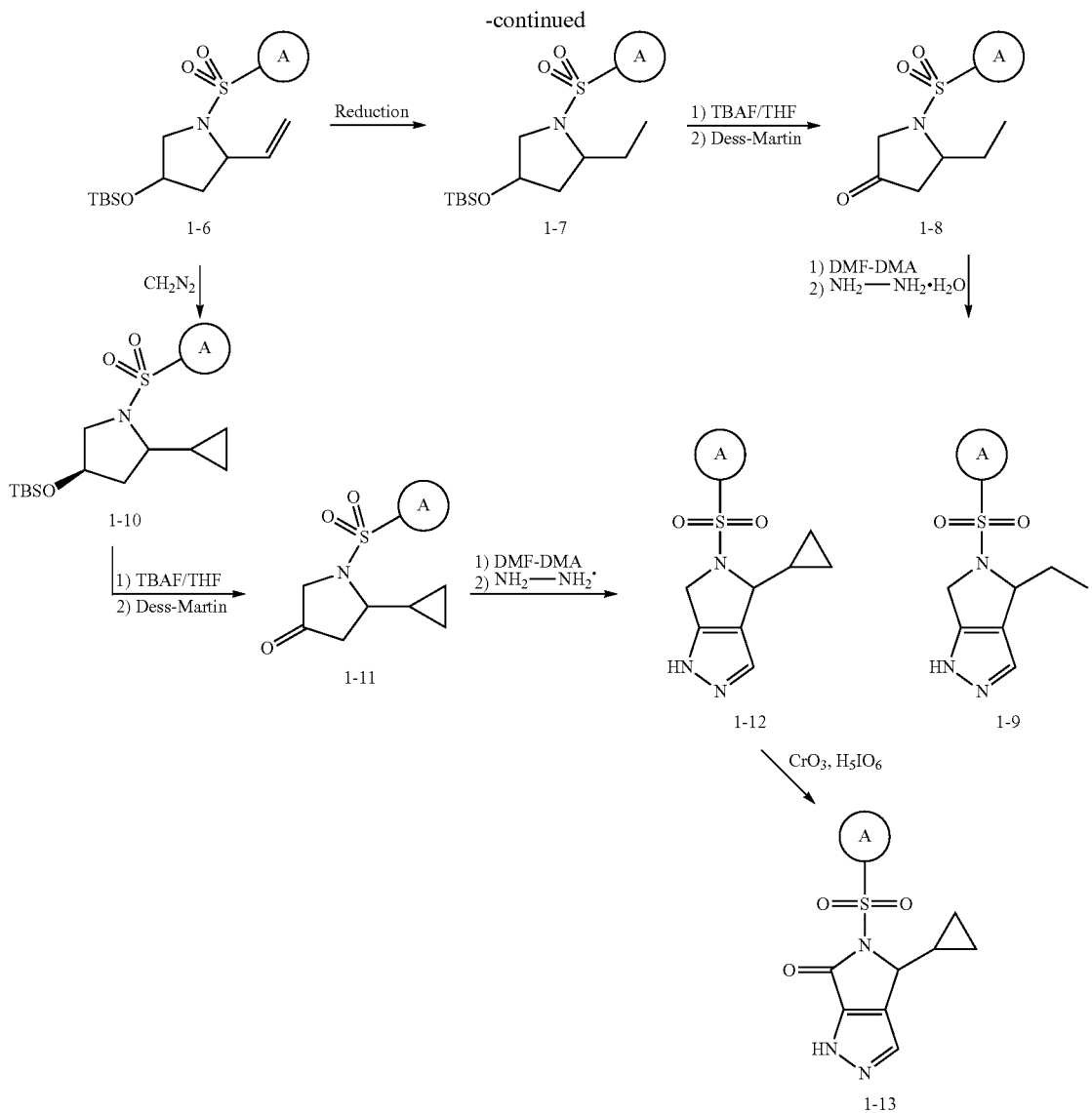

In the above scheme, A is defined as described for Formula I. One of ordinary skill in the art will appreciate that the above scheme can be used to selectively produce a single diastereomer and/or a single enantiomer.

The preparation of chiral 2-alkyl-4-pyrrolidinones has been described in: Chang M. Y. et al, *Heterocycles*, 65(7), 1705-1711 (2005). Esterification of 4-hydroxypyrrolidine-2-carboxylic acid 1-1, and sulfonation with a sulfonylchloride of formula A-SO$_2$Cl wherein A is as defined above, in the presence of a base such as triethylamine, may give compound 1-3. Protection of the hydroxyl group of compound 1-3 for example silylation with tert-butyldimethylsilyl chloride, may give compound of formula 1-4, which after reduction of the ester group my give compound of formula 1-5. Swern oxidation with DMSO and oxalyl chloride, followed by the introduction of a methylene group using the Wittig reagent methylenetriphenylphosphorane (Ph$_3$P=CH$_2$) may give compound of formula 1-6. The allyl group of compound 1-6 may be reduced by ways well known in the art, such as hydrogen with Pd(C) to give a compound 1-7. Removal of the silyl group followed by oxidation of the hydroxyl group, with, for example Dess-Martin periodinane may give compound 1-8. Compounds of Formula 1-9 can be made by treatment of the 3-oxopyrrolidine 1-8 with acylating agents such as dimethylformamide dimethyl acetal, ethyl formate, or dimethylacetamide dimethyl acetal followed by cyclization with hydrazines in a suitable solvent such as acetic acid.

Alternatively, compound 1-6 may be treated with diazomethane to give the cyclopropyl compound 1-10, which after removal of the protective silyl group and oxidation may give the compound of formula 1-11. As described for compound 1-8 above, treatment with an acylating agent followed by cyclization with hydrazines may give compounds of formula 1-12. Additionally compounds of formula 1-12 may be oxidized with chromium trioxide and periodic acid to form compounds of formula 1-13.

In Scheme 2 below, A and R$_2$ contain the definitions as described above. One of ordinary skill in the art will appreciate that the above scheme can be used to selectively produce a single diastereomer and/or a single enantiomer.

The aldehyde 2-1 is treated with t-butylsulfinylamide in the presence of a Lewis acid under dehydrating conditions, for example in the presence of titanium alkoxides, preferably in the presence of Ti(OEt)$_4$, which is a Lewis acid with dehydrating conditions, as described by Liu, G.; et al. *J. Org. Chem.*, 64, 1278-1284 (1999), to give the sulfinylimine of Formula 2-2.

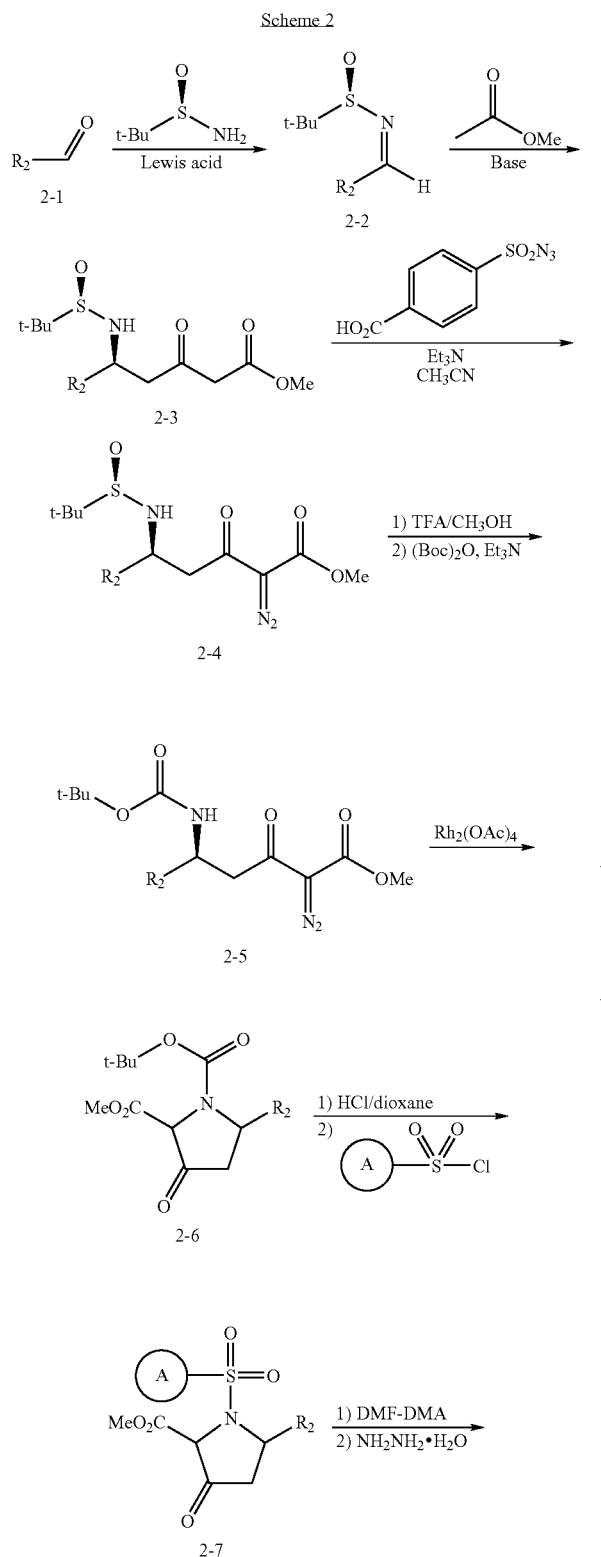

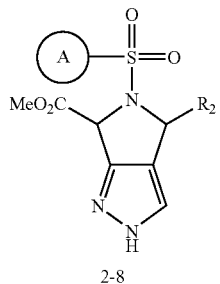

Compound of Formula 2-6 was prepared by intramolecular metal carbenoid insertion reaction of sulfinimine-derived δ-amino χ-diazoesters as described in Davis, F. A.; et al. *J. Org. Chem.*, 68, 5147-5152 (2003). Treatment of compound 2-2 with methyl acetate in the presence of a base such as sodium hexamethyldisilazane (NaHMDS) to give the N-sulfinyl δ-amino β-keto ester 2-3, which upon treatment with commercially available 4-carboxybenzenesulfonyl azide (4-CBSA) gave the N-sulfinyl δ-amino χ-diazo β-keto ester 2-4. The diazo compound, was treated with an acid such as trifluoroacetic acid (TFA) to remove the sulfinyl group, and reacted with Boc$_2$O/Et$_3$N to give the N-Boc-protected product 2-5. Intramolecular cyclization in the presence of Rh$_2$(OAc)$_4$ gave the t-Boc protected pyrrolidine 2-6. Removal of the Boc group with acid such as hydrochloric acid and sulfonation with a sulfonyl chloride of formula A-SO$_2$Cl wherein A is as defined above, in the presence of a base such as pyridine, gave the 3-oxopyrrolidine 2-7.

Compounds of Formula 2-8 can be made by treatment of the 3-oxopyrrolidine 2-7 with acylating agents such as dimethylformamide dimethyl acetal, ethyl formate, or dimethylacetamide dimethyl acetal followed by cyclization with hydrazines in a suitable solvent such as acetic acid.

One of ordinary skill in the art will appreciate that the above scheme can be used to selectively produce additional compounds of the present invention by functionalization of the ester group of compound 2-8.

Scheme 3 provides a pathway to a variety of rings disubstituted at R$_1$ and R$_2$, the non-hydrogen substituents of which, along with A, are as defined above for Formula I. One of skill in the art will appreciate that the above scheme can be used to selectively produce a single diastereomeric and/or a single enantiomeric product.

Scheme 3:

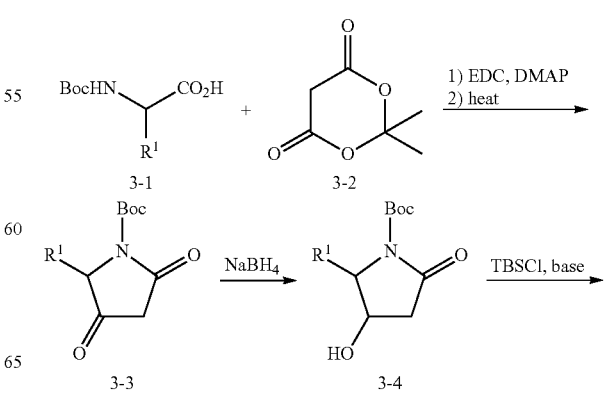

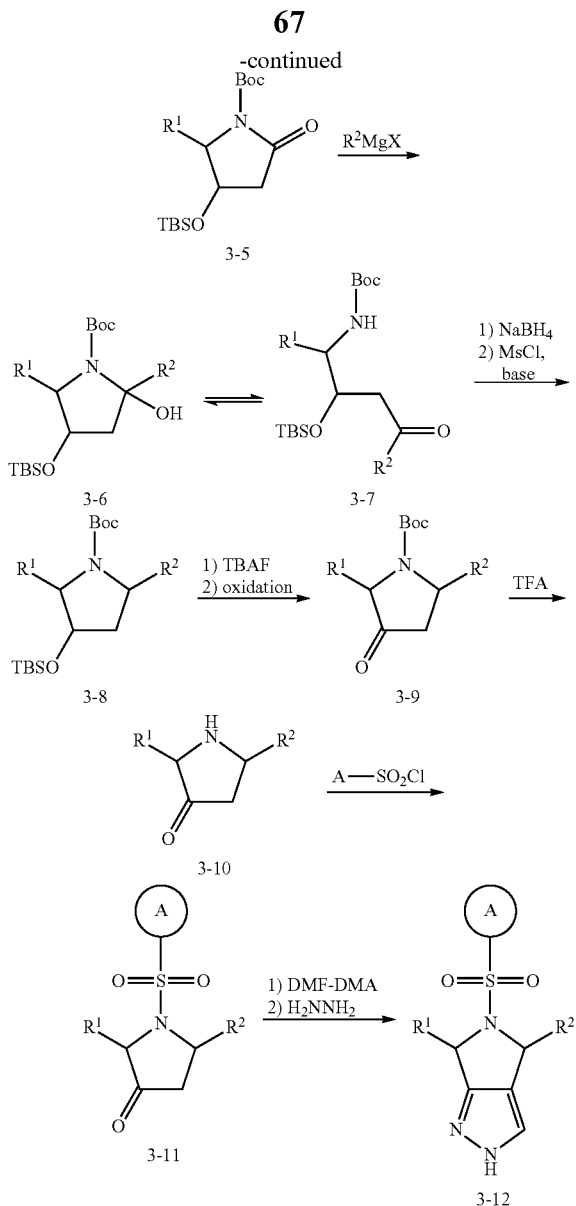

Pyrrolidinediones represented by 3-3 are prepared by reaction of protected amino alcohols (3-1) with Meldrum's acid (3-2) using a coupling reagent such as EDC (see: Hosseini, M; et al. *Org. Lett.* 2006, 8(10), 2103). Reduction of the resulting ketones with a reducing agent such as NaBH$_4$ gives alcohols 3-4 (see: Fustero, S; et al. *Org. Lett.* 2002, 4(21), 3651), which may then be protected with a suitable protecting group such as TBS to provide compounds of formula 3-5. Addition of a Grignard reagent provides tertiary alcohols 3-6 that may be in equilibrium with the keto form, 3-7 (see: Yoda, H; et al. *Tetrahedron Asymmetry* 1995 6(11), 2669). Reaction with a reducing agent such as NaBH$_4$ followed by MsCl gives pyrrolidines 3-8. Deprotection of the alcohol followed by oxidation and removal of the nitrogen protecting group using methods familiar to one of ordinary skill in the art affords compounds of the formula 3-10. Sulfonylation with a sulfonylchloride of formula A-SO$_2$Cl, wherein A is as defined for Formula I, in the presence of a base provides compounds 3-11. As described for compound 1-8 above, treatment with an acylating agent followed by cyclization with hydrazines gives compounds of the formula 3-12.

Experimental Procedures

Compounds included in this invention are exemplified by the following examples, which should not be construed as limiting the scope of this disclosure. Analogous structures and alternative synthetic routes within the scope of the invention will be apparent to those skilled in the art.

Reagents and solvents obtained from commercial suppliers were used without further purification unless otherwise stated. Thin layer chromatography was performed on pre-coated 0.25 mm silica gel plates (E. Merck, silica gel 60, F254). Visualization was achieved using UV illumination or staining with phosphomolybdic acid, ninhydrin or other common staining reagents. Flash chromatography was performed using either a Biotage Flash 40 system and prepacked silica gel columns or hand packed columns (E. Merck silica gel 60, 230-400 mesh). Preparatory HPLC was performed on a Varian Prepstar high performance liquid chromatograph. 1H NMR spectra were recorded on either a Varian Gemini 300 MHz spectrometer or a Bruker Avance 300 MHz spectrometer. Chemical shifts are reported in ppm (δ) and were calibrated using the undeuterated solvent resonance as internal standard. Mass spectra were recorded on an Agilent series 1100 mass spectrometer connected to an Agilent series 1100 HPLC.

Purity of compounds were determined by HPLC/MS analysis by a variety of analytical methods:

[1]=20% [B]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[2]=50% [B]: 50% [A] to 95% [B]: 5% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[7]=20% [B]: 80% [A] to 70% [B]: 30% [A] gradient in 10.0 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×3 cm column, 3 micron packing, 210 nm detection, at 35° C.

[10]=50% [B]: 50% [A] to 95% [B]: 5% [A] gradient in 10.0 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×3 cm column, 3 micron packing, 210 nm detection, at 35° C.

EXAMPLE 1

((R)-4-ethyl-5-(4-(trifluoromethyl)phenylsulfonyl)-1,4,5,6-tetrahydropyrrolo[3,4-c]pyrazole)

Step 1: (2S,4R)-methyl 4-hydroxypyrrolidine-2-carboxylate hydrochloride (2)

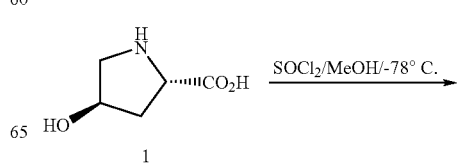

-continued

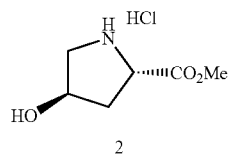

2

Thionyl chloride (11.6 ml, 160 mmol) was added to a stirred solution of (2S,4R)-4-hydroxypyrrolidine-2-carboxylic acid (10.0 g, 76.26 mmol) (1) in methanol (150 ml) at −78° C. for 10 min. The mixture was then stirred in an ice bath for 30 minutes followed by stirring at RT for 30 min. Finally the mixture was refluxed for three hours and concentrated in vacuo to give (2S,4R)-methyl 4-hydroxypyrrolidine-2-carboxylate hydrochloride (2) (17.90 g, 95%) as a white solid. Used without further purification. MS m/z 146.2 (M+H)$^+$; retention time=0.19 min, method [1].

Step 2: (2S,4R)-methyl 4-hydroxy-1-(4-(trifluoromethyl)phenylsulfonyl)pyrrolidine-2-carboxylate (3)

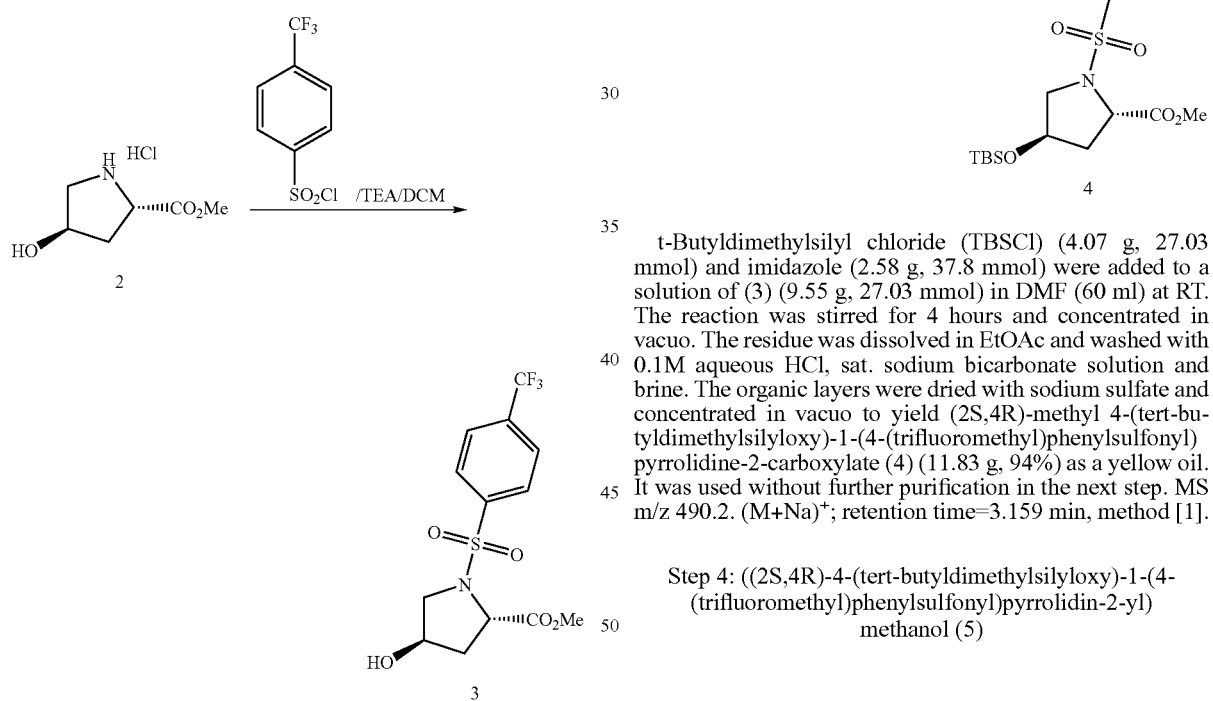

Triethylamine (TEA) (15.34 ml, 110.1 mmol) and 4-(trifluoromethyl)benzene-1-sulfonyl chloride (8.97 g, 36.7 mmol) were added to a solution of (2S,4R)-methyl 4-hydroxypyrrolidine-2-carboxylate hydrochloride (2) (6.59 g, 36.7 mmol) in dichloromethane (150 ml) in an ice bath. The mixture was warmed to room temperature and stirred overnight at RT., concentrated reaction in vacuo, dissolved in EtOAc and washed with 0.1M aqueous HCl, sat. sodium bicarbonate solution and brine. The organic layers were dried with sodium sulfate and concentrated in vacuo to yield (2S,4R)-methyl 4-hydroxy-1-(4-(trifluoromethyl)phenylsulfonyl)pyrrolidine-2-carboxylate) (3) (9.55 g, 73%) as a white semi-solid, which was used without further purification in the next step. MS m/z 376.1 (M+Na)$^+$; retention time=1.691 min, method [1].

Step 3: (2S,4R)-methyl 4-(tert-butyldimethylsilyloxy)-1-(4-(trifluoromethyl)phenylsulfonyl)pyrrolidine-2-carboxylate (4)

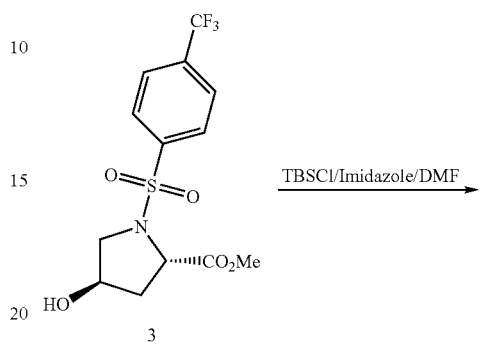

t-Butyldimethylsilyl chloride (TBSCl) (4.07 g, 27.03 mmol) and imidazole (2.58 g, 37.8 mmol) were added to a solution of (3) (9.55 g, 27.03 mmol) in DMF (60 ml) at RT. The reaction was stirred for 4 hours and concentrated in vacuo. The residue was dissolved in EtOAc and washed with 0.1M aqueous HCl, sat. sodium bicarbonate solution and brine. The organic layers were dried with sodium sulfate and concentrated in vacuo to yield (2S,4R)-methyl 4-(tert-butyldimethylsilyloxy)-1-(4-(trifluoromethyl)phenylsulfonyl)pyrrolidine-2-carboxylate (4) (11.83 g, 94%) as a yellow oil. It was used without further purification in the next step. MS m/z 490.2. (M+Na)$^+$; retention time=3.159 min, method [1].

Step 4: ((2S,4R)-4-(tert-butyldimethylsilyloxy)-1-(4-(trifluoromethyl)phenylsulfonyl)pyrrolidin-2-yl)methanol (5)

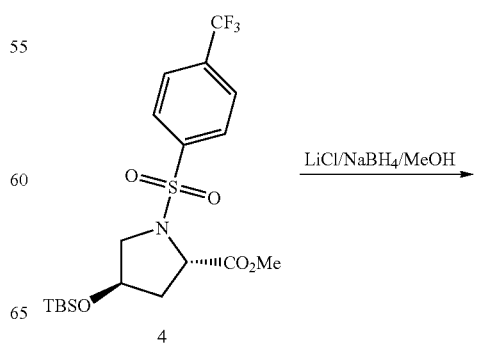

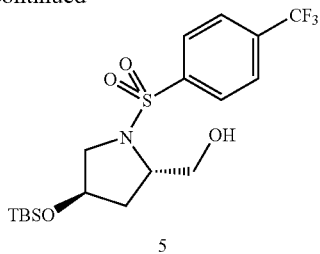

5

Lithium chloride (1.21 g, 28.49 mmol) and sodium borohydride (1.08 g, 28.49 mmol) were added to a solution of (4) in (4.44 g, 9.49 mmol) in methanol (50 ml) at RT. The reaction was stirred overnight and concentrated in vacuo. The residue was dissolved in EtOAc and washed with 0.1M aqueous HCl, sat. sodium bicarbonate solution and brine. The organic layers were dried with sodium sulfate and concentrated in vacuo. The resulting crude product was purified via column chromatography using ethyl acetate/hexane gradients to yield ((2S, 4R)-4-(tert-butyldimethylsilyloxy)-1-(4-(trifluoromethyl)phenylsulfonyl)pyrrolidin-2-yl)methanol (5) (2.23 g, 53%) as a white solid. MS m/z 440.2 (M+H)$^+$; retention time=3.006 min, method [1].

Step 5: (2S,4R)-4-(tert-butyldimethylsilyloxy)-1-(4-(trifluoromethyl)phenylsulfonyl)-2-vinylpyrrolidine (6)

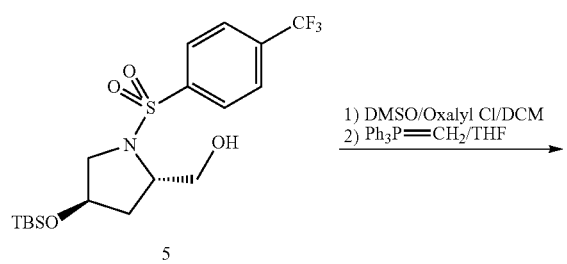

A stirred solution of oxalyl chloride (0.51 ml, 6.05 mmol) in dichloromethane (30 ml) was mixed with DMSO (0.71 ml, 10.0 mmol) at −78° C. The solution was warmed to 40° C. for 15 min and recooled to −78° C. A solution of (5) (2.20 g, 5.0 mmol) in dichloromethane (15 ml) was added dropwise over 2 hours followed by triethylamine (7.66 ml, 5.5 mmol) over 30 min. The reaction was warmed to RT and poured into sat. aqueous NH$_4$Cl, stripped of dichloromethane and dissolved in EtOAc. The organic layers were washed with brine and dried with sodium sulfate. Concentrated in vacuo to yield crude aldehyde (2.18 g, 100%) as yellow oil, which was placed immediately used without characterization or further purification.

To a stirred solution of methyltriphenylphosphonium iodide (3.94 g, 9.70 mmol) in THF (40 ml) was added n-BuLi (1.6M in hexanes, 4.85 ml, 7.76 mmol) at −78° C. The yellow mixture was stirred for 1 hour at this temp. followed by addition of a solution of the crude aldehyde (1.41 g, 3.23 mmol) in THF (10 ml). The reaction was stirred for 8 hours at −78° C. and quenched with sat. NH$_4$Cl (10 ml). The reaction was concentrated in vacuo and the residue taken up in EtOAc, washed with brine and dried with sodium sulfate.

The resulting precipitate was filtered away and the filtrate was concentrated. The residue was purified via column chromatography using ethyl acetate/hexane gradients to yield (2S, 4R)-4-(tert-butyldimethylsilyloxy)-1-(4-(trifluoromethyl)phenylsulfonyl)-2-vinylpyrrolidine (6) (0.691 g, 32%) as an off-white solid. MS m/z 436.2 (M+H); retention time=2.641 min, method [2].

Step 6: (2R,4R)-4-(tert-butyldimethylsilyloxy)-2-ethyl-1-(4-(trifluoromethyl)phenyl sulfonyl)pyrrolidine (7)

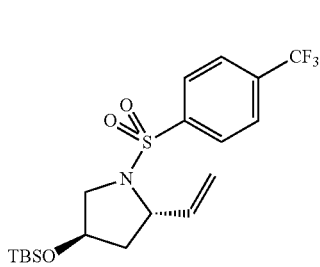

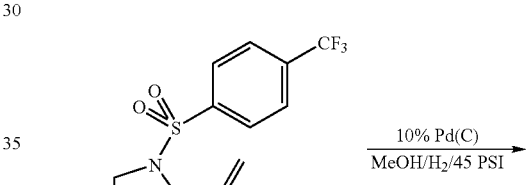

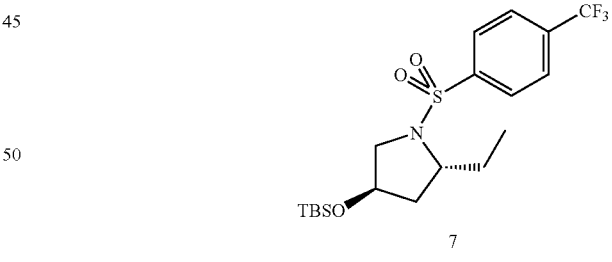

To a solution of (6) (0.663 g, 1.52 mmol) in EtOAc (5 ml) was added a small spatula tip of 10% Pd(C) and placed on Parr shaker under hydrogen at 45 PSI. The mixture was shaken under hydrogen overnight. After addition of more EtOAc the mixture was filtered through celite, and concentrated in vacuo to yield (2R,4R)-4-(tert-butyldimethylsilyloxy)-2-ethyl-1-(4-(trifluoromethyl)phenylsulfonyl)pyrrolidine (7) (0.575 g, 86%) as a white crystalline solid. MS m/z 438.1 (M+H); retention time=6.841 min, method [10].

Step 7: (R)-5-ethyl-1-(4-(trifluoromethyl)phenylsulfonyl)pyrrolidin-3-one (8)

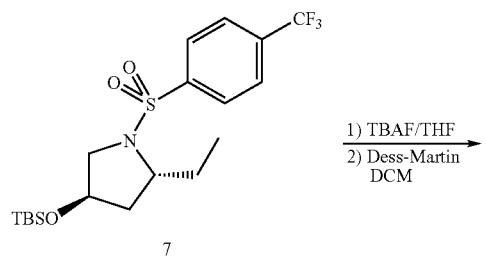

7

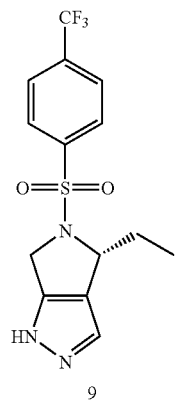

9

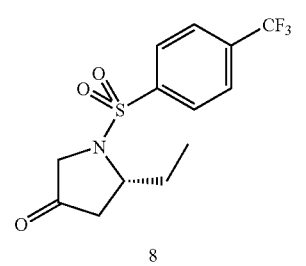

8

To a solution of (2R,4R)-4-(tert-butyldimethylsilyloxy)-2-ethyl-1-(4-(trifluoromethyl)phenylsulfonyl)pyrrolidine (7) (0.555 g, 1.27 mmol) in THF (3 ml) was added a solution of tetrabutylammonium fluoride (TBAF) (1M THF, 1.52 ml) in THF (3 ml) and the mixture was stirred for one hour. The reaction was concentrated in vacuo to give a crude alcohol (0.388 g, 95%) that was used without further purification.

The alcohol from above was dissolved in dichloromethane (5 ml) and Dess-Martin periodinane reagent (0.373 g, 0.880 mmol) was added at RT. The reaction was stirred for 90 min. An additional portion of Dess-Martin reagent (0.150 g, 0.354 mmol) was added and the reaction was further stirred overnight. After addition of dichloromethane, the reaction was washed with 1M NaOH, brine, and dried over sodium sulfate. The organic layer was concentrated in vacuo and purified via column chromatography using ethyl acetate/hexane gradients to yield (R)-5-ethyl-1-(4-(trifluoromethyl)phenylsulfonyl)pyrrolidin-3-one (8) (0.200 g, 85%) as a white solid. MS m/z 322.1 (M+H)$^+$; retention time=6.534 min, method [7].

Step 8: ((R)-4-ethyl-5-(4-(trifluoromethyl)phenylsulfonyl)-1,4,5,6-tetrahydropyrrolo[3,4-c]pyrazole) (9)

(R)-5-ethyl-1-(4-(trifluoromethyl)phenylsulfonyl)pyrrolidin-3-one (8) from above was dissolved (0.200 g, 0.622 mmol) in DMF-DMA (1.24 ml, 9.34 mmol) and heated to 90° C. for 1 hour. The reaction was concentrated in vacuo to yield (0.234 g, 0.622 mmol) of enolate that was dissolved (0.234 g, 0.622 mmol) in ethanol/acetic acid (1 ml/0.2 ml) followed by addition of hydrazine hydrate (0.151 ml, 3.11 mmol). After 2 hours, MS/HPLC analysis showed very little product formation. More hydrazine hydrate (0.151 ml, 3.11 mmol) was added and the reaction heated to 60° C. and stirred overnight. The reaction mixture was concentrated in vacuo and purified via column chromatography using DCM/MeOH gradients to yield ((R)-4-ethyl-5-(4-(trifluoromethyl)phenylsulfonyl)-1,4,5,6-tetrahydropyrrolo[3,4-c]pyrazole) (9) (50.5 mg, 25% over two steps) as a beige foam. This was a mixture of R (96%) and S (4%) isomers. $^1$H-NMR (CDCl$_3$) δ 7.99 (d, 2H, J=8.2 Hz), 7.77 (d, 2H, J=8.2 Hz), 7.26 (s, 1H), 4.82 (m, 1H), 4.54 (dd, 2H, J=13.5, 25.0 Hz), 2.09 (m, 1H), 1.86 (m, 1H), 0.90 (t, 3H, J=7.2 Hz); MS m/z 346.1 (M+H); retention time=5.529 ((R)-isomer) and 5.75 ((S)-isomer) min., method [7].

EXAMPLE 2

(R)-4-cyclopropyl-5-(4-(trifluoromethyl)phenylsulfonyl)-1,4,5,6-tetrahydropyrrolo[3,4-c]pyrazole

Step 1: (2S,4R)-4-(tert-butyldimethylsilyloxy)-2-cyclopropyl-1-(4-(trifluoromethyl)phenylsulfonyl)pyrrolidine (10)

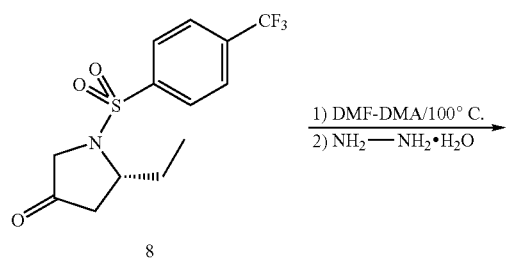

8

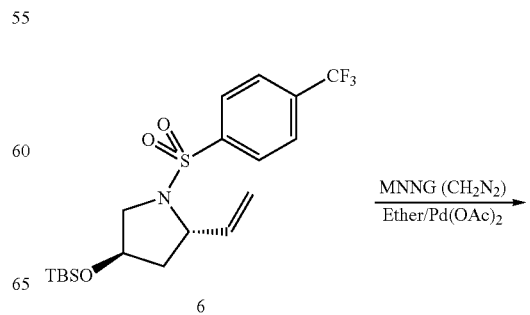

6

-continued

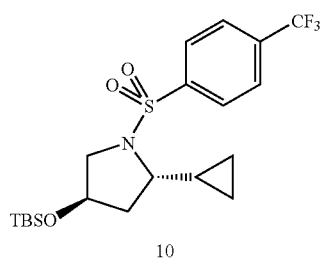
10

An ethereal solution of diazomethane was prepared by adding 1-methyl-3-nitro-1-nitrosoguanidine (MNNG) (2.84 g, 19.3 mmol) to a biphasic solution (10 ml 40% KOH/5 ml ether) and stirring at 0° C. for 5 minutes. The biphasic solution was cooled to −78° C. to freeze the aqueous layer. The diazomethane solution was decanted into a vial containing a solution of (6) (0.841 g, 1.93 mmol) in 5 ml of ether. Palladium (II) acetate (43.3 mg, 0.193 mmol) was added and the reaction was stirred for 30 min. This procedure of adding diazomethane solution followed by palladium catalyst was repeated 2 more times to produce a greater yield. Dichloromethane (10 ml) was added followed by sat. NaHCO₃ (5 ml). The catalyst was filtered off and the organic layer was isolated and dried over sodium sulfate. The organic layer was concentrated in vacuo and purified via column chromatography using ethyl acetate/hexane gradients to yield (2S,4R)-4-(tert-butyldimethylsilyloxy)-2-cyclopropyl-1-(4-(trifluoromethyl)phenylsulfonyl)pyrrolidine (10) (0.520 g, 60%) as a clear oil. This was a mixture of (R) (64%) and (S) (36%) isomers. MS m/z 449.1 (M+H)⁺; retention time=7.069 min ((R)-isomer) and 7.292 ((S) isomer); method [10].

Step 2: (S)-5-cyclopropyl-1-(4-(trifluoromethyl)phenylsulfonyl)pyrrolidin-3-one (11)

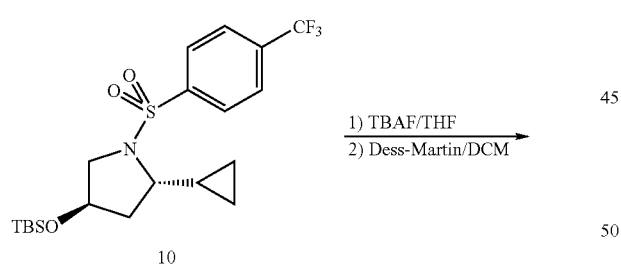

Compound (11) was prepared from compound (10) in an identical manner to that used for the preparation of compound (8). MS m/z 334.1 (M+H)⁺; retention time=7.216 min.; method [7].

Step 3: (R)-4-cyclopropyl-5-(4-(trifluoromethyl)phenylsulfonyl)-1,4,5,6-tetrahydropyrrolo[3,4-c]pyrazole (12)

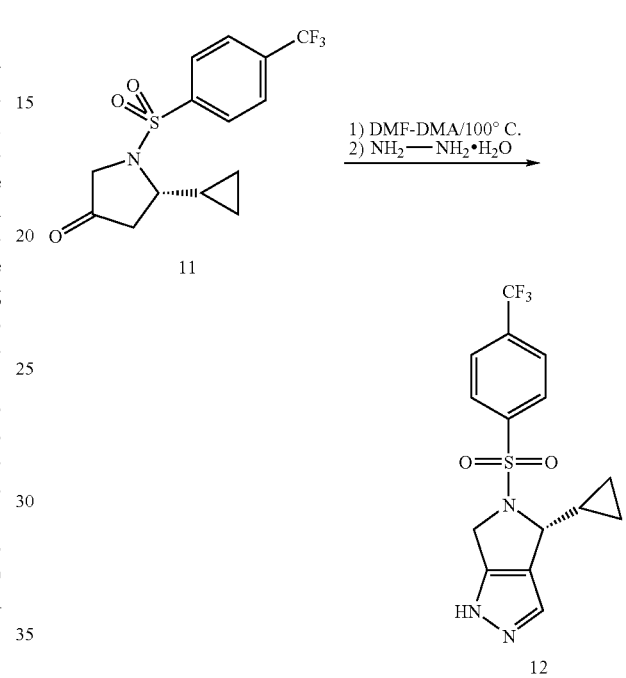

Compound (12) was prepared from compound (II) in an identical manner to that used in the preparation of compound (9).

¹H-NMR (CDCl₃) δ 8.02 (d, 2H, J=8.6 Hz), 7.76 (d, 2H, J=8.6 Hz), 7.28 (s, 1H), 4.81 (d, 1H, J=6.2 Hz), 4.58 (dd, 2H, J=13.4, 21.9 Hz), 1.38 (m, 1H), 0.67-0.40 (m, 1H), 0.09 (m, 1H); MS m/z 358.1. (M+H)⁺; retention time=5.909 min; method [7].

EXAMPLE 3

4,6-Dicyclopropyl-5-(4-(trifluoromethyl)phenylsulfonyl)-1,4,5,6-tetrahydropyrrolo[3,4-c]pyrazole Step 1: (s)-tert-Butyl 2-cyclopropyl-3,5-dioxopyrrolidine-1-carboxylate (15)

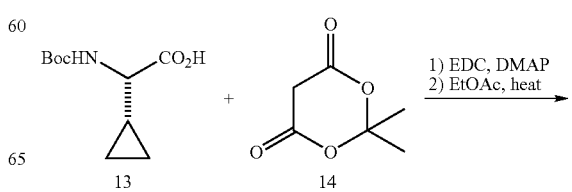

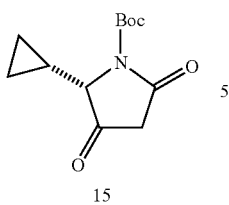

15

2-(tert-Butoxycarbonylamino)-2-cyclopropylacetic acid (13) (5.47 g, 25.4 mmol), Meldrum's acid (14) (4.02 g, 27.9 mmol), and DMAP (4.34 g, 35.56 mmol) were added to CH$_2$Cl$_2$ (100 mL) under nitrogen at 0° C. After 30 minutes EDAC (6.81 g, 35.56 mmol) was added. The reaction was stirred 16 hr at rt and poured into EtOAc (300 mL), washed with brine (200 ml), 5% citric acid (300 mL), and again brine (200 mL). The organic phase was then refluxed for 1 hr. The mixture was evaporated to give (S)-tert-butyl 2-cyclopropyl-3,5-dioxopyrrolidine-1-carboxylate (15) a yellow oil (4.0 g, 69%) that was taken into the next reaction without further purification.

Step 2: (2S,3R)-tert-Butyl 2-cyclopropyl-3-hydroxy-5-oxopyrrolidine-1-carboxylate (16)

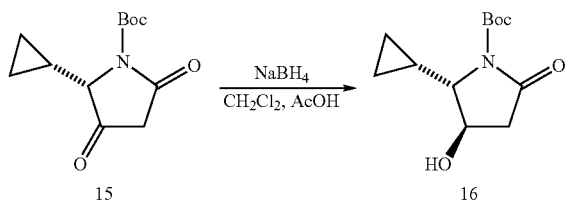

(S)-tert-Butyl 2-cyclopropyl-3,5-dioxopyrrolidine-1-carboxylate (15) (4.0 g, 17.62 mmol) was dissolved in CH$_2$Cl$_2$ (90 mL) and acetic acid (10 mL) and cooled to 0° C. NaBH$_4$ (1.33 g, 35.24 mmol) was added in several portions and the reaction stirred for 16 hr at rt. EtOAc (300 mL) was added and the organics were washed with sat. aq. NaHCO$_3$ (300 mL), brine (200 mL), and dried over Na$_2$SO$_4$. Concentration of the solution in vacuo led to isolation of (2S,3R)-tert-butyl 2-cyclopropyl-3-hydroxy-5-oxopyrrolidine-1-carboxylate (16) (1.34 g, 33%) as a white solid.

Step 3: (2S,3R)-tert-Butyl 3-(tert-butyldimethylsilyloxy)-2-cyclopropyl-5-oxopyrrolidine-1-carboxylate (17)

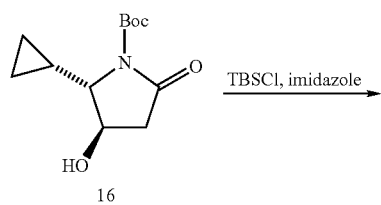

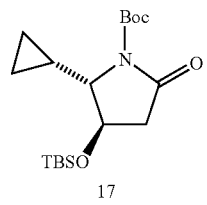

17

(2S,3R)-tert-Butyl 2-cyclopropyl-3-hydroxy-5-oxopyrrolidine-1-carboxylate (16) (1.34 g, 5.55 mmol) was placed in a flame-dried flask under nitrogen. DMF (12 mL) was added and the mixture stirred until dissolved. tert-butylchlorodimethylsilane (1.06 g, 7.02 mmol) and imidazole (0.558 g, 8.19 mmol) were added and the reaction stirred for 16 hr at rt. DMF was removed in vacuo and EtOAc (100 mL) was added and the organics were washed with sat. NaHCO$_3$ (100 mL), brine (100 mL), dried with sodium sulfate, and concentrated in vacuo. The resulting crude product was purified via column chromatography using EtOAc/hexane gradients to yield (2S,3R)-tert-butyl 3-(tert-butyldimethylsilyloxy)-2-cyclopropyl-5-oxopyrrolidine-1-carboxylate (17) (1.78 g, 90%) as a white solid.

Step 4: (4R,5S)-tert-Butyl 4-(tert-butyldimethylsilyloxy)-2,5-dicyclopropyl-2-hydroxypyrrolidine-1-carboxylate (18a) and tert-butyl (1S,2R)-2-(tert-butyldimethylsilyloxy)-1,4-dicyclopropyl-4-oxobutylcarbamate (18b)

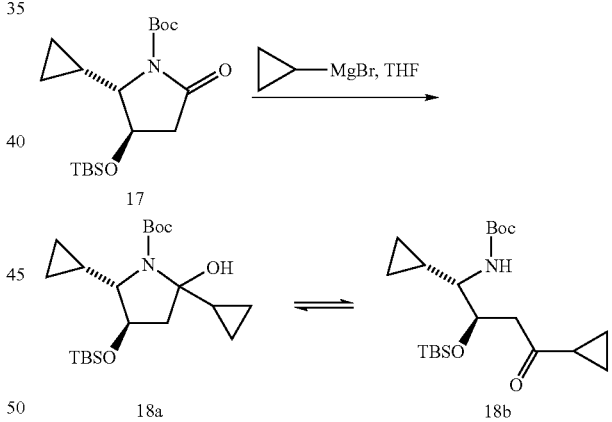

To a solution of (2S,3R)-tert-butyl 3-(tert-butyldimethylsilyloxy)-2-cyclopropyl-5-oxopyrrolidine-1-carboxylate (17) (1.44 g, 4.05 mmol) in THF (20 mL) at −78° C. under nitrogen was added cyclopropylmagnesium bromide (IM THF, 20.25 mL) dropwise. The reaction was kept at −78° C. for 3 rt followed by quenching with sat. aq. NH$_4$Cl (20 mL) and addition of CH$_2$Cl$_2$ (100 mL). The organics were washed with brine (100 mL), dried with Na$_2$SO$_4$, filtered and concentrated in vacuo. The resulting crude product was purified by column chromatography using EtOAc/hexane gradients to yield a mixture of (4R,5S)-tert-butyl 4-(tert-butyldimethylsilyloxy)-2,5-dicyclopropyl-2-hydroxypyrrolidine-1-carboxylate (18a) and tert-butyl (1S,2R)-2-(tert-butyldimethylsilyloxy)-1,4-dicyclopropyl-4-oxobutylcarbamate (18b) (322 mg, 20%) as a yellow oil.

Step 5: (2S,3R)-tert-Butyl 3-(tert-butyldimethylsilyloxy)-2,5-dicyclopropylpyrrolidine-1-carboxylate (19)

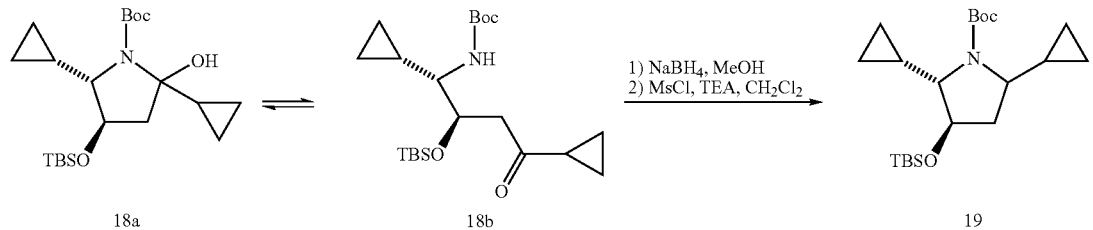

(4R,5S)-tert-Butyl 4-(tert-butyldimethylsilyloxy)-2,5-dicyclopropyl-2-hydroxypyrrolidine-1-carboxylate (18a) and tert-butyl (1S,2R)-2-(tert-butyldimethylsilyloxy)-1,4-dicyclopropyl-4-oxobutylcarbamate (18b) (774 mg, 1.95 mmol) was dissolved in MeOH (10 mL). NaBH$_4$ (111 mg, 2.90 mmol) was added portionwise and the reaction was stirred for 10 min. The reaction was quenched with sat. aq. NH$_4$Cl (10 mL) and extracted with EtOAc (2×20 mL). The combined organic layers were concentrated in vacuo to give the presumed crude alcohol 18b (692 mg) as an orange oil, which was dissolved in CH$_2$Cl$_2$ (10 mL) and placed under nitrogen. The mixture was cooled to −78° C. and Et$_3$N (0.72 mL, 5.20 mmol) was added followed by the dropwise addition of methanesulfonyl chloride (0.147 mL, 1.90 mmol). The reaction was stirred for 1 rt at −78° C. and quenched with water (5 mL). The organic layer was isolated and concentrated in vacuo. The resulting crude product was purified by column chromatography using EtOAc/hexane gradients to yield (2S,3R)-tert-butyl 3-(tert-butyldimethylsilyloxy)-2,5-dicyclopropylpyrrolidine-1-carboxylate (19) (412 mg, 55% over two steps) as a clear oil.

Step 6: (2S)-tert-Butyl 2,5-dicyclopropyl-3-oxopyrrolidine-1-carboxylate (20)

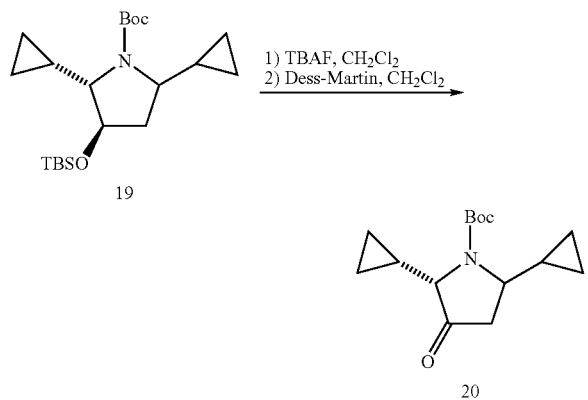

(2S,3R)-tert-Butyl 3-(tert-butyldimethylsilyloxy)-2,5-dicyclopropylpyrrolidine-1-carboxylate (19) (412 mg, 1.08 mmol) was dissolved in THF (1 mL) and placed under nitrogen. TBAF (1M THF, 1.29 mL) was added and the reaction stirred for 2 hr. The reaction was concentrated in vacuo and used without further purification. This material was dissolved in CH$_2$Cl$_2$ (2 mL) and placed under nitrogen. Dess-Martin reagent (788 mg, 1.86 mmol) was added and the reaction quenched with sat. aq. NaHCO$_3$ (2 mL) followed by sat. Na$_2$S$_2$O$_3$ (2 mL) when complete as indicated by TLC monitoring. The organic layer was isolated and concentrated in vacuo. The resulting crude product was purified by column chromatography using EtOAc/hexane gradients to yield (2S)-tert-butyl 2,5-dicyclopropyl-3-oxopyrrolidine-1-carboxylate (20) (128 mg, 45% over two steps) as a yellow oil.

Step 7: (2S)-2,5-Dicyclopropyl-1-(4-(trifluoromethyl)phenylsulfonyl)pyrrolidin-3-one (21)

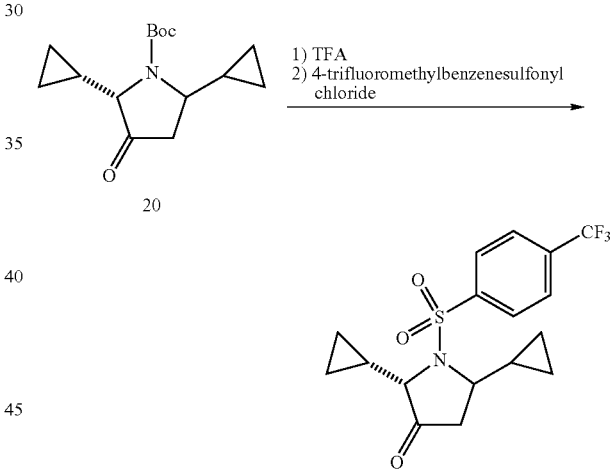

(2S)-tert-Butyl 2,5-dicyclopropyl-3-oxopyrrolidine-1-carboxylate (20) (127 mg, 0.480 mmol) was placed in dioxane (0.5 mL) and treated with 4N HCl in dioxane (2.0 mL). When reaction was done as indicated by TLC monitoring, it was concentrated in vacuo and used without further purification. This material was dissolved in CH$_2$Cl$_2$ (3 mL) and placed under nitrogen. DMAP (12 mg, 0.096 mmol) and Et$_3$N (0.20 mL, 1.44 mmol) were added and the reaction cooled to 0° C. 4-(Trifluoromethyl)benzene-1-sulfonyl chloride (129 mg, 0.528 mmol) was added and the reaction stirred for 16 hr warming from 0° C. to rt. The reaction was concentrated in vacuo and the resulting crude product was purified by column chromatography using EtOAc/hexane gradients to yield (2S)-2,5-dicyclopropyl-1-(4-(trifluoromethyl)phenylsulfonyl)pyrrolidin-3-one (21) (149 mg, 83% over two steps) as a 58:42 mixture of diastereomers. The product was a clear oil that solidified upon standing. MS (m/z) 374.1 (M+H)$^+$; retention time (210 nM)=8.329 and 8.500 min, method [7].

Step 8: (6S)-4,6-Dicyclopropyl-5-(4-(trifluoromethyl)phenylsulfonyl)-2,4,5,6-tetrahydropyrrolo[3,4-c]pyrazole (22)

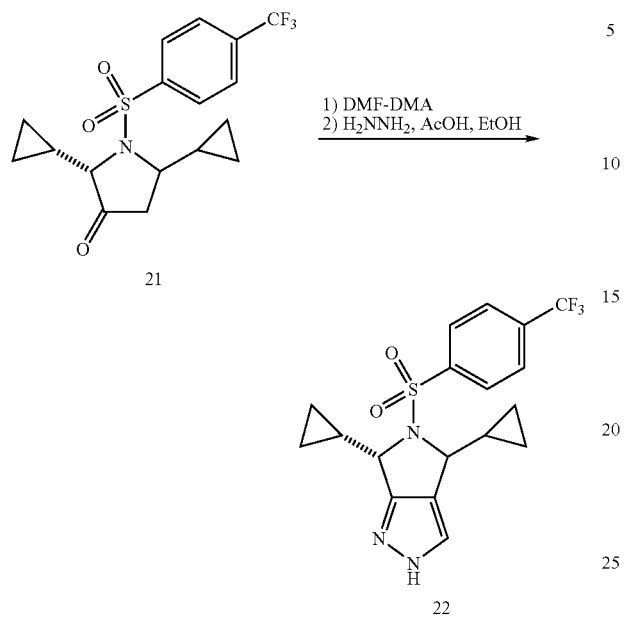

(2S)-2,5-Dicyclopropyl-1-(4-(trifluoromethyl)phenylsulfonyl)pyrrolidin-3-one (21) (149 mg, 0.399 mmol) and DMF-DMA (0.059 mL, 0.439 mmol) where heated at 60° C. for 1.5 hr under nitrogen. The reaction was concentrated in vacuo and used directly in next step. This material was dissolved in ethanol (1.5 mL) and acetic acid (0.075 mL). Hydrazine hydrate (0.1 mL, 20.0 mmol) was added dropwise and the reaction stirred for 16 hr at rt. The reaction was concentrated in vacuo and the resulting crude product was purified by column chromatography using EtOAc/hexane gradients to yield (6S)-4,6-dicyclopropyl-5-(4-(trifluoromethyl)phenylsulfonyl)-2,4,5,6-tetrahydropyrrolo[3,4-c]pyrazole (22) (30.7 mg, 19.4% over two steps) as a white solid. $^1$H-NMR (CDCl$_3$) δ 8.01 (d, 2H, J=8.2 Hz), 7.71 (d, 2H, J=8.2 Hz), 7.19 (s, 1H), 4.59 (d, 1H, J=10.3 Hz), 4.57 (d, 1H, J=10.3 Hz), 1.35 (m, 2H), 0.81 (m, 1H), 0.68-0.44 (m, 5H), (m, 1H), 0.31 (m, 1H), 0.19 (m, 1H); MS (m/z) 398.1 (M+H)$^+$; retention time=7.168, method [7].

EXAMPLE 4

(R)-4-Cyclopropyl-5-(4-(trifluoromethyl)phenylsulfonyl)-4,5-dihydropyrrolo[3,4-c]pyrazol-6(1H)-one

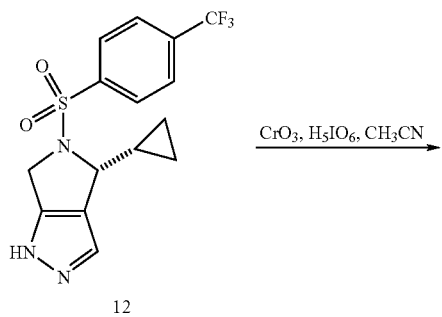

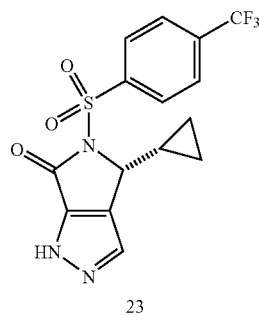

To periodic acid (176 mg, 0.770 mmol) in CH$_3$CN (2 mL) was added chromium(III) oxide (2.1 mg, 0.021 mmol). The reaction was stirred several minutes until it turned fluorescent orange and all solids were dissolved. The reaction was cooled to 0° C. and a solution of (R)-4-cyclopropyl-5-(4-(trifluoromethyl)phenylsulfonyl)-2,4,5,6-tetrahydropyrrolo[3,4-c]pyrazole (12) (50 mg, 0.14 mmol) in CH$_3$CN (1 mL) was added. The reaction was stirred for 1 hr until TLC monitoring showed the disappearance of starting material. The reaction was filtered through a plug of Celite and concentrated in vacuo. The residue was taken up in EtOAc (2 mL) and washed with water (2 mL), 5% NaHSO$_3$ (2 mL), brine (2 mL), dried over Na$_2$SO$_4$, and concentrated in vacuo. The resulting crude product was purified via column chromatography using EtOAc/hexane gradients to yield (R)-4-cyclopropyl-5-(4-(trifluoromethyl)phenylsulfonyl)-4,5-dihydropyrrolo[3,4-c]pyrazol-6(1H)-one (23) (15 mg, 28%) as a white solid.

Scheme 4

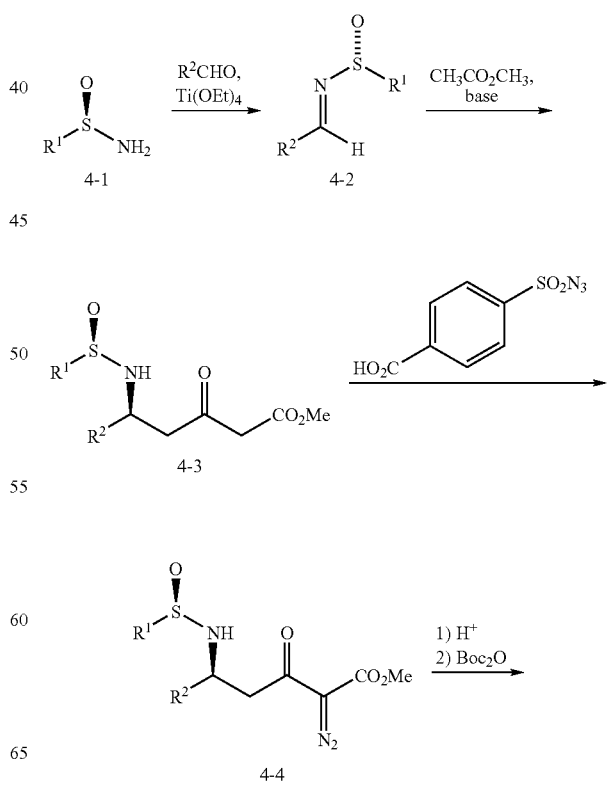

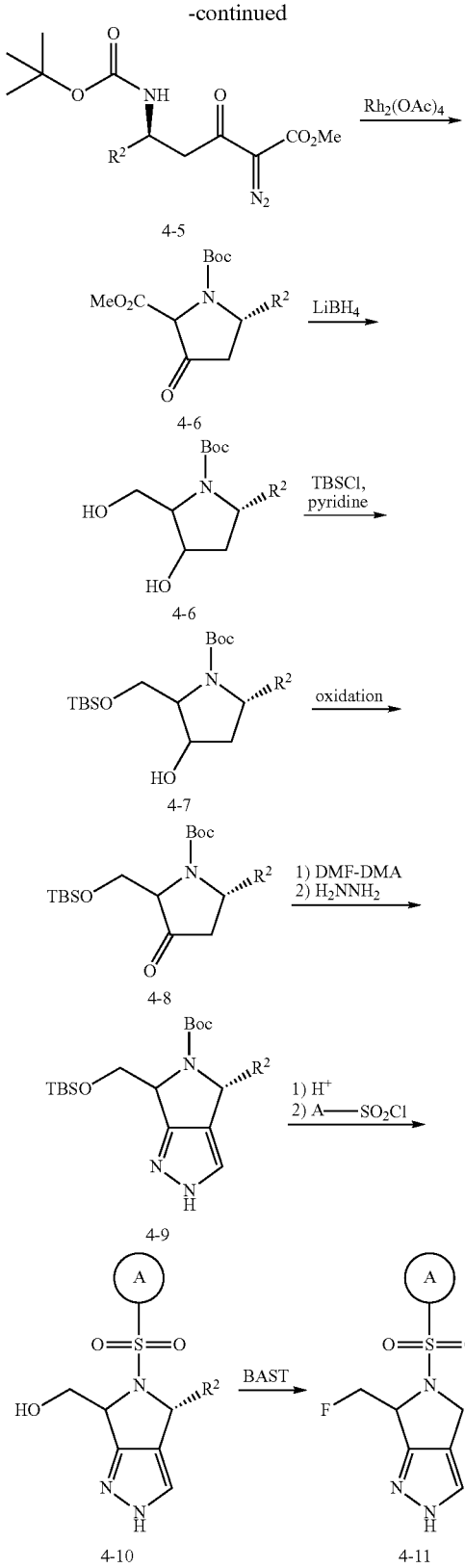

The preparation of chiral sulfinamides is described in: Cogan, D. A; et al. *J. Am. Chem. Soc.* 1998, 120(32), 8011 and Davis, F. A.; et al. *J. Org. Chem.* 1999, 64(4), 1403. Condensation of sulfinamides of formula 4-1 with an aldehyde using a Lewis acid such as Ti(OEt)$_4$ provides sulfinimine compounds 4-2. Reaction of a sulfinimine 4-2 with an excess of methyl acetate and a base gives compounds as shown in 4-3 (see: Davis, F. A.; et al. *Org. Lett.* 2000, 2(8), 1041). Treatment of ester 4-3 with (4-carboxybenzene)sulfonyl azide provides compounds 4-4 (see: Davis, F. A.; et al. *Org. Lett.* 2002, 4(9), 1599). The carbamate-protected amine may be obtained by treatment of compound 4-4 with an acid to afford the primary amine followed by reaction with a reagent capable of forming a carbamate from a primary amine such as di-tert-butyl dicarbonate. Cyclization to the pyrrolidinone (4-6) can be accomplished by formation of a metal carbenoid with a reagent such as Rh$_2$(OAc)$_4$. Simultaneous reduction of the ketone and ester can be accomplished with a reducing agent such as LiBH$_4$ to afford alcohol 4-6. Methods familiar to one of ordinary skill in the art may be used to selectively protect the primary alcohol and subsequently oxidize the secondary alcohol to the ketone to afford a protected alcohol such as compound 4-8. As described for compound 1-8 above, treatment with an acylating agent followed by cyclization with hydrazines may give compounds of formula 4-9. Removal of the carbamate protecting group followed by sulfonylation with a sulfonylchloride of formula A-SO$_2$Cl, wherein A is as defined above, in the presence of a base such as pyridine may give compound 4-10. Conversion of the alcohol to the fluoride may be accomplished with a number of reagents familiar to one of ordinary skill in the art such as BAST to afford compound 4-11.

EXAMPLE 5

(4R)-4-Cyclopropyl-6-(fluoromethyl)-5-(4-(trifluoromethyl)phenylsulfonyl)-2,4,5,6-tetrahydropyrrolo[3,4-c]pyrazole Step 1: (R)-2-Methylpropane-2-sulfinamide

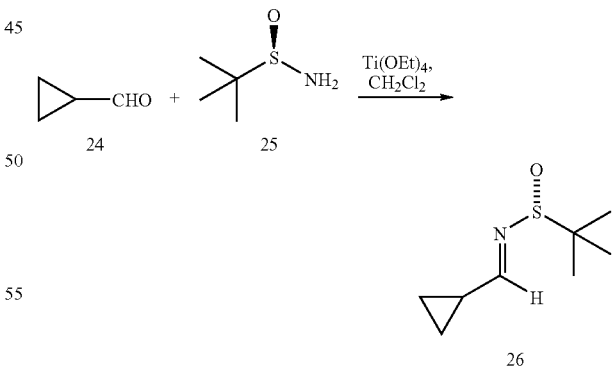

In the above scheme 4, A is as defined for Formula I above. One of ordinary skill in the art will appreciate that the above scheme can be used to selectively produce a single diastereomer and/or a single enantiomer.

(R)-2-Methylpropane-2-sulfinamide (25) (8.63 g, 71.3 mmol) and Ti(OEt)$_4$ (30 mL, 142.6 mmol) were added to a solution of cyclopropylcarboxaldehyde (24) (5 g, 71.3 mmol) in THF (142 mL). The reaction mixture was stirred at rt for 17 h after which brine (142 mL) was added and the resulting suspension was filtered through a pad of Celite. The filtrate was extracted with EtOAc (200 mL) and the organic phase was dried (Na$_2$SO$_4$), filtered and concentrated under vacuum to give 12.7 g (quant) of (R,E)-N-(cyclopropylmethylene)-2-methylpropane-2-sulfinamide (26). Retention time (min) =1.459 method [1], MS (m/z) 174.1 (M+H)+.

Step 2: (5S)-Methyl 5-cyclopropyl-5-[(R)-1,1-dimethylethylsulfinamido]-3-oxopentanoate

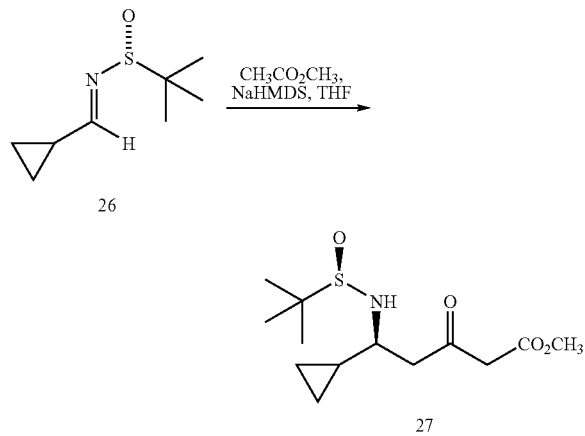

NaHMDS (428 mL, 1 M in hexane) was dissolved in THF (356 mL) and the resulting solution was cooled to −78° C. Methyl acetate (28.3 mL, 356 mmol) was added over 15 minutes and the reaction mixture was stirred at −78° C. for 1 h after which a solution (R,E)-N-(cyclopropylmethylene)-2-methylpropane-2-sulfinamide (26) (12.3 g, 71.3 mmol) in THF (50 mL) was added over 15 minutes. The reaction mixture was warmed to −20° C. and stirred at this temperature for 3 h after which HPLC indicated that the reaction was complete. The resulting solution was diluted with EtOAc (400 mL) and washed with sat. aq. NaHCO₃ (200 mL). The organic phase was dried (Na₂SO₄), filtered, concentrated under vacuum and purified on a silica gel column (eluant hexane/EtOAc, 9/1 to 1/1 to give 16.3 g (79%) of (5S)-methyl 5-cyclopropyl-5-[(R)-1,1-dimethylethylsulfinamido]-3-oxopentanoate (27). Retention time (min)=1.397 method [1], MS (m/z) 290.2 (M+H)+.

Step 3: (5S)-Methyl 5-cyclopropyl-2-diazo-5-[(R)-1,1-dimethylethylsulfinamido]-3-oxopentanoate

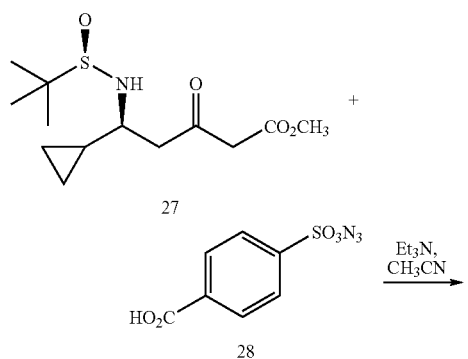

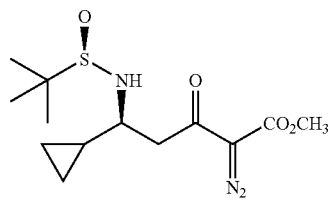

4-Carboxybenzenesulfonyl azide (28) (8.79 g, 38.7 mmol) was added to a solution of (5S)-methyl 5-cyclopropyl-5-[(R)-1,1-dimethylethylsulfinamido]-3-oxopentanoate (27) (10.2 g, 35.2 mmol) in CH₃CN (230 mL) and the resulting solution was stirred at rt for 5 h. The resulting solution was diluted with EtOAc (200 mL) and washed with sat. brine (100 mL). The organic phase was dried (Na₂SO₄), filtered and concentrated under vacuum to give (5S)-methyl 5-cyclopropyl-2-diazo-5-[(R)-1,1-dimethylethylsulfinamido]-3-oxopentanoate (29). Retention time (min)=1.634 method [1], MS (m/z) 316.2 (M+H)+.

Step 4: (S)-Methyl 5-(tert-butoxycarbonylamino)-5-cyclopropyl-2-diazo-3-oxopentanoate

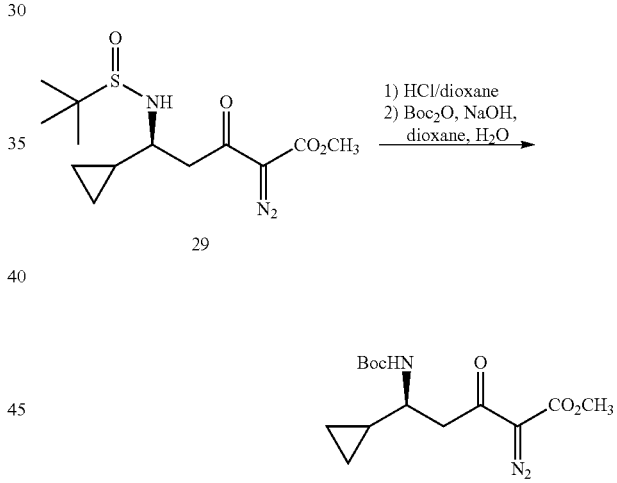

HCl in dioxane (4 N, 17 mL) was added to a solution of (5S)-methyl 5-cyclopropyl-2-diazo-5-[(R)-1,1-dimethylethylsulfinamido]-3-oxopentanoate (29) (10.9 g, 34.8 mmol) in MeOH (170 mL) and the resulting solution was stirred at rt for 0.5 h. The reaction mixture was concentrated under vacuum and the residue was dissolved in dioxane (50 mL). Water (50 mL), NaOH (2.78 g, 69.6 mmol) and Boc₂O (11.3 g, 52.2 mmol) were added and the resulting mixture was stirred at rt for 4 h. The reaction mixture was diluted with EtOAc (150 mL) and washed with brine (50 mL). The organic phase was dried (Na₂SO₄), filtered, concentrated under vacuum and purified on a silica gel column (eluant hexane/EtOAc, 9/1 to 1/1 to give 10.4 g (96%) of (s)-methyl 5-(tert-butoxycarbonylamino)-5-cyclopropyl-2-diazo-3-oxopentanoate (30). Retention time (min)=2.029 method [1], MS (m/z) 336.1 (M+Na)+.

Step 5: (5S)-1-tert-Butyl 2-methyl 5-cyclopropyl-3-oxopyrrolidine-1,2-dicarboxylate

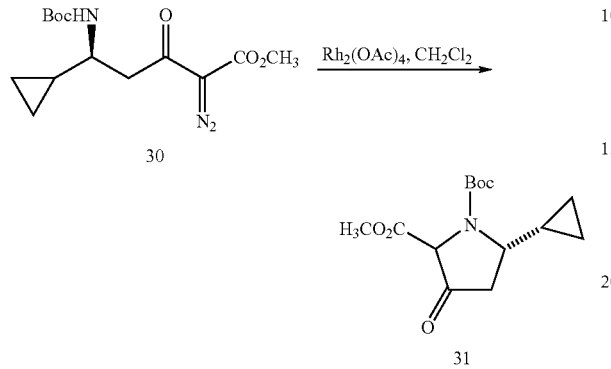

(S)-Methyl 5-(tert-butoxycarbonylamino)-5-cyclopropyl-2-diazo-3-oxopentanoate (30) (2.75 g, 8.84 mmol) was dissolved in CH$_2$Cl$_2$ (45 mL). The solution was evacuated and purged with N$_2$ three times after which Rh$_2$(OAc)$_4$ (195 mg, 0.44 mmol) was added. The resulting green solution was stirred at rt for 1 h and was subsequently concentrated under vacuum. The residue was purified on a silica gel column (eluant hexane/EtOAc, 9/1 to 1/1 to give 1.75 g (70%) of (5S)-1-tert-butyl 2-methyl 5-cyclopropyl-3-oxopyrrolidine-1,2-dicarboxylate (31). Retention time (min)=1.981 method [1], MS (m/z) 306.2 (M+Na)+.

Step 6: (5S)-tert-Butyl 5-cyclopropyl-3-hydroxy-2-(hydroxymethyl)pyrrolidine-1-carboxylate

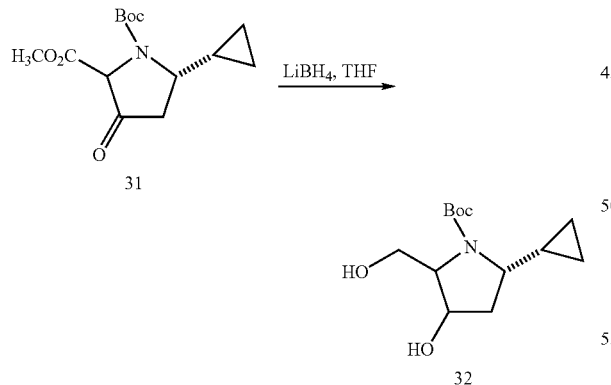

LiBH$_4$ (0.5 g, 23.3 mmol) was added to a solution of (5S)-1-tert-butyl 2-methyl 5-cyclopropyl-3-oxopyrrolidine-1,2-dicarboxylate (31) (2.2 g, 7.76 mmol) in THF (20 mL). The reaction mixture was stirred at 60° C. for 18 h after which HPLC indicated that the reaction was compete. The resulting solution was diluted with EtOAc (20 mL) and washed with sat. aq. NaHCO$_3$ (20 mL). The organic phase was dried (Na$_2$SO$_4$), filtered and concentrated under vacuum to give (5S)-tert-butyl 5-cyclopropyl-3-hydroxy-2-(hydroxymethyl) pyrrolidine-1-carboxylate (32). Retention time (min)=1.484 method [1], MS (m/z) 280.2 (M+Na)+.

Step 7: (5S)-tert-Butyl 2-((tert-butyldimethylsilyloxy)methyl)-5-cyclopropyl-3-hydroxypyrrolidine-1-carboxylate

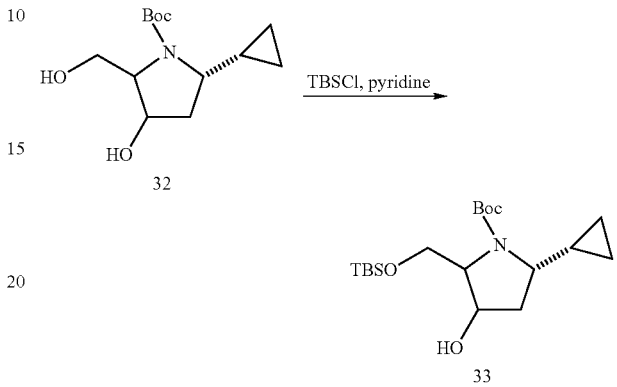

TBSCl (1.35 g, 9.00 mmol) was added to a solution of (5S)-tert-butyl 5-cyclopropyl-3-hydroxy-2-(hydroxymethyl) pyrrolidine-1-carboxylate (32) (1.93 g, 7.50 mmol) in pyridine (15 mL) and the resulting solution was stirred at rt for 18 h. The reaction mixture was diluted with CH$_2$Cl$_2$ (20 mL) and washed with 1 N aq. HCl (10 mL). The organic phase was dried (Na$_2$SO$_4$), filtered and concentrated under vacuum to give (5S)-tert-butyl 2-((tert-butyldimethylsilyloxy)methyl)-5-cyclopropyl-3-hydroxypyrrolidine-1-carboxylate (33). Retention time (min)=3.261 method [1], MS (m/z) 394.2 (M+Na)+.

Step 8: (5S)-tert-Butyl 2-((tert-butyldimethylsilyloxy)methyl)-5-cyclopropyl-3-oxopyrrolidine-1-carboxylate

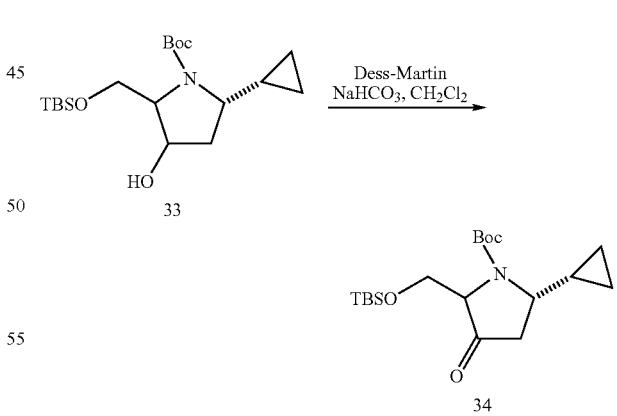

(5S)-tert-Butyl 2-((tert-butyldimethylsilyloxy)methyl)-5-cyclopropyl-3-hydroxypyrrolidine-1-carboxylate (33) (2.72 g, 7.32 mmol) was dissolved in CH$_2$Cl$_2$ (35 mL). NaHCO$_3$ (2.76 g, 32.9 mmol) and Dess-Martin periodinane (4.65 g, 10.98 mmol) were added and the resulting suspension was stirred at rt for 2 h. A mixture of sat. aq. NaHCO$_3$ and sat. aq. sodium sulfite (20 mL, 1/1) was added and the resulting solution was stirred for 15 minutes. The biphasic mixture was extracted with CH$_2$Cl$_2$ (30 mL) and the organic phase was dried (Na$_2$SO$_4$), filtered, concentrated under vacuum and purified on a silica gel column (eluant hexane/EtOAc, 9/1 to 1/1 to give 1.54 g (56%, 3 steps) of (5S)-tert-butyl 2-((tert-butyldimethylsilyloxy)methyl)-5-cyclopropyl-3-oxopyrrolidine-1-carboxylate (34). Retention time (min)=2.628, method [2], MS (m/z) 392.2 (M+Na)$^+$.

Step 9: (4R)-tert-Butyl 6-((tert-butyldimethylsilyloxy)methyl)-4-cyclopropyl-4,6-dihydropyrrolo[3,4-c]pyrazole-5(2H)-carboxylate

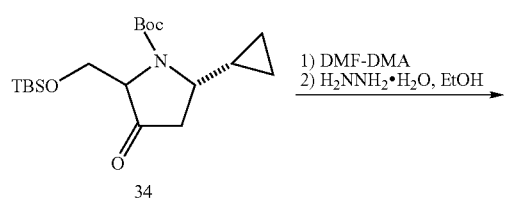

(5S)-tert-Butyl 2-((tert-butyldimethylsilyloxy)methyl)-5-cyclopropyl-3-oxopyrrolidine-1-carboxylate (34) (1.52 g, 4.11 mmol) was dissolved in DMF-DMA (5 mL) and heated to 110° C. for 1 h. The reaction mixture was concentrated under vacuum and to the resulting residue was added EtOH (8 mL) and hydrazine monohydrate (0.99 mL, 20.5 mmol). The resulting solution was stirred at rt for 5 h after which EtOAc (10 mL) was added. The solution was washed with brine (10 mL), dried (Na$_2$SO$_4$), filtered, concentrated under vacuum and purified on a silica gel column (eluant hexane/EtOAc, 9/1 to 1/1) to give 1.41 g (87%) of (4R)-tert-butyl 6-((tert-butyldimethylsilyloxy)methyl)-4-cyclopropyl-4,6-dihydropyrrolo[3,4-c]pyrazole-5(2H)-carboxylate (35). Retention time (min)=2.086, method [1], MS (m/z) 394.2 (M+H)$^+$.

Step 10: ((4R)-4-Cyclopropyl-2,4,5,6-tetrahydropyrrolo[3,4-c]pyrazol-6-yl)methanol

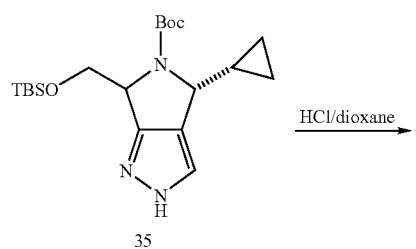

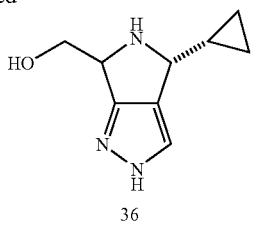

(4R)-tert-butyl 6-((tert-butyldimethylsilyloxy)methyl)-4-cyclopropyl-4,6-dihydropyrrolo[3,4-c]pyrazole-5(2H)-carboxylate (35) (1.38 g, 3.51 mmol) was covered with HCl in dioxane (4 N, 5 mL).). The reaction mixture was stirred at rt for 1 hr after which it was concentrated under vacuum to give ((4R)-4-cyclopropyl-2,4,5,6-tetrahydropyrrolo[3,4-c]pyrazol-6-yl)methanol (36). Retention time (min)=0.203, method [1], MS (m/z) 180.2 (M+H)$^+$.

Step 11: ((4R)-4-Cyclopropyl-5-(4-(trifluoromethyl)phenylsulfonyl)-2,4,5,6-tetrahydropyrrolo[3,4-c]pyrazol-6-yl)methanol

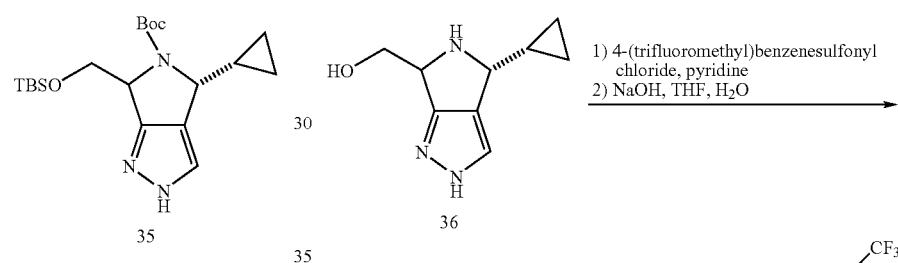

((4R)-4-cyclopropyl-2,4,5,6-tetrahydropyrrolo[3,4-c]pyrazol-6-yl)methanol (36) (627 mg, 3.50 mmol) and 4-trifluoromethylbenzenesulfonyl chloride (2.57 g, 10.5 mmol) were dissolved in pyridine (5 mL) and the resulting mixture was stirred at rt for 12 h. The reaction mixture was diluted with CH$_2$Cl$_2$ (10 mL) and washed with 1 N aq. HCl (10 mL). The aq. phase was separated and extracted once with CH$_2$Cl$_2$ (10 mL) and the combined organic phases were then dried (Na$_2$SO$_4$), filtered and concentrated under vacuum. The residue was dissolved in THF (5 mL) and 3 N aq. NaOH (3.5 mL) was added. The resulting mixture was stirred at rt for 18 h and was subsequently extracted with EtOAc. The organic phase was then dried (Na$_2$SO$_4$), filtered, concentrated under vacuum and purified by preparative HPLC to give ((4R)-4-cyclopropyl-5-(4-(trifluoromethyl)phenylsulfonyl)-2,4,5,6-tetrahydropyrrolo[3,4-c]pyrazol-6-yl)methanol (37) as a white solid. Retention time (min)=5.573, method [7], MS (m/z) 410.0 (M+Na)$^+$.

Step 12: (4R)-4-Cyclopropyl-6-(fluoromethyl)-5-(4-(trifluoromethyl)phenylsulfonyl)-2,4,5,6-tetrahydropyrrolo[3,4-c]pyrazole

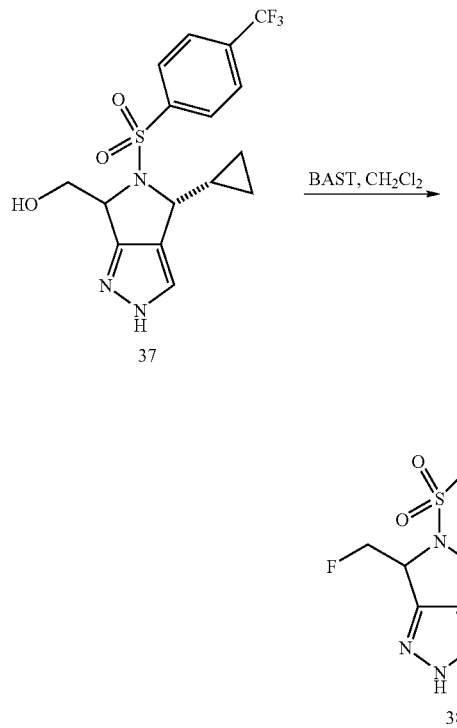

BAST (103 μL, 0.56 mmol) was added to a solution of ((4R)-4-cyclopropyl-5-(4-(trifluoromethyl)phenylsulfonyl)-2,4,5,6-tetrahydropyrrolo[3,4-c]pyrazol-6-yl)methanol (37) (109 mg, 0.28 mmol) in $CH_2Cl_2$ (1.4 mL) and the resulting solution was stirred at rt for 0.5 h. The reaction mixture was diluted with $CH_2Cl_2$ (5 mL) and washed with sat. aq. $NaHCO_3$ (5 mL). The organic phase was then dried ($Na_2SO_4$), filtered, concentrated under vacuum and the residue was purified on a silica gel column (eluant hexane/EtOAc, 9/1 to 1/1) and preparative HPLC to give (4R)-4-cyclopropyl-6-(fluoromethyl)-5-(4-(trifluoromethyl)phenylsulfonyl)-2,4,5,6-tetrahydropyrrolo[3,4-c]pyrazole (38) as a white solid. Retention time (min)=7.253, method [7], MS(m/z) 390.1 (M+H)$^+$.

Scheme 5:

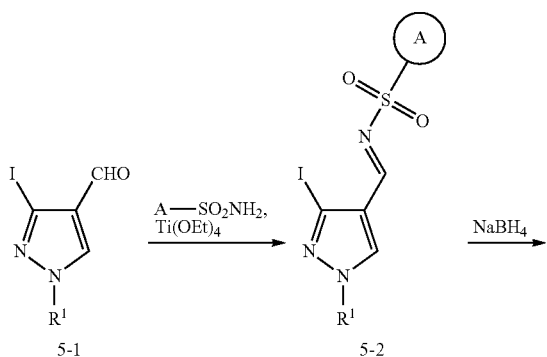

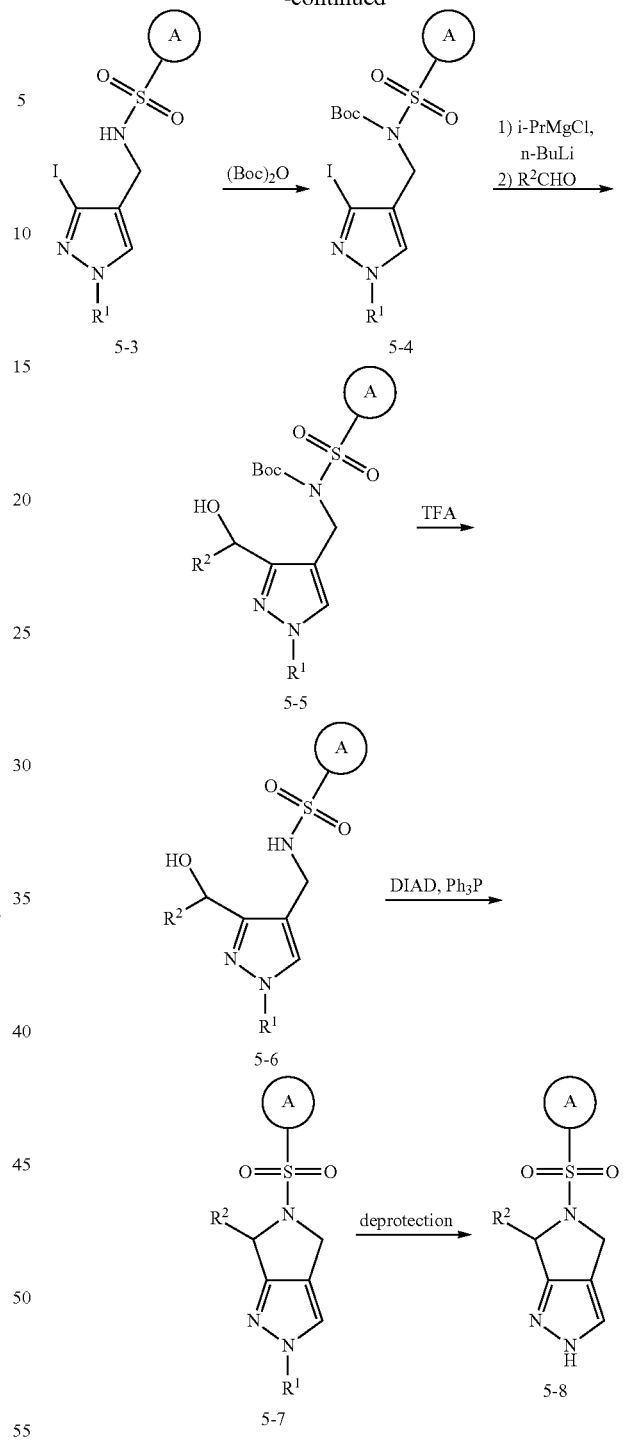

In the above scheme, A is as defined in Formula I above. One of ordinary skill in the art will appreciate that the above scheme can be used to selectively produce a single diastereomer and/or a single enantiomer.

The preparation of protected pyrazole aldehydes 5-1 was described in WO2007143523. Condensation of a selected sulfonamide with aldehyde 5-1 using a Lewis acid such as Ti(OEt)$_4$ provides imides represented by compound 5-2. Reduction of imides with a suitable reducing agent such as NaBH$_4$ gives sulfonamides 5-3. Protection of obtained sulfonamides with a protecting group such as Boc using (Boc)$_2$O affords compounds of formula 5-4. Halogen-metal exchange with reagents such as i-PrMgCl/n-BuLi followed by addition of an aldehyde affords alcohols of formula 5.5 (see: Knochel, P.; et al. *Angew. Chem., Int. Ed.* 2003, 42(36), 4302). Removal of the carbamate protecting group with TFA followed by ring formation using a reaction such as the Mitsunobu reaction provides pyrrolidines 5-7. Deprotection of the pyrazole using methods familiar to one of ordinary skill in the art gives compounds represented by 5-8.

EXAMPLE 6

6-(4-Fluorophenyl)-5-(4-(trifluoromethyl)phenylsulfonyl)-2,4,5,6-tetrahydropyrrolo[3,4-c]pyrazole

Step 1: N-((3-Iodo-1-(methoxymethyl)-1H-pyrazol-4-yl)methylene)-4-(trifluoromethyl)benzenesulfonamide

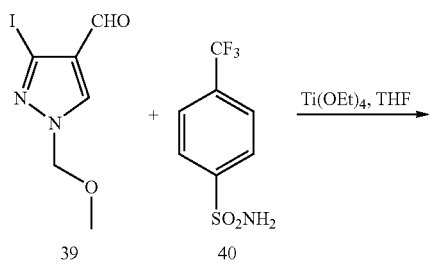

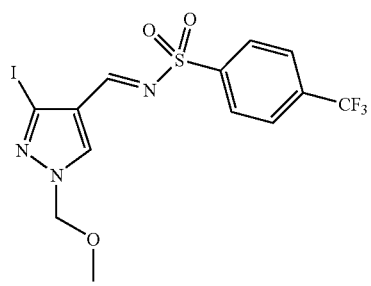

3-Iodo-1-(methoxymethyl)-1H-pyrazole-4-carbaldehyde (39) (2.0 g, 7.52 mmol) and 4-(trifluoromethyl)benzenesulfonamide (40) (1.69 g, 7.52 mmol) were dissolved in THF (20 mL) under nitrogen. Titanium(IV) ethoxide (7.8 mL, 37.6 mmol) was added via syringe and the reaction stirred for 16 hr at rt. The reaction was poured into brine (50 mL) and filtered through a pad of Celite. The filtrate was extracted with EtOAc (3×50 mL) and the combined organics were washed with brine (100 mL), dried over $Na_2SO_4$, and concentrated in vacuo to give N-((3-iodo-1-(methoxymethyl)-1H-pyrazol-4-yl)methylene)-4-(trifluoromethyl)benzenesulfonamide (41) as a clear oil that was used without further purification.

Step 2: N-((3-Iodo-1-(methoxymethyl)-1H-pyrazol-4-yl)methyl)-4-(trifluoromethyl)benzenesulfonamide

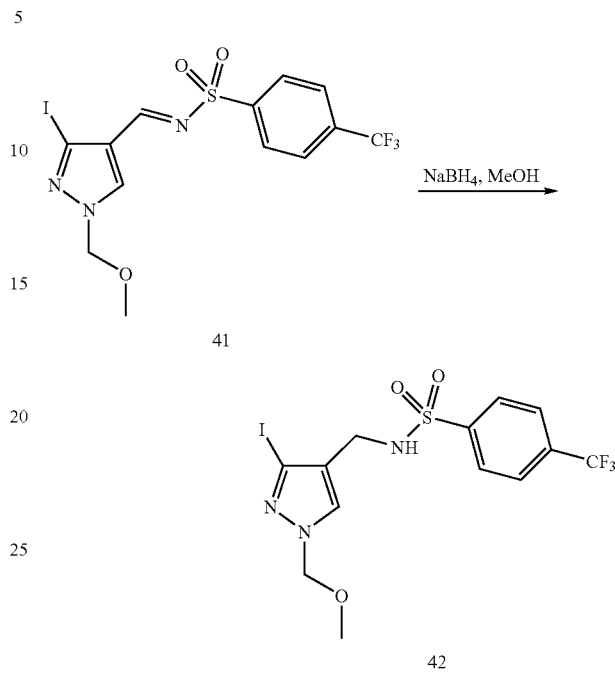

N-((3-Iodo-1-(methoxymethyl)-1H-pyrazol-4-yl)methylene)-4-(trifluoromethyl)benzenesulfonamide (41) (7.41 g, 15.66 mmol) was suspended in MeOH (20 mL). $NaBH_4$ was added portionwise and the reaction was stirred for 3 hr until TLC monitoring revealed the disappearance of starting material. Water (20 mL) was added and MeOH was removed in vacuo. The residue was taken up in EtOAc (100 mL) and washed with sat. aq. $NaHCO_3$ (100 mL) and dried over $Na_2SO_4$. The reaction was concentrated in vacuo. The resulting crude product was purified by column chromatography using EtOAc/hexane gradients to yield N-((3-iodo-1-(methoxymethyl)-1H-pyrazol-4-yl)methyl)-4-(trifluoromethyl)benzenesulfonamide (42) (1.44 g, 37% over two steps) as a clear oil that solidified upon standing.

Step 3: tert-Butyl (3-iodo-1-(methoxymethyl)-1H-pyrazol-4-yl)methyl(4-(trifluoromethyl)phenylsulfonyl)carbamate

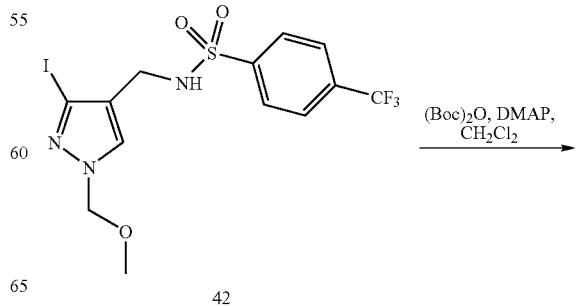

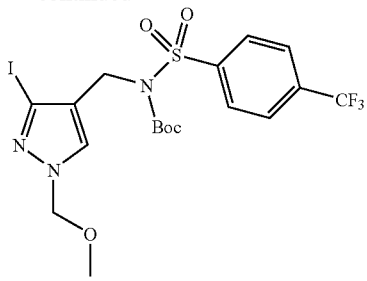

43

Di-tert-butyl dicarbonate (825 mg, 3.78 mmol) was added to a stirred solution of N-((3-iodo-1-(methoxymethyl)-1H-pyrazol-4-yl)methyl)-4-(trifluoromethyl)benzene-sulfonamide (898 mg, 1.89 mmol) (42) and DMAP (46 mg, 0.378 mmol) in $CH_2Cl_2$ (15 mL) at rt for 16 hr. The reaction was concentrated in vacuo. The resulting crude product was purified by column chromatography using EtOAc/hexane gradients to yield tert-butyl (3-iodo-1-(methoxymethyl)-1H-pyrazol-4-yl)methyl(4-(trifluoromethyl)phenylsulfonyl)carbamate (43) (985 mg, 91%) as a clear oil.

Step 4: tert-Butyl (3-((4-fluorophenyl)(hydroxy)methyl)-1-(methoxymethyl)-1H-pyrazol-4-yl)methyl(4-(trifluoromethyl)phenylsulfonyl)carbamate

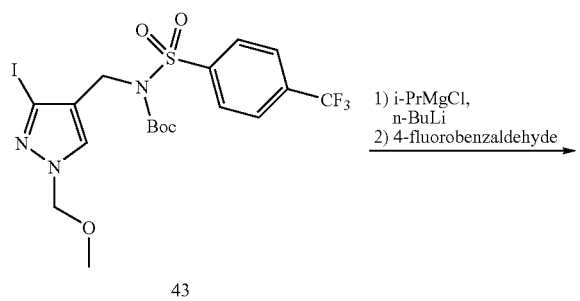

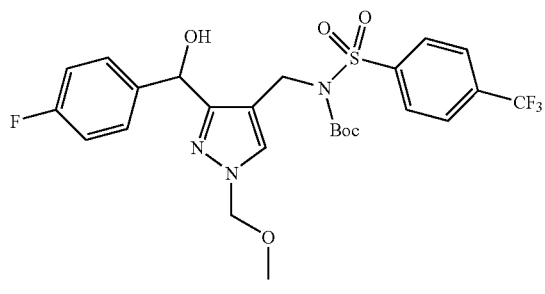

To a flame-dried flask under nitrogen was added THF (3 mL) followed by isopropylmagnesium chloride (2M THF, 0.708 mL) and the mixture cooled to −10° C. n-BuLi (1.6M Hexane, 1.77 mL) was added dropwise and stirred for 30 minutes. The reaction was cooled to −78° C. and tert-butyl (3-iodo-1-(methoxymethyl)-1H-pyrazol-4-yl)methyl(4-(trifluoromethyl)phenylsulfonyl)carbamate (43) (815 mg, 1.42 mmol) in THF (3 mL) was added dropwise and stirred for 30 minutes. 4-Fluorobenzaldehyde (0.91 mL, 8.52 mmol) was added neat and stirred for 1 hr before quenching with aq. ammonium chloride (5 mL). The aqueous layer was discarded and the reaction was concentrated in vacuo. The resulting crude product was purified by column chromatography using EtOAc/hexane gradients to yield tert-butyl (3-((4-fluorophenyl)(hydroxy)methyl)-1-(methoxymethyl)-1H-pyrazol-4-yl)methyl(4-(trifluoromethyl)phenylsulfonyl)carbamate (44) (447 mg, 55%) as a clear oil.

Step 5: N-((3-((4-Fluorophenyl)(hydroxy)methyl)-1-(methoxymethyl)-1H-pyrazol-4-yl)methyl)-4-(trifluoromethyl)benzenesulfonamide

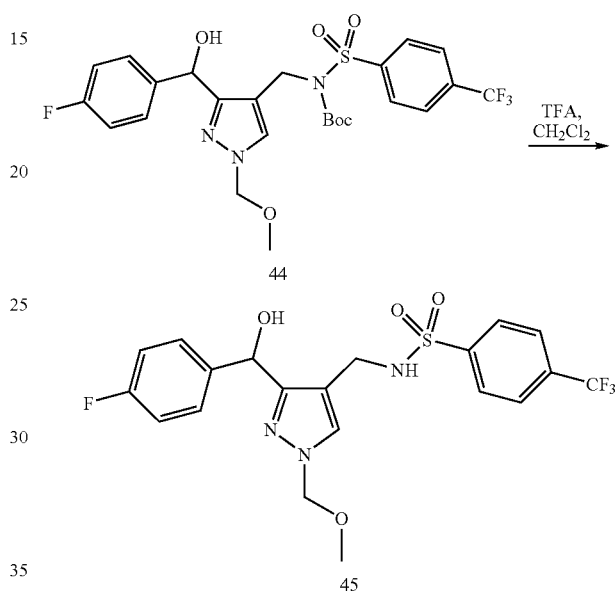

tert-Butyl (3-((4-fluorophenyl)(hydroxy)methyl)-1-(methoxymethyl)-1H-pyrazol-4-yl)methyl(4-(trifluoromethyl)phenylsulfonyl)carbamate (44) (434 mg, 0.757 mmol) was dissolved in $CH_2Cl_2$ (4 mL) and stirred at rt under nitrogen. Trifluoroacetic acid (4 mL) was added and the reaction stirred for 1 hr before concentration in vacuo. The resulting crude product was purified by column chromatography using EtOAc/hexane gradients to yield N-((3-((4-fluorophenyl)(hydroxy)methyl)-1-(methoxymethyl)-1H-pyrazol-4-yl)methyl)-4-(trifluoromethyl)benzenesulfonamide (45) (120 mg, 35%) as a white solid.

Step 6: 6-(4-Fluorophenyl)-2-(methoxymethyl)-5-(4-(trifluoromethyl)phenylsulfonyl)-2,4,5,6-tetrahydropyrrolo[3,4-c]pyrazole

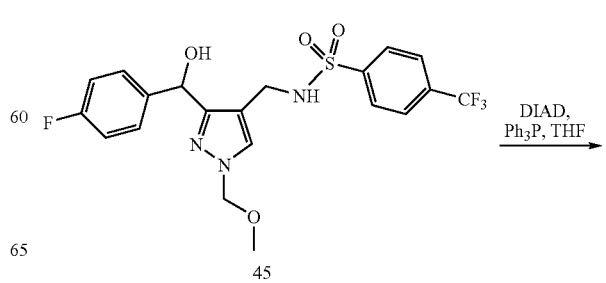

-continued

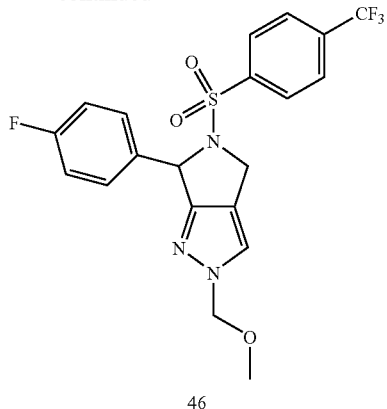

46

Diisopropyl azodicarboxylate (45 µL, 0.228 mmol) was added dropwise to a stirred solution of triphenylphosphine (60 mg, 0.228 mmol) and N-((3-((4-fluorophenyl)(hydroxy)methyl)-1-(methoxymethyl)-1H-pyrazol-4-yl)methyl)-4-(trifluoromethyl)benzenesulfonamide (45) (90 mg, 0.190 mmol) in THF (5 mL) under nitrogen at 0° C. Reaction was warmed to rt and stirred 16 hr. The reaction was concentrated in vacuo. The resulting crude product was purified via column chromatography using EtOAc/hexane gradients to yield 6-(4-fluorophenyl)-2-(methoxymethyl)-5-(4-(trifluoromethyl)phenylsulfonyl)-2,4,5,6-tetrahydropyrrolo[3,4-c]pyrazole (46) (64 mg, 71%) as a white solid.

Step 7: 6-(4-Fluorophenyl)-2-(methoxymethyl)-5-(4-(trifluoromethyl)phenylsulfonyl)-2,4,5,6-tetrahydropyrrolo[3,4-c]pyrazole

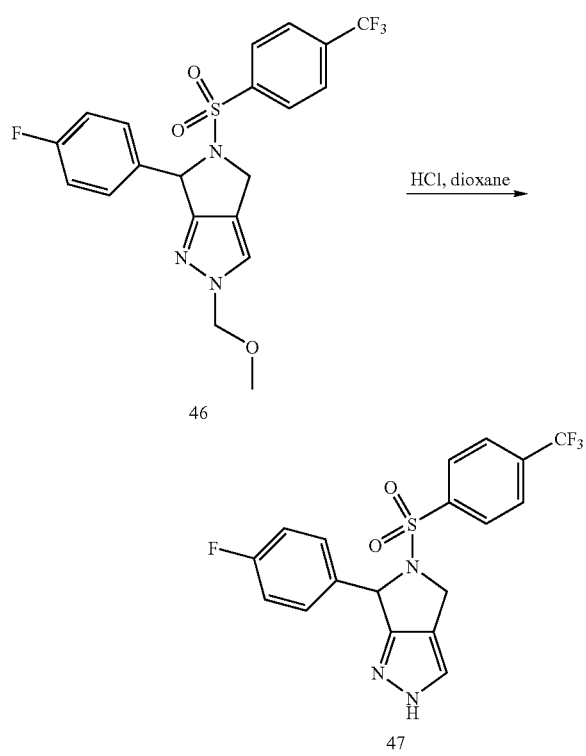

6-(4-Fluorophenyl)-2-(methoxymethyl)-5-(4-(trifluoromethyl)phenylsulfonyl)-2,4,5,6-tetrahydropyrrolo[3,4-c]pyrazole (46) (64 mg, 0.143 mmol) was dissolved in a solution of 4M HCl in dioxane (0.5 mL) and 6M HCl (0.5 mL). The reaction was heated to 70° C. and stirred for 16 hours. The reaction was rotary evaporated to dryness and the crude material (55 mg) was purified by preparative HPLC to yield 6-(4-fluorophenyl)-2-(methoxymethyl)-5-(4-(trifluoromethyl)phenylsulfonyl)-2,4,5,6-tetrahydropyrrolo[3,4-c]pyrazole (47) (2.5 mg, 4.2%) as a white solid.

BIOLOGICAL EXAMPLES

Notch Signaling Assay for Selective Inhibitors of Gamma Secretase

A convergence of evidence indicates that the gamma secretase complex, comprised of the presenilin subunits, mediates the intra-membrane cleavage of Amyloid precursor protein (APP), and the Notch family of proteins (De Strooper, B., et al. "Deficiency of presenilin-1 inhibits the normal cleavage of amyloid precursor protein." *Nature* 391 (6665): 387-90 (1998); De Strooper, B et al. "A presenilin-1-dependent gamma-secretase-like protease mediates release of Notch intracellular domain." *Nature* 398 (6727): 518-22 (1999); Mumm, J. S., et al "A ligand-induced extracellular cleavage regulates gamma-secretase-like proteolytic activation of Notch1." *Mol Cell* 5 (2):197-206 (2000); Zhang, Z et al. "Presenilins are required for gamma-secretase cleavage of beta-APP and transmembrane cleavage of Notch-1." *Nat Cell Biol* 2(7): 463-5 (2000)). Cleavage of APP by gamma secretase leads to beta-amyloid synthesis. Cleavage of Notch1 by gamma secretase results in release of the Notch intracellular domain (NICD), which translocates to the nucleus and activates gene expression (Jarriault, S., et al "Signalling downstream of activated mammalian Notch." *Nature* 377 (6547): 355-8 (1995).; Kopan, R., et al. "Signal transduction by activated Notch: importance of proteolytic processing and its regulation by the extracellular domain." *Proc Natl Acad Sci USA* 93 (4): 1683-8 (1996); Schroeter, E. et al "Notch-1 signalling requires ligand-induced proteolytic release of intracellular domain" *Nature* 393 (6683): 382-6 (1998)). In particular, Notch signaling activates transcription of the mammalian homolog of the *Drosophila* transcription factor hairy-enhancer of split (Hes). Transcriptional activation of Hes1 is mediated by de-repression of CBF1/RBPJk upon binding by NICD in the nucleus. These facts have been exploited to develop a reporter gene assay for Notch Signaling Hsieh, J. J. et al. "Truncated mammalian Notch1 activates CBF1/RBPJk-repressed genes by a mechanism resembling that of Epstein-Barr virus EBNA2." *Mol Cell Biol* 16(3): 952-9 (1996) and Lu, F. M. et al. "Constitutively active human Notch1 binds to the transcription factor CBF1 and stimulates transcription through a promoter containing a CBF1-responsive element" *Proc Natl Acad Sci USA* 93 (11): 5663-7 (1996).

Gamma secretase inhibitors have been observed to block NICD formation, and inhibit Notch signaling (De Strooper, B., et al. "A presenilin-1-dependent gamma-secretase-like protease mediates release of Notch intracellular domain." *Nature* 398(6727): 518-22 (1999)). Due to the importance of Notch signaling in cell fate determination, and tissue differentiation during both development and in the adult, inhibition of Notch signaling by gamma secretase inhibitors is thought to be a limiting factor in some of its therapeutic utilities. In order to identify gamma secretase inhibitors with some degree of selectivity over Notch, we have employed a reporter gene based Notch signaling assay using a constitutively active rat Notch1 construct (ZEDN1) provided by Dr Gerry Weinmaster, University of California at Los Angeles (UCLA) as described in Shawber, C., D. Nofziger, J. J. Hsieh, C. Lindsell, O. Bogler, D. Hayward and G. Weinmaster "Notch signaling inhibits muscle cell differentiation through a CBF1-independent pathway." *Development* 122 (12): 3765-73 (1996) in combination with the CBF1 repressible Luciferase reporter gene 4xwtCBF1Luc (Hsieh, J. J., et al. "Truncated mammalian Notch1 activates CBF1/RBPJk-repressed genes by a mechanism resembling that of Epstein-Barr virus EBNA2." *Mol Cell Biol* 16(3): 952-9 (1996).).

When 4xwtCBF1 Luciferase is co-transfected with NotchδE (ZEDN1), gamma-secretase cleavage of NotchδE releases the Notch intracellular domain (NICD), which translocates to the nucleus and de-represses CBF1 mediated transcriptional repression, leading to transcription of the Luciferase reporter gene. Luciferase activity is easily assayed in cell extracts using commercially available kits. The activity of the reporter gene is directly correlated with gamma secretase cleavage of NotchδE, and as such, a reduction in Luciferase activity provides a convenient measure of inhibition of gamma secretase cleavage of NotchδE. A comparison of the $IC_{50}$ values of compounds for inhibition of Notch signaling versus inhibition of beta-amyloid production in 293sw cells is employed to guide in the selection of compounds that have the desired property of potent inhibition of beta-amyloid synthesis with minimal inhibition of Notch Signaling.

Gamma-Secretase Assay

The gamma-secretase APP enzyme assay was designed to measure the specific proteolytic cleavage of an APP substrate (MBP-C125 Swe fusion protein) at the Aβ40 site. The assay used a partially purified extract of IMR-32 cell membranes as the gamma-secretase enzyme preparation and a recombinant fusion protein containing the C-terminal 125 amino acids of the Swedish variant of the APP (MBP-C125swe) as the substrate. This assay involved two steps beginning with the enzymatic reaction generating a cleavage product that was captured with an immobilized antibody specific for the neo-epitope Aβ40 site. The captured cleavage product was then detected in a sandwich ELISA assay with a biotinylated reporter antibody that is specific to Aβ (17-28). Streptavidin-linked alkaline phosphatase was then added that would generate a fluorescent signal proportional to the amount of cleavage product. This assay was used to discover small molecule inhibitors of gamma-secretase.

Materials and Methods:

Briefly, a 149 mg/ml solution of BIGCHAP detergent was made with water at 42° C. and then rotated for 30 minutes at the same temperature. This warmed solution of BigCHAPS (N,N-Bis(3-D-gluconamidopropyl)cholamide) detergent was used to dissolve Brain Extract Type-V (lipid containing a minimum of 40% phosphatidylethanolamine) from Sigma (St. Louis, Mo.) to a concentration of 8 mg/ml. This solution containing BigCHAPS and lipid at 8 mg/ml is then diluted to 0.53 mg/ml lipid with a pre-warmed solution of Hepes and sodium chloride. This final solution containing Hepes buffer, sodium chloride, BigCHAPS detergent and lipid is used to create working solutions of both gamma-secretase (25 Units) and the MBP-C125 substrate (0.05 mg/ml).

Gamma-secretase was then added to a 96-well micro-titre plate and then incubated with various concentrations of inhibitor for 30 minutes at 37° C. MBPC125 substrate was then added to initiate the reaction that would run for two hours at 37° C. The reaction was quenched with the addition of SDS to a final concentration of 0.1% and then 100 µl of the reaction mixture was transferred to a capture ELISA plate and incubated overnight at 4° C. Detection of the cleavage product was performed using a standard sandwich ELISA assay and quantified using a six point standard curve.

Results

The compounds of the invention have $IC_{50}$ values of 10 mM or less.

Data for some specific compounds is as follows.

| Compound | IC50 |
|---|---|
| 4-cyclopropyl-5-(4-(trifluoromethyl)phenylsulfonyl)-1,4,5,6-tetrahydropyrrolo[3,4-c]pyrazole | C |
| 5-(4-chlorophenylsulfonyl)-1,4,5,6-tetrahydropyrrolo[3,4-c]pyrazole | A |
| (R)-4-ethyl-5-(4-(trifluoromethyl)phenylsulfonyl)-1,4,5,6-tetrahydropyrrolo[3,4-c]pyrazole | C |
| (R)-4-cyclopropyl-5-(4-(trifluoromethyl)phenylsulfonyl)-1,4,5,6-tetrahydropyrrolo[3,4-c]pyrazole | C |
| 4,6-dicyclopropyl-5-(4-(trifluoromethyl)phenylsulfonyl)-1,4,5,6-tetrahydropyrrolo[3,4-c]pyrazole | C |
| 4-cyclopropyl-5-(4-(trifluoromethyl)phenylsulfonyl)-4,5-dihydropyrrolo[3,4-c]pyrazol-6(1H)-one | B |
| 4-cyclopropyl-6-(fluoromethyl)-5-(4-(trifluoromethyl)phenylsulfonyl)-1,4,5,6-tetrahydropyrrolo[3,4-c]pyrazole | C |
| (R)-4-cyclopropyl-5-(4-(trifluoromethyl)phenylsulfonyl)-1,4,5,6-tetrahydropyrrolo[3,4-c]pyrazole | C |
| ((4R)-4-cyclopropyl-5-(4-(trifluoromethyl)phenylsulfonyl)-1,4,5,6-tetrahydropyrrolo[3,4-c]pyrazol-6-yl)methanol | C |

In the above table, the IC50 data is defined as follows: A is<5000 nM, B is<2000 nM, C is<50 nM.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. Compounds of the formula:

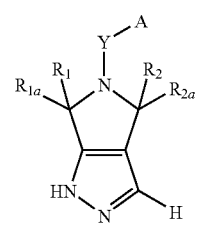

Formula I stereoisomers, tautomers, mixtures of stereoisomers and/or tautomers or pharmaceutically acceptable salts thereof, wherein A is $C_1$-$C_6$ alkyl, aryl, $C_3$-$C_6$ cycloalkyl, heteroaryl or heterocyclyl, wherein each ring is optionally substituted at a substitutable position with one or more of halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, hydroxyl, hydroxyalkyl, CN, aryloxy, arylalkyloxy, —$SO_2$—($C_1$-$C_6$ alkyl), —NR'R", $C_1$-$C_6$ alkanoyl, $C_0$-$C_3$alkyl-C(O)

OR', heteroaryl, heterocyclyl, aryl, arylalkyl, or —SO$_2$—NR'R", and wherein when A is C$_1$-C$_6$ alkyl, the C$_1$-C$_6$ alkyl group is optionally substituted at a substitutable position with one or more of halogen, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, C$_1$-C$_6$ haloalkoxy, hydroxyl, hydroxyalkyl, CN, aryloxy, arylalkyloxy, —SO$_2$—(C$_1$-C$_6$ alkyl), —NR'R", C$_1$-C$_6$ alkanoyl, C$_0$-C$_3$alkyl-C(O)OR', heteroaryl, heterocyclyl, aryl, arylalkyl, or —SO$_2$—NR'R", R$_1$, R$_{1a}$, R$_2$, and R$_{2a}$, are independently hydrogen, C$_1$-C$_6$ alkyl, C$_2$-C$_6$ alkenyl, C$_2$-C$_6$ alkynyl, C$_3$-C$_6$cycloalkyl, C$_3$-C$_6$cycloalkylC$_1$-C$_6$ alkyl, C$_1$-C$_6$ haloalkyl, aryl, arylC$_1$-C$_6$ alkyl, heteroaryl, heterocyclyl, —C(O)OR', —CONR'R", C$_1$-C$_4$ haloalkoxyalkyl, hydroxy C$_1$-C$_6$ alkyl, C$_1$-C$_6$ alkoxy, C$_2$-C$_6$ alkanoyl, aryloxyC$_1$-C$_6$ alkyl, heteroaryloxy C$_1$-C$_6$ alkyl, —C$_0$-C$_6$ alkyl-OC(O)NR'R", —C$_0$-C$_6$ alkyl-NR'R", hydroxyl, CN, or —C$_0$-C$_6$ alkyl-OC(O)-heterocyclyl, wherein each aryl, heteroaryl, and heterocyclyl group is optionally substituted with one or more groups that are independently halogen, C$_1$-C$_6$ alkyl, C$_1$-C$_6$ alkoxy, C$_1$-C$_6$alkanoyl, halo C$_1$-C$_4$ alkyl, halo C$_1$-C$_4$ alkoxy, —C(O)NR'R", —NR'R", hydroxyl, CN, or —C(O)OR'; or R$_1$ and R$_{1a}$, or R$_2$ and R$_{2a}$ together with the carbon to which they are attached form C$_3$-C$_6$ cycloalkyl group wherein one of the carbons is optionally replaced with a heteroatom selected from N, O or S and wherein said ring may be optionally substituted with C$_1$-C$_6$ alkyl; or R$_1$ and R$_{1a}$, or R$_2$ and R$_{2a}$ together with the carbon to which they are attached form an oxo group;

R' and R" are independently H or C$_1$-C$_6$ alkyl; or R' and R" together with the atom to which they are attached may form a 3-8 membered ring optionally including an additional heteroatom such as N, O or S;

Y is —SO$_2$—, —SO$_2$—O— or S0$_2$-NR$_{10}$—; and

R$_{10}$ is H or C$_1$-C$_6$ alkyl.

2. Compounds or salts according to claim 1, having the formula:

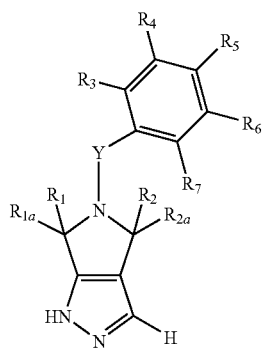

wherein,

R$_3$, R$_4$, R$_5$, R$_6$ and R$_7$ are independently H, halogen, C$_1$-C$_6$ alkyl, C$_1$-C$_6$ alkoxy, C$_1$-C$_6$ haloalkyl, C$_1$-C$_6$ haloalkoxy, hydroxyl, hydroxyalkyl, CN, aryloxy (e.g., phenyloxy), arylalkyloxy (e.g., benzyloxy), —SO$_2$—(C$_1$-C$_6$ alkyl), —NR'R", C$_1$-C$_6$ alkanoyl, aryl (e.g., phenyl), arylalkyl (e.g. benzyl), or —SO$_2$—NR'R", or R$_3$ and R$_4$ and the carbons to which they are attached form a bicyclic aryl ring or a heteroaryl ring selected from the group of thienyl, furanyl, pyrrolyl, thiazolyl, oxazolyl, imidazolyl, isothiazolyl, isoxazolyl and imidazolyl, each of which is optionally substituted with 1, 2, or 3 groups that are independently C$_1$-C$_4$ alkyl, C$_1$-C$_4$ alkoxy, halogen, C$_1$-C$_4$ haloalkyl, or C$_1$-C$_4$ alkanoyl, wherein the alkanoyl group is optionally substituted with up to 3 halogen atoms; or when R$_3$ and R$_4$ are not part of a ring, then R$_4$ and R$_5$ and the carbons to which they are attached may form a phenyl ring or a heteroaryl ring selected from the group of thienyl, furanyl, pyrrolyl, thiazolyl, oxazolyl, imidazolyl, isothiazolyl, isoxazolyl and imidazolyl, each of which is optionally substituted with 1, 2, or 3 groups that are independently C$_1$-C$_4$ alkyl, C$_1$-C$_4$ alkoxy, halogen, C$_1$-C$_4$ haloalkyl, or C$_1$-C$_4$ alkanoyl, wherein the alkanoyl group is optionally substituted with up to 3 halogen atoms; and R$_1$, R$_{1a}$, R$_2$, and R$_{2a}$, are independently hydrogen, C$_1$-C$_6$ alkyl, C$_2$-C$_6$ alkenyl, C$_2$-C$_6$ alkynyl, C$_3$-C$_6$cycloalkyl, C$_3$-C$_6$cycloalkylC$_1$-C$_6$ alkyl, aryl, arylC$_1$-C$_6$ alkyl, heteroaryl, heterocyclyl, —C(O)OR', —CONR'R", C$_1$-C$_6$ haloalkyl, C$_1$-C$_6$ haloalkoxy, C$_1$-C$_4$ haloalkoxyalkyl, hydroxy C$_1$-C$_6$ alkyl, C$_1$-C$_6$ alkoxy, C$_2$-C$_6$ alkanoyl, aryloxyC$_1$-C$_6$ alkyl, heteroaryloxy C$_1$-C$_6$ alkyl, —C$_0$-C$_6$ alkyl-OC(O)NR'R", —C$_0$-C$_6$ alkyl-NR'R", hydroxyl, CN, or —C$_0$-C$_6$ alkyl-OC(O)-heterocyclyl, wherein each aryl, heteroaryl, and heterocyclyl group is optionally substituted with one or more groups that are independently halogen, C$_1$-C$_6$ alkyl, C$_1$-C$_6$ alkoxy, C$_1$-C$_6$alkanoyl, halo C$_1$-C$_4$ alkyl, haloC$_1$-C$_4$ alkoxy, —C(O)NR'R", —NR'R", hydroxyl, CN, or —C(O)OR'; or R$_1$ and R$_{1a}$, or R$_2$ and R$_{2a}$ together with the carbon to which they are attached form C$_3$-C$_6$ cycloalkyl group wherein one of the carbons is optionally replaced with a heteroatom selected from N, O or S and wherein said ring may be optionally substituted with C$_1$-C$_6$ alkyl; or R$_1$ and R$_{1a}$, or R$_2$ and R$_{2a}$ together with the carbon to which they are attached form an oxo group; and R' and R" are independently H or C$_1$-C$_6$ alkyl; or R' and R" together with the atom to which they are attached form a 3-8 membered ring optionally including an additional heteroatom such as N, O or S.

3. Compounds or salts according to claim 1, having the formula:

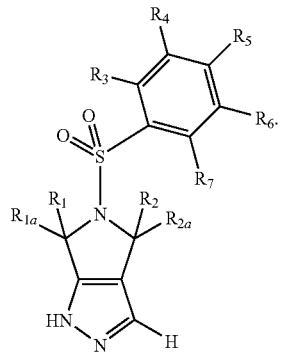

4. Compounds or salts according to claim 3, wherein R$_5$ is halogen or CF$_3$.

5. Compounds or pharmaceutically acceptable salts thereof, according to claim 1 that are 4-cyclopropyl-6-(fluoromethyl)-5-(4-(trifluoromethyl)phenylsulfonyl)-1,4,5,6-tetrahydropyrrolo[3,4-c]pyrazole;

5-(4-chlorophenylsulfonyl)-1,4,5,6-tetrahydropyrrolo[3,4-c]pyrazole;
(R)-4-ethyl-5-(4-(trifluoromethyl)phenylsulfonyl)-1,4,5,6-tetrahydropyrrolo[3,4-c]pyrazole;
(R)-4-cyclopropyl-5-(4-(trifluoromethyl)phenylsulfonyl)-1,4,5,6-tetrahydropyrrolo[3,4-c]pyrazole;
4,6-dicyclopropyl-5-(4-(trifluoromethyl)phenylsulfonyl)-1,4,5,6-tetrahydropyrrolo[3,4-c]pyrazole;
((4R)-4-cyclopropyl-5-(4-(trifluoromethyl)phenylsulfonyl)-1,4,5,6-tetrahydropyrrolo[3,4-c]pyrazol-6-yl)methanol;
6-(4-fluorophenyl)-5-(4-(trifluoromethyl)phenylsulfonyl)-1,4,5,6-tetrahydropyrrolo[3,4-c]pyrazole;
4-ethyl-5-(4-(trifluoromethyl)phenylsulfonyl)-1,4,5,6-tetrahydropyrrolo[3,4-c]pyrazole;
4-cyclopropyl-5-(4-(trifluoromethyl)phenylsulfonyl)-1,4,5,6-tetrahydropyrrolo[3,4-c]pyrazole;
(R)-4-cyclopropyl-5-(4-(trifluoromethyl)phenylsulfonyl)-1,4,5,6-tetrahydropyrrolo[3,4-c]pyrazole;
4,6-dicyclopropyl-5-(4-(trifluoromethyl)phenylsulfonyl)-1,4,5,6-tetrahydropyrrolo[3,4-c]pyrazole;
((4R)-4-cyclopropyl-5-(4-(trifluoromethyl)phenylsulfonyl)-1,4,5,6-tetrahydropyrrolo[3,4-c]pyrazol-6-yl)methanol;
6-(4-fluorophenyl)-5-(4-(trifluoromethyl)phenylsulfonyl)-1,4,5,6-tetrahydropyrrolo[3,4-c]pyrazole;
(S)-4-(4-fluorophenyl)-5-(4-(trifluoromethyl)phenylsulfonyl)-1,4,5,6-tetrahydropyrrolo[3,4-c]pyrazole;
(R)-4-(4-fluorophenyl)-5-(4-(trifluoromethyl)phenylsulfonyl)-1,4,5,6-tetrahydropyrrolo[3,4-c]pyrazole;
4-cyclopropyl-5-(4-(trifluoromethyl)phenylsulfonyl)-4,5-dihydropyrrolo[3,4-c]pyrazol-6(1H)-one.

6. Compounds or pharmaceutically acceptable salts thereof, according to claim 1 that are
4-(4-fluorophenyl)-6-(trifluoromethyl)-5-(4-(trifluoromethyl)phenylsulfonyl)-2,4,5,6-tetrahydropyrrolo[3,4-c]pyrazole;
4-(4-fluorophenyl)-6-(trifluoromethyl)-5-(6-(trifluoromethyl)pyridin-3-ylsulfonyl)-2,4,5,6-tetrahydropyrrolo[3,4-c]pyrazole;
4-cyclopropyl-6-(4-fluorophenyl)-5-(4-(trifluoromethyl)phenylsulfonyl)-2,4,5,6-tetrahydropyrrolo[3,4-c]pyrazole;
4-cyclopropyl-6-(4-fluorophenyl)-5-(6-(trifluoromethyl)pyridin-3-ylsulfonyl)-2,4,5,6-tetrahydropyrrolo[3,4-c]pyrazole;
5-(4-chlorophenylsulfonyl)-4-(4-fluorophenyl)-6-(trifluoromethyl)-2,4,5,6-tetrahydropyrrolo[3,4-c]pyrazole;
5-(4-chlorophenylsulfonyl)-4-cyclopropyl-6-(4-fluorophenyl)-2,4,5,6-tetrahydropyrrolo[3,4-c]pyrazole;
5-(4-chlorophenylsulfonyl)-6-(4-fluorophenyl)-4-(trifluoromethyl)-2,4,5,6-tetrahydropyrrolo[3,4-c]pyrazole;
5-(4-chlorophenylsulfonyl)-6-cyclopropyl-4-(4-fluorophenyl)-2,4,5,6-tetrahydropyrrolo[3,4-c]pyrazole;
6-(4-fluorophenyl)-4-(trifluoromethyl)-5-(4-(trifluoromethyl)phenylsulfonyl)-2,4,5,6-tetrahydropyrrolo[3,4-c]pyrazole;
6-(4-fluorophenyl)-4-(trifluoromethyl)-5-(6-(trifluoromethyl)pyridin-3-ylsulfonyl)-2,4,5,6-tetrahydropyrrolo[3,4-c]pyrazole;
6-cyclopropyl-4-(4-fluorophenyl)-5-(4-(trifluoromethyl)phenylsulfonyl)-2,4,5,6-tetrahydropyrrolo[3,4-c]pyrazole; and
6-cyclopropyl-4-(4-fluorophenyl)-5-(6-(trifluoromethyl)pyridin-3-ylsulfonyl)-2,4,5,6-tetrahydropyrrolo[3,4-c]pyrazole.

7. A pharmaceutical composition comprising a compound or salt of claim 1 and at least one pharmaceutically acceptable solvent, adjuvant, excipient, carrier, binder or disintegrant.

8. Compounds according to claim 2, wherein $R_3$, $R_4$, $R_5$, $R_6$, and $R_7$ are independently of each other hydrogen, halogen, $C_1$-$C_2$alkyl, halo$C_1$-$C_2$alkyl, $C_1$-$C_2$ alkoxy, halo$C_1$-$C_2$ alkoxy, phenyloxy, benzyloxy, —$SO_2$—($C_1$-$C_4$ alkyl), —NR'R", $C_1$-$C_6$ alkanoyl, phenyl, benzyl, or benzoyl.

9. Compounds according to claim 2, wherein $R_3$, $R_4$, $R_5$, $R_6$, and $R_7$ are independently of each other H, Cl, F, $CF_3$, $CHF_2$ methoxy, $OCF_3$, or $OCHF_2$.

\* \* \* \* \*